US012071422B2

(12) United States Patent
Lebl et al.

(10) Patent No.: US 12,071,422 B2
(45) Date of Patent: Aug. 27, 2024

(54) PROCESS FOR SYNTHESIS OF QUINAZOLINE COMPOUNDS

(71) Applicants: Genentech, Inc., South San Francisco, CA (US); Hoffmann-La Roche Inc., Little Falls, NJ (US)

(72) Inventors: Rene Lebl, Graz (AT); Ngiap Kie Lim, Dublin, CA (US); Roland Christoph Meier, Ueken (CH); Ugo Jonathan Orcel, Basel (CH); Joerg Sedelmeier, Basel (CH); Jeff Shen, Foster City, CA (US); Lauren Elizabeth Sirois, San Francisco, CA (US); Jacob C. Timmerman, Redwood City, CA (US); Etienne Trachsel, Basel (CH); Nicholas Andrew White, San Francisco, CA (US); Jie Xu, San Mateo, CA (US); Haiming Zhang, San Mateo, CA (US); Stephan Bachmann, Allschwil (CH); Thomas Michael Bass, Fremont, CA (US); Raphael Bigler, Aarau (CH); Johannes Adrian Burkhard, Millbrae, CA (US); Kyle Bradley Pascual Clagg, San Francisco, CA (US); Francis Gosselin, San Mateo, CA (US); Chong Han, Foster City, CA (US); Dainis Kaldre, Lorrach (DE); Sean M. Kelly, San Mateo, CA (US); Sebastian Herold, Bad Saeckingen (DE); Christian Leitner, Eiken (CH)

(73) Assignees: Genentech, Inc., South San Francisco, CA (US); Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 18/164,302

(22) Filed: Feb. 3, 2023

(65) Prior Publication Data
US 2023/0250074 A1    Aug. 10, 2023

Related U.S. Application Data

(60) Provisional application No. 63/307,529, filed on Feb. 7, 2022.

(51) Int. Cl.
*C07D 401/04* (2006.01)
*B01J 23/44* (2006.01)
*B01J 23/755* (2006.01)

(52) U.S. Cl.
CPC ............ *C07D 401/04* (2013.01); *B01J 23/44* (2013.01); *B01J 23/755* (2013.01)

(58) Field of Classification Search
CPC ........ C07D 401/04; B01J 23/44; B01J 23/755
See application file for complete search history.

(56) References Cited

U.S. PATENT DOCUMENTS

2022/0081413 A1    3/2022   Lim et al.

FOREIGN PATENT DOCUMENTS

| WO | 2020/097537 A2 | 5/2020 |
| WO | 2022/035790 A1 | 2/2022 |

OTHER PUBLICATIONS

International Search Report with Written Opinion—PCT/US2023/061895 mailed Jun. 23, 2023, pp. 1-13.

*Primary Examiner* — Sikarl A Witherspoon
(74) *Attorney, Agent, or Firm* — Genentech, Inc.

(57) ABSTRACT

Provided herein are methods to synthesize compounds useful in the treatment of cancer where such compounds comprise a quinazolinyl core moiety and at least one stereoisomeric or atropisomeric moiety.

48 Claims, 1 Drawing Sheet

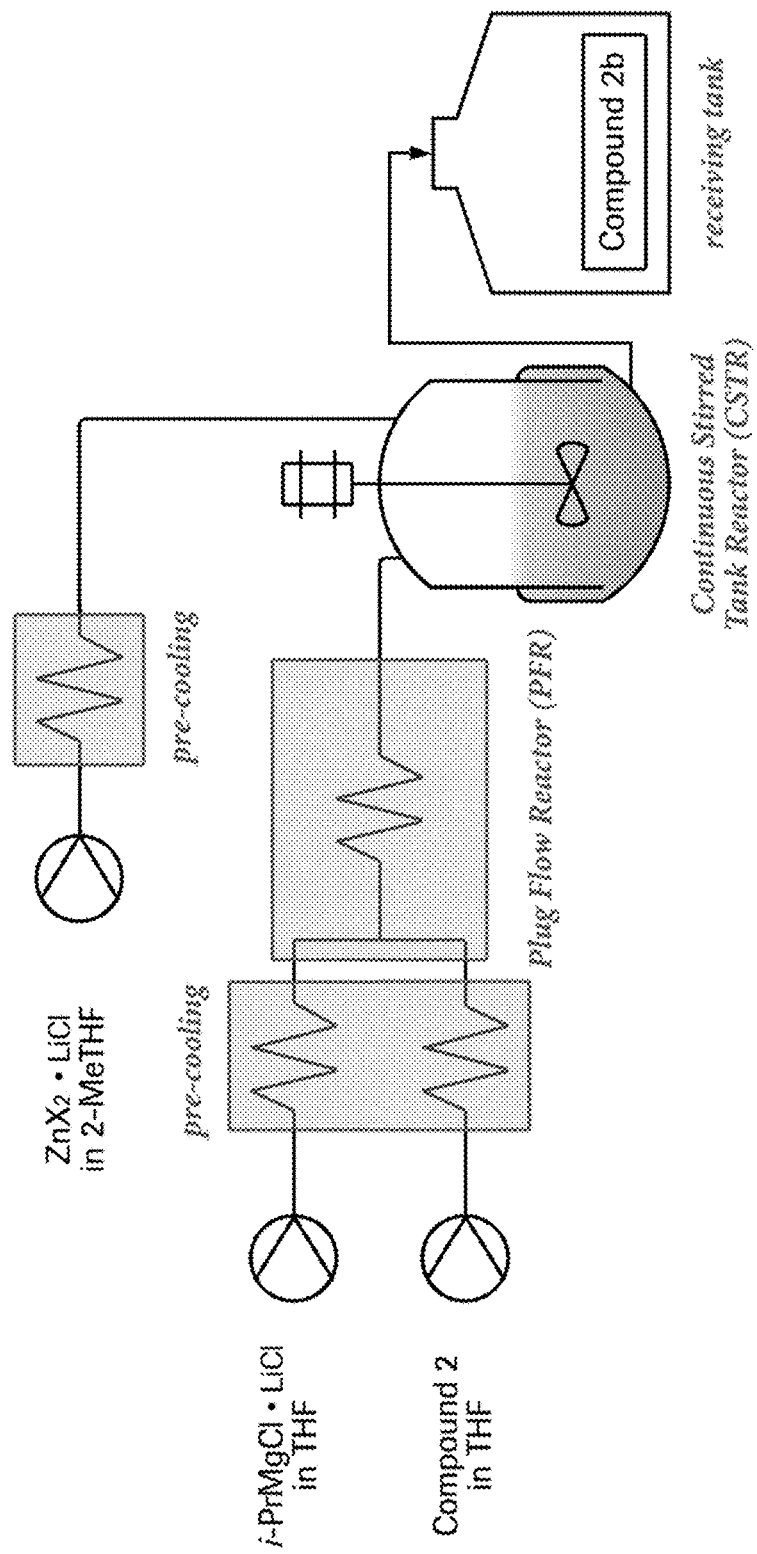

PROCESS FOR SYNTHESIS OF QUINAZOLINE COMPOUNDS

CROSS REFERENCE TO RELATED APPLICATIONS

This application claims the benefit of U.S. Provisional Patent Application No. 63/307,529, filed 7 Feb. 2022, and is incorporated herein by reference in its entirety and for all purposes.

FIELD OF THE INVENTION

Provided herein are methods to synthesize compounds useful in the treatment of cancer where such compounds comprise a quinazolinyl core moiety and at least one stereoisomeric or atropisomeric moiety.

BACKGROUND

The configuration at a biaryl axis often plays an important role for pharmacological properties of bioactive compounds and is a fundamental basis for useful reagents and catalysts in asymmetric synthesis. Highly atroposelective cross-couplings, especially those of heterocycles for the synthesis of biheteroaryls, remain a challenging and unsolved problem. Moreover, scale up of such processes to commercial/industrial scale can often lead to unforeseen and unexpected difficulties with process and synthesis. The present disclosure provides improved processes for the atroposelective synthesis of aminopyridinyl-quinazolinyl compounds via Negishi coupling utilizing a chiral ligand such as chiraphite.

Accordingly, there is a pressing need for processes that allow for efficient and effective scale up for the synthesis of compounds such as those described herein.

SUMMARY

Provided herein are solutions to the problems above and other problems in the art.

In a first aspect provided herein is a process for the synthesis of a compound of formula (I) as described herein comprising (a) contacing a compound fo formula (II) as described herein with an organomagnesium compound thereby forming a compound of formula (IIa) as described herein; (b) transferring the compound of formula (IIa) of step (a) to a continuous stirred tank reactor (CSTR) comprising a zinc compound thereby synthesizing a compound of formula (IIb) as described herein; and contacting the compound (IIb) of step (b) with a compound of formula (III) as described herein, a transition metal catalyst precursor as described herein, and a chiral ligand as described herein, thereby synthesizing a compound of formula (I).

In one embodiment, the compound of formula (II) is prepared according to the process P2 as described herein.

In one embodiment, the compound of formula (III) is prepared according to the process P4 as described herein.

In one embodiment of the processes described herein, formula (I) comprises a compound of formula (Ia), (Ib), (Ic), or (Id) as described herein.

In one embodiment of the processes described herein, formula (I) comprises a compound of formula (1) as described herein.

In another aspect provided herein is a process (P5) for the synthesis of a compound of formula (2) as described herein comprising (a) contacting a compound of formula (4a) as described herein with i-PrMgCl followed by hydroxylamine, thereby synthesizing the compound of formula (4c) as described herein; (b) contacting the compound of formula (4c) as described herein with TFAA and triethylamine in acetonitrile followed by ammonia, thereby synthesizing the compound of formula (4e) as described herein; contacting the compound of (4e) as described herein with a chlorinating agent, thereby synthesizing the compound of formula (4) as described herein; contacting the compound of (4) as described herein with $CO_2$ in the presence of DBU, thereby synthesizing the compound of formula (5); contacting the compound of formula (5) as described herein with $POCl_3$ and DIPEA followed by tert-butyl (S)-3-methylpiperazine-1-carboxylate in DIPEA, thereby synthesizing the compound of formula (5b); and contacting the compound of (5b) as described herein with KF, DABCO, and MsOH, thereby forming the compound of formula (2) as described herein.

In another aspect provided herein is a process (P7) comprising the synthesis of a compound of formula (G) or a tautomer, stereoisomer, atropisomer, or pharmaceutically acceptable salt thereof as described herein, comprising contacting the compound of formula (I) or a solvate, tautomer, stereoisomer, atropisomer, or salt thereof with a moiety comprising $X^A$ as described herein in the presence of base as described herein and an activating agent as described herein, thereby synthesizing a compound of formula (G1) as described herein; removing the PG groups and optionally $R^1$ from the compound of formula (G1); and contacting the compound of step (b) with a compound of formula (VII) as described herein in the presence of an activating agent as described herein, followed by contacting with a base as described herein, thereby making a compound of formula (G) or a tautomer, stereoisomer, atropisomer, or pharmaceutically acceptable salt thereof.

Still further provided herein is a process (P8) for the synthesis of a compound of formula (1) or a pharmaceutically acceptable salt thereof as described herein comprising: contacting a precooled solution comprising a compound of formula (2) or a salt thereof as described herein with a pre-cooled solution comprising i-PrMgCl·LiCl using a flow rate resulting in a residence time of about 15-150 seconds for the Mg—Br exchange thereby synthesizing a compound of formula (2a) as described herein; transferring the compound of formula (2a) of step (a) to a continuous stirred tank reactor (CSTR) comprising a solution of $ZnCl_2$ or $Zn(OPiv)_2$ and maintaining a constant residence time of about 3-7 minutes at about −20° C. to 20° C. thereby synthesizing a compound of formula (2b) as described herein; contacting the compound of formula (2b) with NaTFA and a compound of formula (3) as described herein; contacting the mixture of step (c) or a salt thereof with a Pd or Ni catalyst precursor and a chiral ligand thereby synthesizing a compound of formula (11) or a solvate or salt thereof as described herein; contacting the compound of formula (11) or a solvate or salt thereof, with a compound of formula HO—$X^A$, wherein $X^A$ has formula

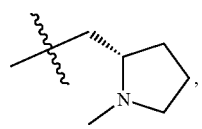 [SMILES: *C[C@@H]1CCCN1C]

and a base as described herein thereby synthesizing a compound of formula (Ib) or a solvate or pharmaceutically acceptable salt thereof as described herein; contacting the compound of formula (Ib) with MsOH in an acid thereby synthesizing a compound of formula (Ia) or a solvate or pharmaceutically acceptable salt thereof as described herein; and contacting the compound of formula (Ia) or a solvate or pharmaceutically acceptable salt thereof with

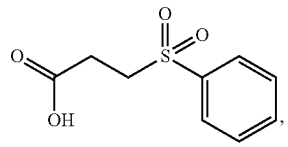 [SMILES: O=C(O)CCS(=O)(=O)c1ccccc1]

in the presence of an activating agent, followed by contacting with a base, thereby making a compound of formula (1) or a pharmaceutically acceptable salt thereof.

The present embodiments can be understood more fully by reference to the detailed description and examples, which are intended to exemplify non-limiting embodiments.

BRIEF DESCRIPTION OF THE FIGURES

FIG. 1 depicts an exemplary hardware setup for the continuous flow reactions described herein.

DETAILED DESCRIPTION

Unless defined otherwise, all technical and scientific terms used herein have the same meaning as commonly understood by those of ordinary skill in the art to which the invention belongs. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention.

The following definitions are provided to facilitate understanding of certain terms used frequently herein and are not meant to limit the scope of the present disclosure. All references referred to herein are incorporated by reference in their entirety.

As used herein, and unless otherwise specified, the terms "about" and "approximately," when referring to doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. The equivalent dose, amount, or weight percent can be within 30%, 20%, 15%, 10%, 5%, 1%, or less of the specified dose, amount, or weight percent.

The term "residence time" refers to the residence time distribution (RTD) of a continuous flow system and is a probability distribution function that describes the amount of time a molecule or compound could spend inside the reactor setup.

The terms "halogen" and "halo" are used interchangeably herein and refer to F, Cl, Br, or I.

The term "alkyl" refers to a saturated linear or branched-chain monovalent hydrocarbon group. In one example, the alkyl group is one to eighteen carbon atoms ($C_{1-18}$). In other examples, the alkyl group is $C_{1-12}$, $C_{1-10}$, $C_{1-8}$, $C_{1-6}$, $C_{1-5}$, $C_{1-4}$, or $C_{1-3}$. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl and 1-octyl.

The term "haloalkyl" refers to an alkyl chain in which one or more hydrogen has been replaced by a halogen. Examples of haloalkyls are trifluoromethyl, difluoromethyl, and fluoromethyl. A "fluoroalkyl" refers to an alkyl chain in which one or more hydrogen has been replaced by F.

The term "amino" refers to —$NH_2$.

The terms "cyano" and "nitrile" are used interchangeably herein and refer to —C≡N or —CN.

The term "cyanoalkyl" refers to alkyl substituted with one cyano substituent.

The term "hydroxy" refers to —OH.

"Fused" refers to any ring structure described herein that shares one or more atoms (e.g., carbon or nitrogen atoms) with an existing ring structure in the compounds of the invention.

A "halogenating agent" as used herein refers to any reagent that adds one or more halogens to a compound described herein. A "chlorinating agent" as used herein refers to any reagent that adds one or more chlorine (Cl) atoms to a compound described herein. In one embodiment, the chlorinating agent is NCS or DCH as described herein. A "brominating" or "iodination" agent as used herein refers to any reagent that adds one or more bromine (Br) or iodine (I) atoms, respectively, to a compound described herein.

A "haloalkylation agent" as used herein refers to any reagent that adds one or more haloalkyl groups (e.g. $CF_3$) to a compound described herein. A "fluoroalkylation agent" refers to a reagent that adds one or more fluoroalkyl groups to a compound described herein.

An "organomagnesium compound" is organometallic compound in which the metal is magnesium.

Compounds of the invention may contain one or more chiral carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

The term "stereoisomers" refer to compounds that have identical chemical constitution, but differ with regard to the arrangement of the atoms or groups in space. Stereoisomers include diastereomers, enantiomers, atropisomers, conformers, and the like.

The term "chiral" refers to molecules which have the property of non-superimposability of the mirror image partner, while the term "achiral" refers to molecules which are superimposable on their mirror image partner.

The term "diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

The term "enantiomers" refer to two stereoisomers of a compound which are non-superimposable mirror images of one another.

"Atropisomers" are stereoisomers arising because of hindered rotation around a single bond or axis, where energy differences due to steric strain or other contributors create a barrier to rotation that is high enough to allow for isolation of individual conformers.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "amino-protecting group" as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are PMB (p-methoxybenzyl), Boc (tert-butyloxycarbonyl), Fmoc (9-fluorenylmethyloxycarbonyl), Cbz (carbobenzyloxy), Ac (acetyl), trifluoroacetyl, phthalimide, Bn (benzyl), Tr (triphenylmethyl or trityl), benzylidenyl, p-toluenesulfonyl, or DMB (dimethoxybenzyl). In some embodiments, an amino protecting group can be a group used to block or protect an amino group which results from cyclization of groups attached to the amino group but which can be later removed or replaced. Such examples include 1,3,5-dioxazinane, 2,4-dimethyl-1,3,5-dioxazinane, 2,2,5,5-tetramethyl-1,2,5-azadisilolidine, and isoindoline-1,3-dione. Further exemplary amino-protecting groups are found in T. W. Greene and P. G. M. Wuts, "Protecting Groups in Organic Synthesis, $3^{rd}$ ed., John Wiley & Sons, Inc., 1999. The term "protected amino" refers to an amino group substituted with one of the above amino-protecting groups.

The term "leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal.

The terms "antagonist" and "inhibitor" are used interchangeably, and they refer to a compound having the ability to inhibit a biological function of a target protein, whether by inhibiting the activity or expression of the protein, such as K-Ras, H-Ras or N-Ras G12C. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, diffuse large B-Cell lymphoma (DLBCL), central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

The term "treatment" refers to clinical intervention designed to alter the natural course of the patient or cell being treated during the course of clinical pathology. Desirable effects of treatment include decreasing the rate of disease progression, ameliorating or palliating the disease state, and remission or improved prognosis. For example, a patient is successfully "treated" if one or more symptoms associated with a breast cancer described herein are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of patients.

The term "delaying progression" of a disease refers to deferring, hindering, slowing, retarding, stabilizing, and/or postponing development of a breast cancer described herein. This delay can be of varying lengths of time, depending on the history of the cancer and/or patient being treated. As is evident to one skilled in the art, a sufficient or significant delay can, in effect, encompass prevention, in that the patient does not develop cancer.

An "effective amount" is at least the minimum amount required to effect a measurable improvement or prevention of a breast cancer described herein. An effective amount herein may vary according to factors such as the disease state, age, sex, and weight of the patient, and the ability of the agent to elicit a desired response in the patient. An effective amount is also one in which any toxic or detrimental effects of the treatment are outweighed by the therapeutically beneficial effects. Beneficial or desired results include results such as eliminating or reducing the risk, lessening the severity, delaying the onset of the disease (including biochemical, histological and/or behavioral symptoms of the disease, its complications and intermediate pathological phenotypes presenting during development of the disease), decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In some embodiments, an effective amount of the drug may have the effect in reducing the number of cancer cells; reducing the tumor size; inhibiting (i.e., slow or stop) cancer cell infiltration into peripheral organs; inhibit (i.e., slow or stop) tumor metastasis; inhibiting (i.e., slow or stop) tumor growth; and/or relieving one or more of the symptoms associated with the disorder. An effective amount can be administered in one or more administrations. An effective amount of drug, compound, pharmaceutical composition, or combination therapy described herein can be an amount sufficient to accomplish therapeutic treatment either directly or indirectly. As is understood in the clinical context, an effective amount of a drug, compound, or pharmaceutical composition may or may not be achieved in conjunction with another drug, compound, or pharmaceutical composition, or combination therapy. Thus, an "effective amount" may be considered in the context of administering one or more therapeutic agents, and a single agent may be considered to be given in an effective amount if, in conjunction with one or more other agents, a desirable result may be or is achieved.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

Throughout this application, the term "about" is used to indicate that a value includes the standard deviation of error for the device or method being employed to determine the value.

Provided herein are processes for the synthesis of a compound of formula (I):

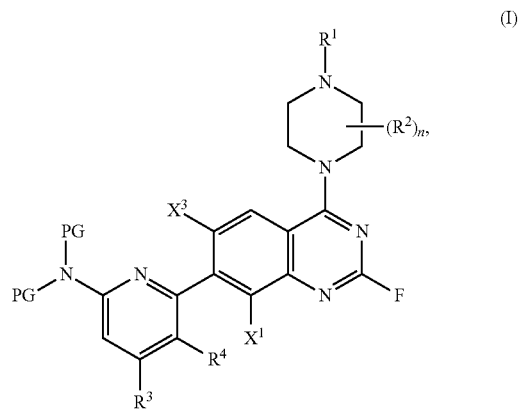

or a solvate, tautomer, stereoisomer, atropisomer, or salt thereof.

In one embodiment is a process (P1) for the synthesis of a compound of formula (I):

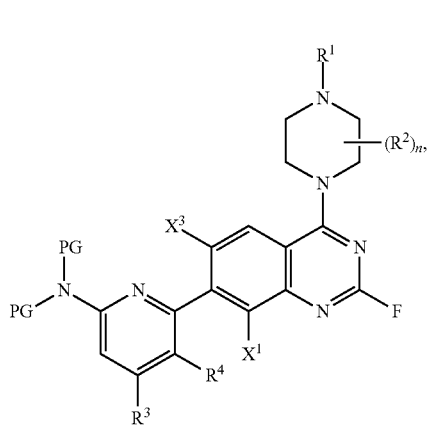

(I)

or a solvate, tautomer, stereoisomer, atropisomer, or salt thereof, wherein $X^1$ and $X^3$ are each independently hydrogen or halogen;

$R^1$ is hydrogen or $PG^1$;

each $R^2$ is independently halogen, cyano, unsubstituted $C_{1-6}$ alkyl, unsubstituted $C_{1-6}$ cyanoalkyl, or unsubstituted $C_{1-6}$ haloalkyl;

$R^3$ is hydrogen, halogen, $R^{3A}$-substituted or unsubstituted $C_{1-3}$ alkyl, $R^{3A}$-substituted or unsubstituted $C_{1-3}$ haloalkyl, or $R^{3A}$-substituted or unsubstituted cyclopropyl;

$R^{3A}$ is halogen, OH, CN, unsubstituted $C_{1-3}$ alkyl or unsubstituted $C_{1-3}$ haloalkyl;

$R^4$ is $R^{4A}$-substituted or unsubstituted $C_{1-3}$ haloalkyl;

$R^{4A}$ is unsubstituted $C_{1-3}$ alkyl;

n is 1 or 2;

each PG is independently an amino protecting group; and $PG^1$ is an amino protecting group;

wherein the process comprises (a) contacting a compound of formula (II)

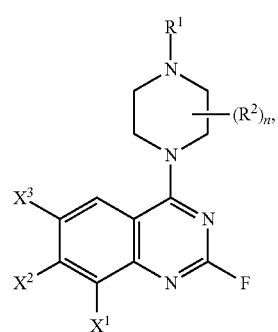

(II)

wherein $X^2$ is halogen;

with an organomagnesium compound thereby forming a compound of formula (IIa):

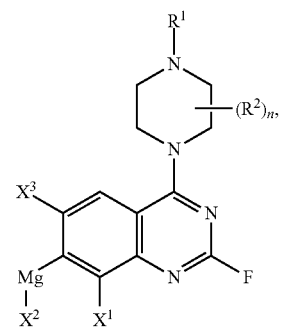

(IIa)

(b) transferring the compound of formula (IIa) of step (a) to a continuous stirred tank reactor (CSTR) comprising a zinc compound thereby synthesizing a compound of formula (IIb); and

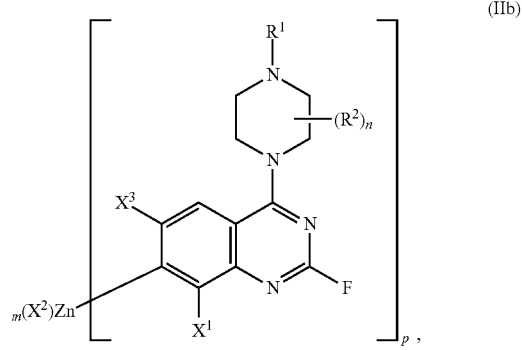

(IIb)

wherein m is 0, 1, or 2;

p is 1, 2, or 3; and $X^2$ is halogen or OPiv;

(c) contacting the compound (IIb) of step (b) with a compound of formula (III),

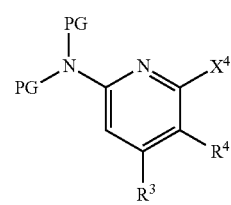

(III)

wherein $X^4$ is halogen, a transition metal catalyst precursor, and a chiral ligand, thereby synthesizing a compound of formula (I).

In one embodiment, $X^1$ is halogen. In one such embodiment, $X^1$ is F or Cl. In one embodiment, $X^3$ is halogen. In one such embodiment, $X^3$ is F or Cl. In another embodiment, both $X^1$ and $X^3$ are independently halogen. In one such embodiment, $X^1$ is F and $X^3$ is halogen. In one such embodiment, $X^3$ is Cl and $X^1$ is halogen. In one such embodiment, $X^1$ is F and $X^3$ is Cl.

In one embodiment, the compound of formula (IIb) is:

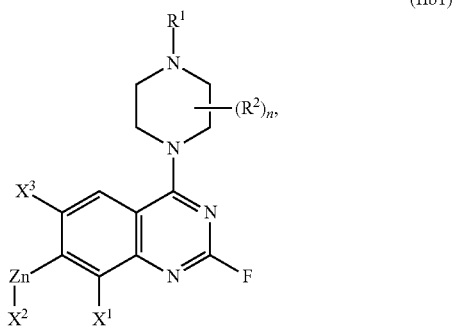

(IIb1)

wherein $X^1$, $X^2$, $X^3$, $R^1$, $R^2$, and n are as described herein.

In one embodiment, $X^2$ is Cl, Br, or OPiv. In one embodiment, $X^2$ is Cl or Br. In one embodiment, $X^2$ is Br. In one embodiment, $X^2$ is Cl.

In one embodiment of the compound of formula (IIb), $X^2$ is Cl, m is 1 or 2, and p is 1. In one embodiment of the compound of formula (IIb), $X^2$ is Cl, m is 1 or 2, and p is 2. In one embodiment of the compound of formula (IIb), $X^2$ is Cl, m is 1 or 2, and p is 3.

In one embodiment of the compound of formula (IIb), $X^2$ is Cl, m is 0 and p is 2. In one embodiment of the compound of formula (IIb), $X^2$ is Cl, m is 0 and p is 3.

In one embodiment of the compound of formula (IIb), $X^2$ is Cl, m is 1, and p is 1. In one embodiment of the compound of formula (IIb), $X^2$ is Cl, m is 1, and p is 2. In one embodiment of the compound of formula (IIb), $X^2$ is Cl, m is 1, and p is 3.

In one embodiment of the compound of formula (IIb), $X^2$ is Cl, m is 2, and p is 1. In one embodiment of the compound of formula (IIb), $X^2$ is Cl, m is 2, and p is 2. In one embodiment of the compound of formula (IIb), $X^2$ is Cl, m is 2, and p is 3.

In one embodiment of the compound of formula (IIb), $X^2$ is Br, m is 1 or 2, and p is 1. In one embodiment of the compound of formula (IIb), $X^2$ is Br, m is 1 or 2, and p is 2. In one embodiment of the compound of formula (IIb), $X^2$ is Br, m is 1 or 2, and p is 3.

In one embodiment of the compound of formula (IIb), $X^2$ is Br, m is 0 and p is 2. In one embodiment of the compound of formula (IIb), $X^2$ is Br, m is 0 and p is 3.

In one embodiment of the compound of formula (IIb), $X^2$ is Br, m is 1, and p is 1. In one embodiment of the compound of formula (IIb), $X^2$ is Br, m is 1, and p is 2. In one embodiment of the compound of formula (IIb), $X^2$ is Cl, m is 1, and p is 3.

In one embodiment of the compound of formula (IIb), $X^2$ is Br, m is 2, and p is 1. In one embodiment of the compound of formula (IIb), $X^2$ is Br, m is 2, and p is 2. In one embodiment of the compound of formula (IIb), $X^2$ is Br, m is 2, and p is 3.

In one embodiment of the compound of formula (IIb), $X^2$ is OPiv, m is 1 or 2, and p is 1. In one embodiment of the compound of formula (IIb), $X^2$ is OPiv, m is 1 or 2, and p is 2.

In one embodiment of the compound of formula (IIb), $X^2$ is OPiv, m is 1 or 2, and p is 3.

In one embodiment of the compound of formula (IIb), $X^2$ is OPiv, m is 0 and p is 2.

In one embodiment of the compound of formula (IIb), $X^2$ is OPiv, m is 0 and p is 3.

In one embodiment of the compound of formula (IIb), $X^2$ is OPiv, m is 1, and p is 1.

In one embodiment of the compound of formula (IIb), $X^2$ is OPiv, m is 1, and p is 2. In one embodiment of the compound of formula (IIb), $X^2$ is OPiv, m is 1, and p is 3.

In one embodiment of the compound of formula (IIb), $X^2$ is OPiv, m is 2, and p is 1. In one embodiment of the compound of formula (IIb), $X^2$ is OPiv, m is 2, and p is 2. In one embodiment of the compound of formula (IIb), $X^2$ is OPiv, m is 2, and p is 3.

In another embodiment, the compound of formula (IIb) has formula:

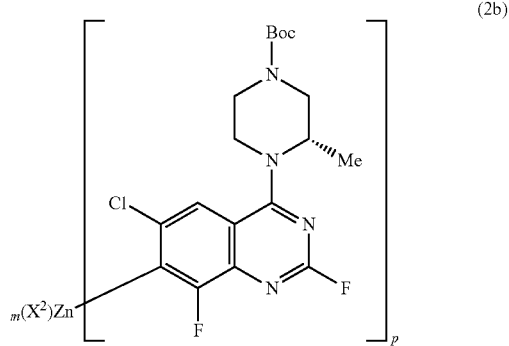

(2b)

where p and m are as described herein. In one embodiment, $X^2$ is Cl when the zinc compound comprises Cl. In one embodiment, $X^2$ is OPiv when the zinc compound comprises OPiv. In one embodiment, compound 2b is a mixture of compounds wherein one or more of $X^2$, m, and p are different. In one embodiment, compound 2b comprises at least 2 or 3 different species. In one such embodiment, such species can interconvert.

In one embodiment, $R^1$ is $PG^1$, where $PG^1$ is as described herein. In one such embodiment, $PG^1$ is Ac (acetyl), trifluoroacetyl, Bn (benzyl), Tr (triphenylmethyl or trityl), benzylidenyl, p-toluenesulfonyl, PMB (p-methoxybenzyl), Boc (tert-butyloxycarbonyl), Fmoc (9-fluorenylmethyloxycarbonyl) or Cbz (carbobenzyloxy). In one embodiment, $PG^1$ is an acid-labile amino protecting group. In one embodiment, $PG^1$ is tert-Butyloxycarbonyl (Boc).

In one embodiment, each $R^2$ is independently halogen or cyano. In another such embodiment, each $R^2$ is independently unsubstituted $C_{1-6}$ alkyl, unsubstituted $C_{1-6}$ cyanoalkyl, or unsubstituted $C_{1-6}$ haloalkyl. In one embodiment, each $R^2$ is independently unsubstituted $C_{1-3}$ alkyl. In one such embodiment, each $R^2$ is independently methyl or ethyl. In one embodiment, each $R^2$ is independently methyl. In one such embodiment, $R^2$ is methyl and n is 1. In one such embodiment, each $R^2$ is independently methyl or ethyl and n is 1. In another embodiment, each $R^2$ is independently unsubstituted $C_{1-3}$ cyanoalkyl or unsubstituted $C_{1-3}$ haloalkyl. In one such embodiment, unsubstituted $C_{1-6}$ cyanoalkyl, or unsubstituted $C_{1-6}$ haloalkyl $CH_2F$, $CHF_2$, $CF_3$, $CH_2CH_2F$, $CH_2CHF_2$, $CH_2CF_3$, $CH_2CN$, or $CH_2CH_2CN$. In one such embodiment, unsubstituted $C_{1-6}$ cyanoalkyl, or unsubstituted $C_{1-6}$ haloalkyl $CH_2F$, $CHF_2$, $CF_3$, $CH_2CH_2F$, $CH_2CHF_2$, $CH_2CF_3$, $CH_2CN$, or $CH_2CH_2CN$, where n is 1. In one embodiment, $R^2$ is unsubstituted $C_{1-6}$ alkyl or unsubstituted $C_{1-6}$ cyanoalkyl.

In one embodiment, $R^3$ is hydrogen, halogen, or $R^{3,4}$-substituted or unsubstituted $C_{1-3}$ alkyl. In one embodiment, $R^3$ is $R^{3,4}$-substituted or unsubstituted $C_{1-3}$ haloalkyl, or R$^{3A}$-substituted or unsubstituted cyclopropyl. In one embodiment, R$^3$ is hydrogen or R$^{3A}$-substituted or unsubstituted C$_{1-3}$ alkyl. In one embodiment, R$^3$ is hydrogen or methyl. In one embodiment, R$^3$ is methyl. In one embodiment, R$^3$ is hydrogen and R$^4$ is CF$_3$. In another embodiment, R$^3$ is methyl and R$^4$ is CF$_3$.

In one embodiment, R$^4$ is CF$_3$, CHF$_2$, or CH$_2$F.

In one embodiment, each PG is independently a protecting group selected from the group consisting of Ac (acetyl), trifluoroacetyl, phthalimide, Bn (benzyl), Tr (triphenylmethyl or trityl), benzylidenyl, p-toluenesulfonyl, DMB (dimethoxybenzyl), PMB (p-methoxybenzyl), Boc (tert-butyloxycarbonyl), Fmoc (9-fluorenylmethyloxycarbonyl) or Cbz (carbobenzyloxy). In one such embodiment, each PG is the same. Where each PG is the same, in one such embodiment, each PG is PMB.

The organomagnesium compound can be, for example, a grignard reagent. In one embodiment, the organomagnesium compound is selected from the group consisting of isopropylmagnesium chloride, isopropylmagnesium bromide, isopropylmagnesium iodide, isopropylmagnesium chloride lithium chloride complex, sec-butylmagnesium chloride, lithium tri-n-butylmagnesiate, lithium triisopropylmagnesiate, and lithium (isopropyl)(di-n-butyl)magnesiate). In one embodiment, of the processes described herein the organomagnesium compound is i-PrMgCl·LiCl.

In the processes described herein, the Zn compound is selected from the group consisting of ZnCl$_2$, ZnBr$_2$, ZnI$_2$, Zn(TFA)$_2$, Zn(OAc)$_2$, and Zn(OPiv)$_2$, including LiCl or LiTFA salts thereof. In one embodiment, the Zn compound is ZnCl$_2$, ZnBr$_2$, or ZnI$_2$. In one embodiment, the Zn compound is ZnCl$_2$, ZnBr$_2$, or Zn(OPiv)$_2$. In one embodiment, the Zn compound is ZnCl$_2$ or Zn(OPiv)$_2$. In one embodiment, the Zn compound is ZnCl$_2$. In one embodiment, the Zn compound is ZnCl$_2$·LiCl. In one embodiment, the Zn compound is Zn(OPiv)$_2$. In one embodiment, the Zn compound is a salt and is Zn(OPiv)$_2$·LiCl.

In one embodiment, the transition metal catalyst precursor is a Pd or Ni catalyst precursor. In one embodiment, the transition metal catalyst precursor is a Pd or Ni catalyst precursor is selected from the group consisting of Pd(OAc)$_2$, PdCl$_2$, PdCl$_2$(MeCN)$_2$, Pd(benzonitrile)$_2$Cl$_2$, Pd(dba)$_2$, Pd$_2$(dba)$_3$, Pd(PPh$_3$)$_4$, Pd(PCy$_3$)$_2$, Pd(PtBu$_3$)$_2$, Pd(TFA)$_2$, [Pd(allyl)Cl]$_2$, [Pd(cinammyl)Cl]$_2$, [PdCl(crotyl)]$_2$, PdCl(η5-cyclopentadienyl), [(η3-allyl)(η5-cyclopentadienyl)palladium(II)], [Ni(η5-cyclopentadienyl)(allyl)], [bis(1,5-cyclooctadiene)nickel(0)], NiCl$_2$, NiBr$_2$, Ni(OAc)$_2$, and Nickel(II) acetylacetonate.

In one such embodiment of the process (P1) described herein, the Pd or Ni catalyst precursor is a Pd catalyst precursor. In one embodiment, the Pd catalyst precursor is Pd(OAc)$_2$, PdCl$_2$, PdCl$_2$(MeCN)$_2$, Pd(dba)$_2$, Pd$_2$(dba)$_3$, Pd(TFA)$_2$, [Pd(allyl)Cl]$_2$, [Pd(cinammyl)Cl]$_2$, [PdCl(crotyl)]$_2$, PdCl(η5-cyclopentadienyl), or [(η3-allyl)(η5-cyclopentadienyl)palladium(II)]. In another embodiment of the process (P1) described herein, the Pd catalyst precursor is Pd(OAc)$_2$, or PdCl$_2$. In another embodiment of the process (P1) described herein, the Pd catalyst precursor is [PdCl(crotyl)]$_2$, PdCl(η5-cyclopentadienyl), PdCl$_2$(MeCN)$_2$, Pd(dba)$_2$, Pd$_2$(dba)$_3$, or Pd(TFA)$_2$. In another embodiment of the process (P1) described herein, the Pd catalyst precursor is [Pd(allyl)Cl]$_2$, [Pd(cinammyl)Cl]$_2$, or (η3-allyl)(η5-cyclopentadienyl)palladium(II). In one embodiment, the Pd catalyst precursor is [Pd(allyl)Cl]$_2$ or [Pd(cinammyl)Cl]$_2$. In one embodiment, the Pd catalyst precursor is [Pd(cinammyl)Cl]$_2$.

In another embodiment of the process (P1) described herein, the Pd or Ni catalyst precursor is a Ni catalyst precursor. In one embodiment, the Ni catalyst precursor is NiCp(allyl), bis(1,5-cyclooctadiene)nickel(0), NiCl$_2$, NiBr$_2$, Ni(OAc)$_2$, or Nickel(II) acetylacetonate. In one embodiment, the Ni catalyst precursor is NiCl$_2$, NiBr$_2$, or Ni(OAc)$_2$. In another embodiment, the Ni catalyst precursor is NiCp(allyl), bis(1,5-cyclooctadiene)nickel(0), or Nickel(II) acetylacetonate.

In one embodiment of the process (P1) described herein, a Pd precursor described herein and a chiral ligand described herein are contacted to form a Pd-ligand complex in situ. In another embodiment, a Pd precursor described herein is treated with a chiral ligand described herein to form a Pd-ligand complex that can be isolated before use in a process described herein. In one embodiment, the Pd catalyst precursor is [Pd(cinammyl)Cl]$_2$ and the zinc compound is ZnCl$_2$ or Zn(OPiv)$_2$.

In one embodiment, the chiral ligand is a compound of formula:

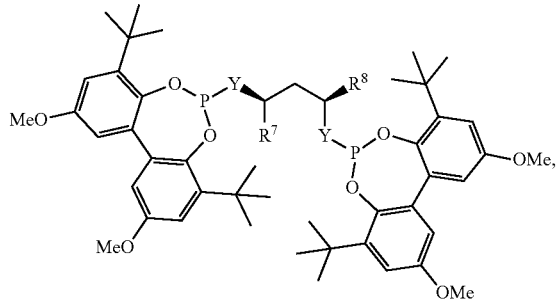

(L1)

wherein
Y is O or NR$^7$; and
R$^7$ and R$^8$ are independently unsubstituted C$_{1-6}$ alkyl.

In one embodiment of the compound of formula L1, R$^7$ and R$^8$ are the same. In one such embodiment, R$^7$ and R$^8$ are each independently methyl, ethyl, or phenyl. In one embodiment, R$^7$ and R$^8$ are each methyl (e.g. (R,R)-chiraphite). In one embodiment, R$^7$ and R$^8$ are each ethyl. In one embodiment of the processes described herein, the chiral ligand is (R,R)-chiraphite.

In one embodiment of the process (P1) described herein, step (a) is performed using pre-cooled solutions respectively comprising the compound of formula (II) as described herein and the organomagnesium compound as described herein. In one such embodiment, the pre-cooled temperature is about: −30° C. to about 20° C.; −30° C. to about 15° C.; −30° C. to about 10° C.; −30° C. to about 5° C.; −30° C. to about 0° C.; −25° C. to about 20° C.; −25° C. to about 15° C.; −25° C. to about 10° C.; −25° C. to about 5° C.; −25° C. to about 0° C.; −20° C. to about 20° C.; −20° C. to about 15° C.; −20° C. to about 10° C.; −20° C. to about 5° C.; or −20° C. to about 0° C. In one embodiment, the compound of formula (IIb) is isolated (and optionally stored) prior to step (b). In one such embodiment, the compound of formula (IIa) is stable for at least 1, 2, 3, 4, 5, or 6 weeks.

In one embodiment, the organomagnesium compound as described herein is present at a molar equivalent of about 0.9-1.50; 0.9-1.45; 0.9-1.40; 0.9-1.35; 0.9-1.30; 0.9-1.25; 0.9-1.20; 0.9-1.15; 0.9-1.10; 0.9-1.05; 0.9-1.02; 0.9-1.00; 0.95-1.50; 0.95-1.45; 0.95-1.40; 0.95-1.35; 0.95-1.30; 0.95-

1.25; 0.95-1.20; 0.95-1.15; 0.95-1.10; 0.95-1.08; 0.95-1.05; 0.95-1.03; 0.95-1.02; 0.95-1.01; 0.95-1.00; 1.00-1.15; 1.00-1.12; 1.00-1.11; 1.00-1.10; 1.00-1.09; 1.00-1.08; 1.00-1.07; 1.00-1.06; 1.00-1.05; 1.00-1.03; or 1.00-1.02 relative to the compound of formula (II) in step (a) of process (P1).

In one embodiment of the process (P1) described herein, step (b) is performed at a temperature of about: −30° C. to about 20° C.; −30° C. to about 15° C.; −30° C. to about 10° C.; −30° C. to about 5° C.; −30° C. to about 0° C.; −25° C. to about 20° C.; −25° C. to about 15° C.; −25° C. to about 10° C.; −25° C. to about 5° C.; −25° C. to about 0° C.; −20° C. to about 20° C.; −20° C. to about 15° C.; −20° C. to about 10° C.; −20° C. to about 5° C.; or −20° C. to about 0° C. In one embodiment of the process (P1) described herein, step (b) is performed at a temperature of about: −30° C., −25° C., −20° C., −15° C., −10° C., −5° C., 0° C., 5° C., or 10° C. In one such embodiment, step (b) is performed at a temperature of about −5° C., 0° C. or 5° C.

In one embodiment, the Zn compound as described herein is present at a molar equivalent of about 0.3-1.50, 0.3-1.45, 0.3-1.40, 0.3-1.35, 0.3-1.30; 0.3-1.25; 0.3-1.20; 0.3-1.15; 0.3-1.10; 0.3-1.05; 0.3-1.02; 0.3-1.00; 0.3-0.95, 0.3-0.90, 0.3-0.8, 0.3-0.75, or 0.3-0.6 relative to the compound of formula (IIa) in step (a) of process (P1). In one embodiment, the Zn compound as described herein is present at a molar equivalent of about 0.4-1.50, 0.4-1.45, 0.4-1.40, 0.4-1.35; 0.4-1.30; 0.4-1.25; 0.4-1.20; 0.4-1.15; 0.4-1.10; 0.4-1.05; 0.4-1.02; 0.4-1.00; 0.4-0.95, or 0.4-0.90 relative to the compound of formula (IIa) in step (a) of process (P1).

In one embodiment, the Zn compound as described herein is present at a molar equivalent of about 0.6-1.75, 0.6-1.70, 0.6-1.65, 0.6-1.60, 0.6-1.55, 0.6-1.50, 0.6-1.45, 0.6-1.40, 0.6-1.35; 0.6-1.30; 0.6-1.25; 0.6-1.20; 0.6-1.15; 0.6-1.10; 0.6-1.05; 0.6-1.02; 0.6-1.00; 0.6-0.95, or 0.6-0.90 relative to the compound of formula (IIa) in step (a) of process (P1). In one embodiment, the Zn compound as described herein is present at a molar equivalent of about 0.3-0.6, 0.6-0.9, or 0.9-1.5 relative to the compound of formula (IIa) in step (a) of process (P1). In one embodiment, the Zn compound as described herein is present at a molar equivalent of about 0.3-0.6 or 0.6-0.9 relative to the compound of formula (IIa) in step (a) of process (P1).

In one embodiment, the Zn compound as described herein is present at a molar equivalent of about 0.95-1.50; 0.95-1.45; 0.95-1.40; 0.95-1.35; 0.95-1.30; 0.95-1.25; 0.95-1.20; 0.95-1.15; 0.95-1.10; 0.95-1.08; 0.95-1.05; 0.95-1.03; 0.95-1.02; 0.95-1.01; 0.95-1.00; 1.00-1.15; 1.00-1.12; 1.00-1.11; 1.00-1.10; 1.00-1.09; 1.00-1.08; 1.00-1.07; 1.00-1.06; 1.00-1.05; 1.00-1.03; or 1.00-1.02 relative to the compound of formula (IIa) in step (a) of process (P1).

In one embodiment, the Zn compound as described herein is present at a molar equivalent of about 0.9-1.75, 0.9-1.70, 0.9-1.65, 0.9-1.60, 0.9-1.55, 0.9-1.50, 0.9-1.45, 0.9-1.40, 0.9-1.35; 0.9-1.30; 0.9-1.25; 0.9-1.20; 0.9-1.15; 0.9-1.10; 0.9-1.05; 0.9-1.02; 0.9-1.00; 0.95-1.50; 0.95-1.45; 0.95-1.40; 0.95-1.35; 0.95-1.30; 0.95-1.25; 0.95-1.20; 0.95-1.15; 0.95-1.10; 0.95-1.08; 0.95-1.05; 0.95-1.03; 0.95-1.02; 0.95-1.01; 0.95-1.00; 1.00-1.15; 1.00-1.12; 1.00-1.11; 1.00-1.10; 1.00-1.09; 1.00-1.08; 1.00-1.07; 1.00-1.06; 1.00-1.05; 1.00-1.03; or 1.00-1.02 relative to the compound of formula (IIa) in step (a) of process (P1). In one embodiment, the compound of formula (IIb) is stable in solution under inert conditions for at least 1, 2, 3, 4, 5, or 6 weeks.

In one embodiment, the compound of formula (III) as described herein is present at a molar equivalent of about 0.9-1.50; 0.9-1.45; 0.9-1.40; 0.9-1.35; 0.9-1.30; 0.9-1.25; 0.9-1.20; 0.9-1.15; 0.9-1.10; 0.9-1.05; 0.9-1.02; 0.9-1.00; 0.95-1.50; 0.95-1.45; 0.95-1.40; 0.95-1.35; 0.95-1.30; 0.95-1.25; 0.95-1.20; 0.95-1.15; 0.95-1.10; 0.95-1.08; 0.95-1.05; 0.95-1.03; 0.95-1.02; 0.95-1.01; 0.95-1.00; 1.00-1.15; 1.00-1.12; 1.00-1.11; 1.00-1.10; 1.00-1.09; 1.00-1.08; 1.00-1.07; 1.00-1.06; 1.00-1.05; 1.00-1.03; or 1.00-1.02 relative to the compound of formula (IIb) in step (c) of process (P1). In one embodiment, In one embodiment, the compound of formula (II) is prepared according to the process (P2):

(a) cyclizing a compound of formula (IV)

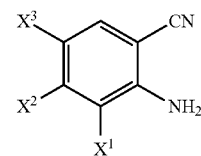

under $CO_2$ in the presence of a base to a compound of formula (V)

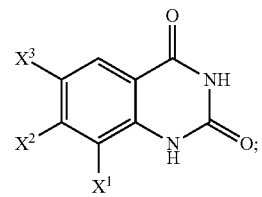

(b) contacting the compound of formula (V) with a chlorinating agent thereby synthesizing a compound of formula (Va)

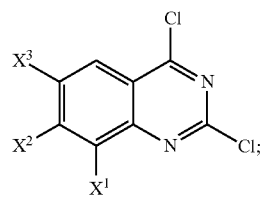

(c) contacting the compound of step (b) with a piperazinyl moiety having formula

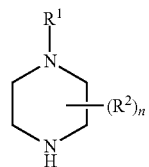

in the presence of a base, thereby synthesizing a compound of formula (Vb)

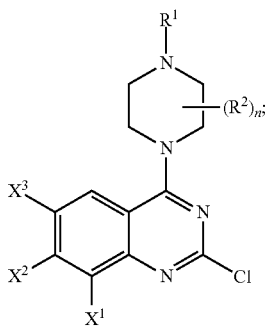

and
(d) contacting the compound of step (c) with a fluorinating agent in the presence of a base thereby synthesizing a compound of formula (II).

In one embodiment of the process (P2), the base is 1,8-diazabicyclo[5.4.0]undec-7-ene (DBU). In another embodiment, the base is DBN (1,5-Diazabicyclo[4.3.0]non-5-ene), MTBD (7-Methyl-1,5,7-triazabicyclo(4.4.0)dec-5-ene), or TBD (1,5,7-triazabicyclo(4.4.0)dec-5-ene). In another embodiment, the base is a carbonate bases, such as, $Na_2CO_3$, $K_2CO_3$, or $Cs_2CO_3$) where the solvent of the reaction is water, also work in water as solvent.

In one embodiment of the process (P2), the chlorinating agent of step (b) $POCl_3$, $PCl_3$, $PCl_5$, or $SOCl_2$. In one such embodiment, the chlorinating agent of step (b) is $POCl_3$.

In one embodiment of the process (P2), the base of step (c) is N-ethyl morpholine (NEM), triethylamine (TEA), tri(n-propyl)amine (TPA), N,N-diisopropylethylamine (DIPEA), N-methylmorpholine (NMM), N-methylimidazole (NMI), DBU, tri(n-butyl)amine, pyridine, 2,6-lutidine, or 2,4,6-collidine. In one embodiment, the base of step (c) is DIPEA. In one embodiment, the base of step (c) is N-ethyl morpholine (NEM), triethylamine (TEA), or tri(n-propyl) amine (TPA). In one embodiment, the base of step (c) is N-methylmorpholine (NMM), N-methylimidazole (NMI), DBU, or tri(n-butyl)amine. In one embodiment, the base of step (c) is pyridine, 2,6-lutidine, or 2,4,6-collidine.

In another embodiment (P2) the fluorinating agent of step (d) is KF. In another embodiment of the process (P2) the fluorinating agent of step (d) is CsF or NaF. In another embodiment of the process (P2) the base is DABCO (1,4-diazabicyclo[2.2.2]octane). In one such embodiment, DABCO is present at a catalyic amount. In another such embodiment, step (d) of the process (P2) further comprises MsOH as an additive.

Compound (IV) of the process (P2) can be synthesized according to process (P3) as described herein, where the compound of formula (IV) is prepared according to the process (P3) comprising:
(a) contacting a compound of formula (IVa)

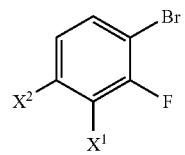

with i-PrMgCl thereby synthesizing a compound of formula (IVb)

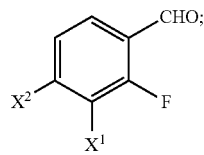

(b) contacting the compound of step (a) with hydroxylamine ($NH_2OH$) thereby synthesizing a compound of formula (IVc)

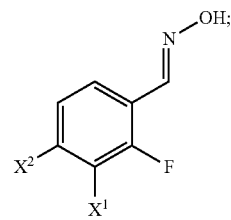

(c) contacting the compound of step (b) with a base and a dehydratization agent as described herein in acetonitrile thereby synthesizing a compound of formula (IVd)

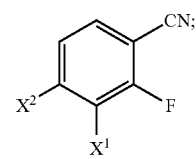

(d) contacting the compound of step (c) with ammonia thereby synthesizing a compound of formula (IVe)

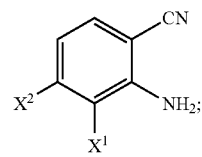

and
(e) contacting the compound of step (d) with a halogenating agent thereby synthesizing the compound of formula (IV). In one embodiment, the halogenating agent is a chlorinating agent and $X^3$ is Cl.

In one embodiment of the process (P3) the base of step (c) is a tertiary amine. In one embodiment, the base of step (c) is N-ethyl morpholine (NEM), triethylamine (TEA), tri(n-propyl)amine (TPA), N,N-diisopropylethylamine (DIPEA), N-methylmorpholine (NMM), N-methylimidazole (NMI), 1,8-diazabicyclo[5.4.0]undec-7-ene (DBU), or tri(n-butyl) amine. In one such embodiment, the base is triethylamine. In another embodiment of the process (P3) the base of step (c) is pyridine or DBU. In another embodiment of the process (P3) the base of step (c) is an inorganic base such as, for example, $K_2CO_3$, NaOAc, NaOH, or KOH could potentially be used as well In one embodiment of the process (P3) the dehydratization agent of step (c) is trifluoroacetic anhydride (TFAA), acetic anhydride (Ac2O), methanesulfonic anhydride (Ms2O), p-toluenesulfonic anhydride (Ts2O), trifluoromethanesulfonic anhydride (Tf2O), propanephosphonic anhydride (T3P), methanesulfonyl chloride (MsCl), toluenesulfonyl chloride (TsCl), SOCl$_2$, POCl$_3$, or carbonyl diimidiazole (CDI). In one such embodiment, the dehydratization agent is trifluoroacetic anhydride (TFAA) or acetic anhydride (Ac2O). In one such embodiment, the dehydratization agent of step (c) is trifluoroacetic anhydride (TFAA), acetic anhydride (Ac2O), methanesulfonic anhydride (Ms2O), p-toluenesulfonic anhydride (Ts2O), trifluoromethanesulfonic anhydride (Tf2O), or propanephosphonic anhydride (T3P). In another such embodiment, the dehydratization agent of step (c) is trifluoroacetic anhydride (TFAA), acetic anhydride (Ac2O), or trifluoromethanesulfonic anhydride (Tf2O). In another such embodiment, the dehydratization agent is trifluoroacetic anhydride (TFAA).

In one embodiment of the process (P3) the halogenating agent of step (e) is 1,3-Dichloro-5,5-dimethylhydantoin (DCDMH or DCH), SO$_2$Cl$_2$, TCCA (trichloroisocyanuric acid), N-chlorosaccharin, or N-chlorosuccinimide (NCS). In one such embodiment, the halogenating agent is NCS. In one embodiment of the process (P3) step (e) further comprises a substoichiometric amound of acid. In one such embodiment, the acid is HCl.

In one embodiment of the process (P1), the compound of formula (III) is prepared according to the process (P4);
(a) contacting a compound of formula (VIa)

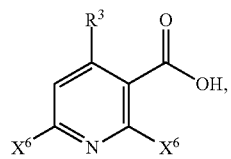

wherein $X^6$ is Cl or I, with a halogenating agent to form a compound of formula (VIb)

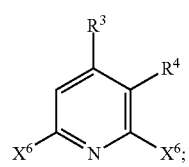

(b) brominating the compound of formula (VIb) to form a compound of formula (VI)

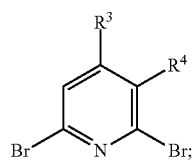

and
(c) contacting the compound of formula (VI) with a compound having formula NH(PG)$_2$ thereby making a compound of formula (III).

In one embodiment of the process (P4), each $X^6$ is the same. In one embodiment of the process (P4), each $X^6$ is Cl. In one embodiment of the process (P4), the halogenating agent of step (a) is SF$_4$ in HF.

In one embodiment of the process (P4), the bromination of step (b) is performed using HBr in an acid. In one such embodiment, the acid is acetic acid. In another such embodiment, the acid is trifluoroacetic acid.

In one embodiment of the processes described herein, the compound of formula (III) has formula:

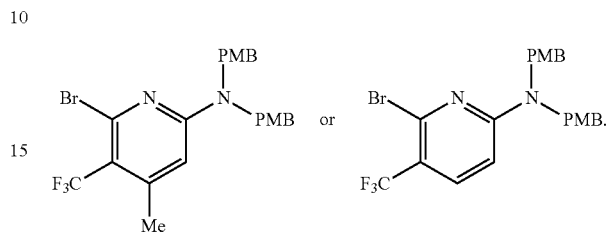

In one such embodiment, the compound of formula (III) has formula:

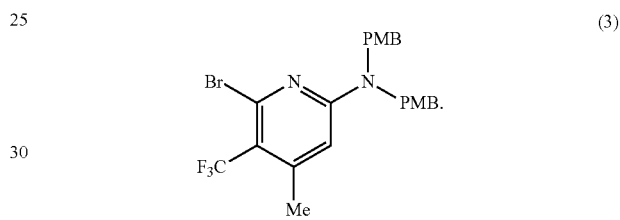

(3)

Compound (3) can be synthesized according to the processes described herein (e.g. process (P4)).

In one such embodiment of the process (P1), the compound of formula (III) has formula (3) and wherein the compound of formula (3) is synthesized according a process (P6) comprising:
(a) contacting a compound of formula (6a)

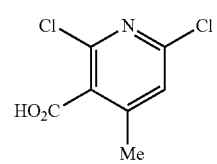 [SMILES: Cc1cc(Cl)nc(Cl)c1C(=O)O]

with SF$_4$ and HF thereby synthesizing a compound of formula (6b)

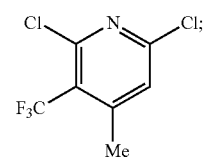 [SMILES: Cc1cc(Cl)nc(Cl)c1C(F)(F)F]

(b) contacting the compound of formula (6b) with HBr in AcOH to form a compound of formula (6)

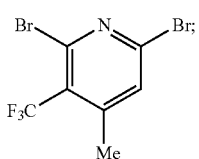

(c) contacting the compound of formula (6) with NH(PMB)$_2$, triethylamine, and N-butylpyrrolidinone (NBP), thereby synthesizing the compound of formula (3).

In one embodiment, the compound of formula (I) has formula:

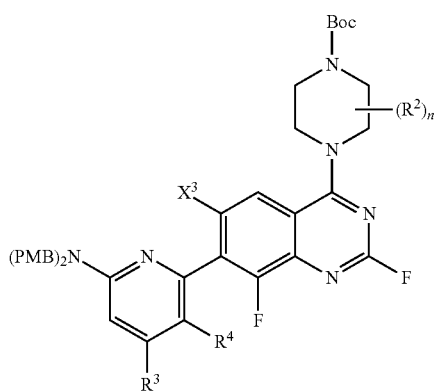

(Ia)

or

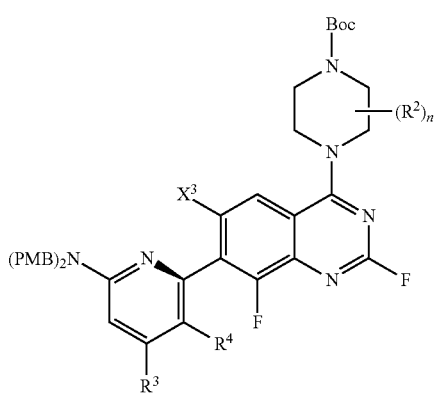

(Ib)

or

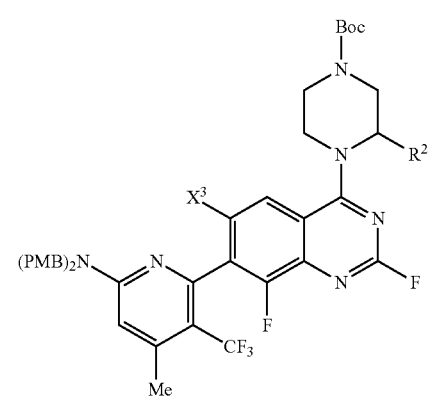

(Ic)

or

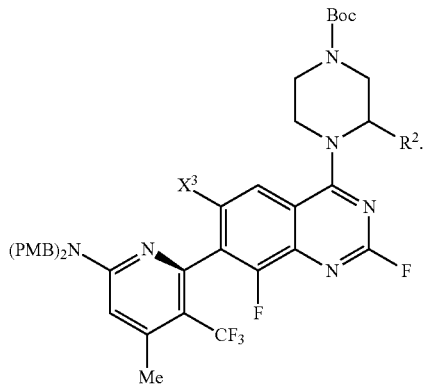

(Id)

In one embodiment of the compound of formula (Ia), (Ib), (Ic), and (Id), R$^2$ is methyl. In one embodiment of the compound of formula (Ia), (Ib), (Ic), and (Id), X$^3$ is halo. In one such embodiment, X$^3$ is Cl.

In one embodiment, the compound of formula (I) has formula:

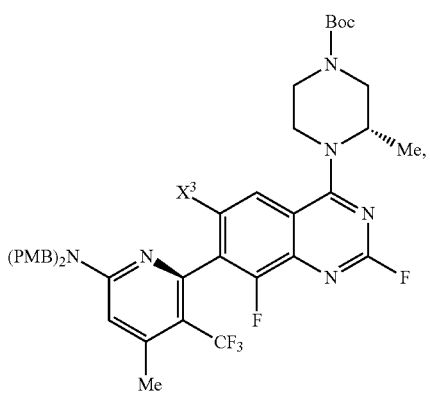

(Ie)

wherein X$^3$ is halo.

In one embodiment, the compound of formula (I) has formula:

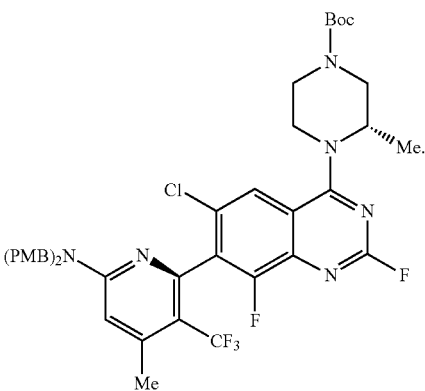

(11)

Further provided herein are processes for the synthesis of a compound of formula (2):

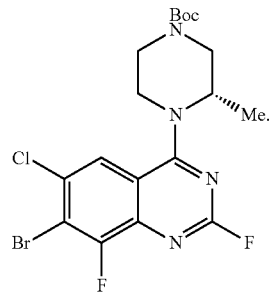
(2)

In one embodiment is a process (P5) for the synthesis of a compound of formula (2), the process comprising the steps:
(a) contacting a compound of formula (4a)

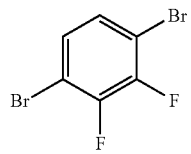

with i-PrMgCl followed by hydroxylamine (NH$_2$OH), thereby synthesizing the compound of formula (4c)

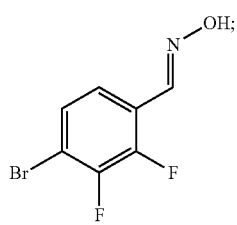 [SMILES: O/N=C/c1ccc(Br)c(F)c1F]

(b) contacting the compound of formula (4c) with TFAA and triethylamine in acetonitrile followed by ammonia, thereby synthesizing the compound of formula (4e)

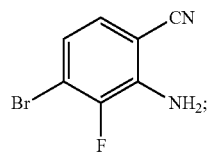 [SMILES: N#Cc1ccc(Br)c(F)c1N]

(c) contacting the compound of (4e) with a chlorinating agent, thereby synthesizing the compound of formula (4)

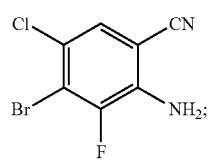 [SMILES: N#Cc1cc(Cl)c(Br)c(F)c1N]

(d) contacting the compound of (4) with CO$_2$ in the presence of 1,8-diazabicyclo[5.4.0]undec-7-ene (DBU), thereby synthesizing the compound of formula (5)

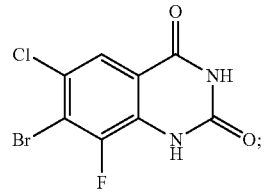

(e) contacting the compound of formula (5) with POCl$_3$ and DIPEA followed by tert-butyl (S)-3-methylpiperazine-1-carboxylate and DIPEA, thereby synthesizing the compound of formula (5b)

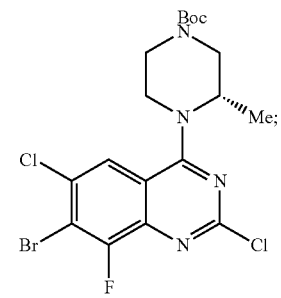 [SMILES: C[C@H]1CN(C(=O)OC(C)(C)C)CCN1c1nc(Cl)nc2c(F)c(Br)c(Cl)cc12]

and
(f) contacting the compound of (5b) with KF, 1,4-diazabicyclo[2.2.2]octane (DABCO), and MsOH, thereby forming the compound of formula (2).

In one embodiment, step (a) of the process (P5) is performed in DMF as a solvent.

In another embodiment, the process (P1) further comprises synthesizing a compound of formula (G) according to the process (P7):

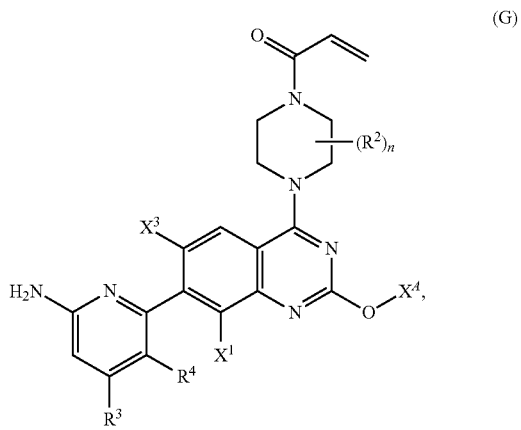
(G)

or a tautomer, stereoisomer, atropisomer, or pharmaceutically acceptable salt thereof, wherein;
X$^A$ is selected from the group consisting of

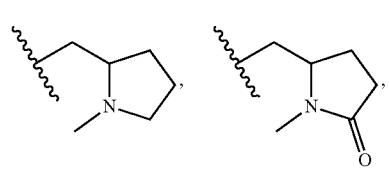

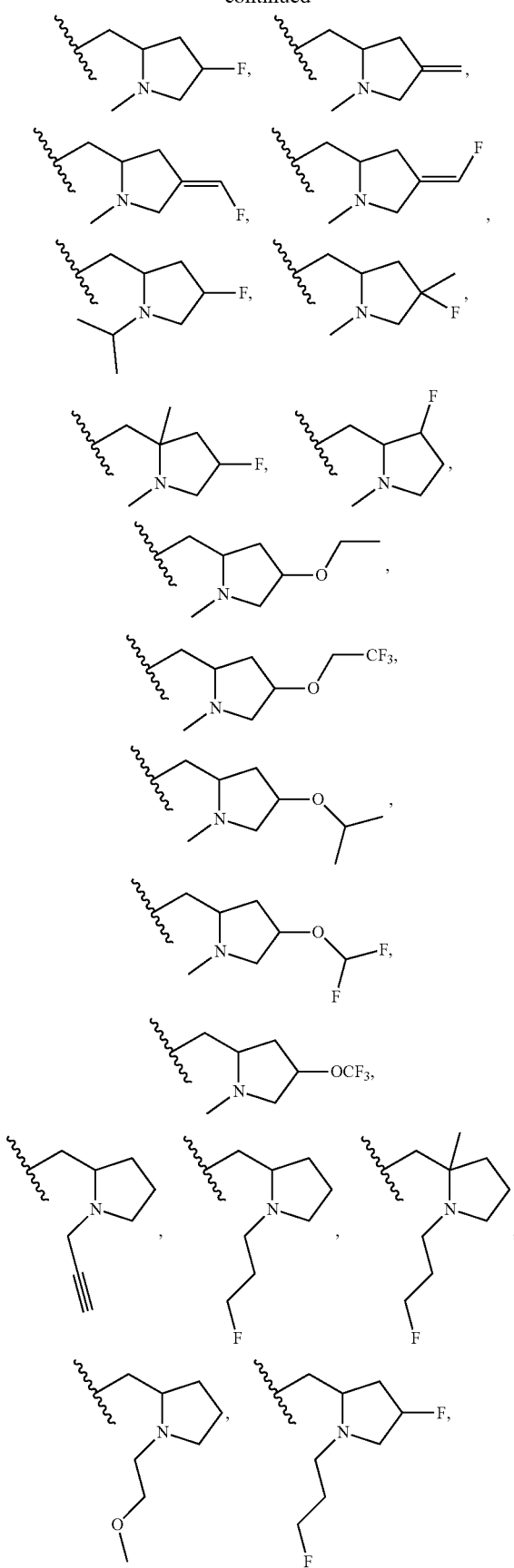
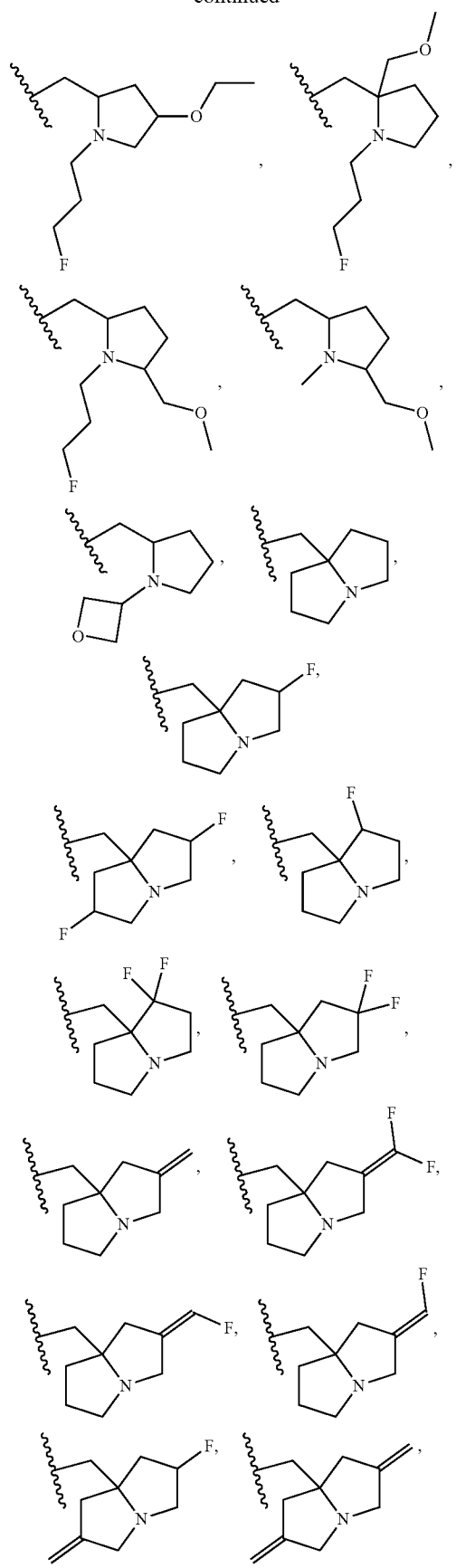

-continued

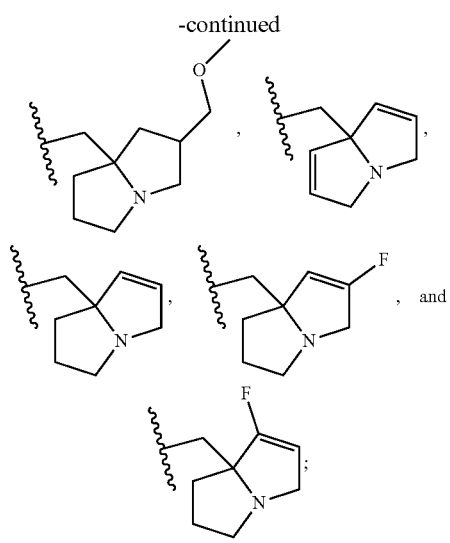

the process comprising:
(a) contacting the compound of formula (I) or a solvate, tautomer, stereoisomer, atropisomer, or salt thereof synthesized as described herein with a moiety comprising $X^A$ in the presence of base and an activating agent, thereby synthesizing a compound of formula (G1);

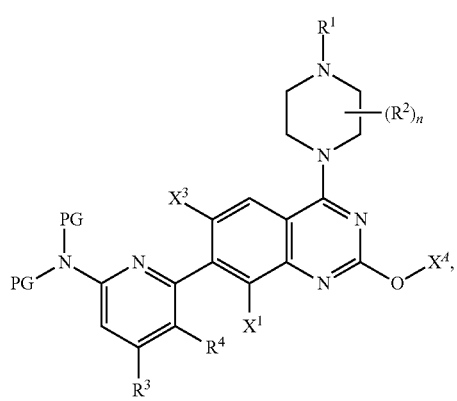
(G1)

(b) removing the PG groups and optionally $R^1$ from the compound of formula (G1); and
(c) contacting the compound of step (b) with a compound of formula (VII)

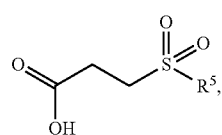

where $R^5$ is unsubstituted $C_{1-6}$alkyl or phenyl, in the presence of a an activating agent, followed by contacting with a base, thereby making a compound of formula (G) or a tautomer, stereoisomer, atropisomer, or pharmaceutically acceptable salt thereof. In one embodiment, $R^5$ is phenyl. In one embodiment, $R^5$ is methyl, ethyl, propyl, or t-butyl.

In one embodiment, the compound of formula (VII) has formula:

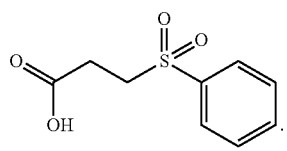
(7)

In one embodiment, the $X^A$ is

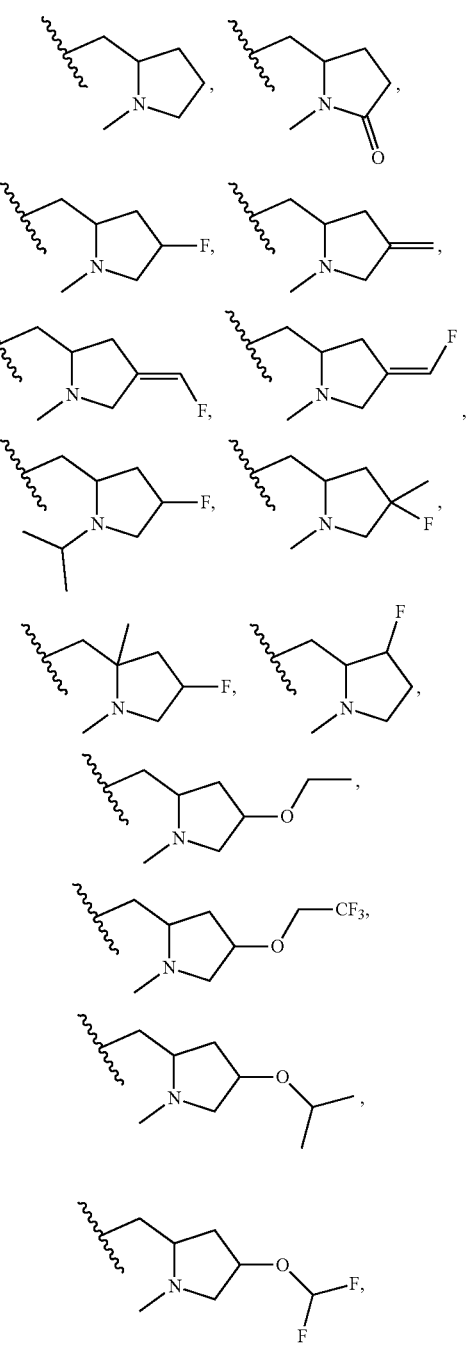

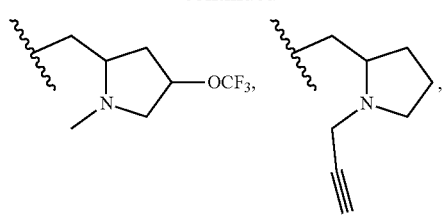
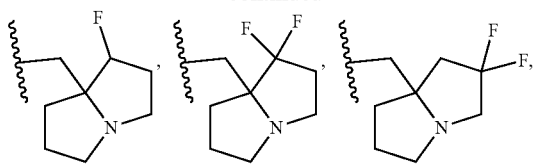
In one embodiment, $X^A$ is
In one such embodiment, $X^A$ is
In one embodiment, $X^A$ is

Further provided herein is a process (P8) for the synthesis of a compound of formula (1):

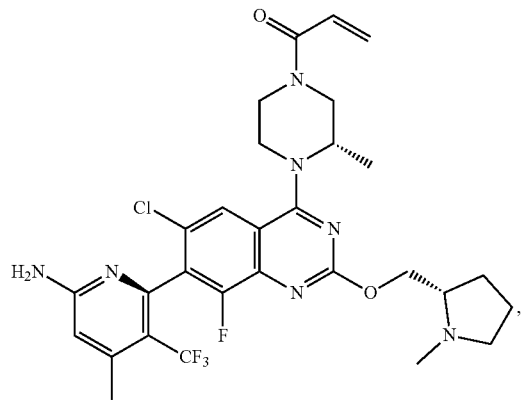

(1)

or a pharmaceutically acceptable salt thereof, the process comprising:
(a) contacting a precooled solution comprising a compound of formula (2)

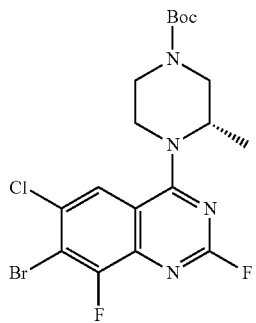

or a salt thereof with a pre-cooled solution comprising i-PrMgCl·LiCl using a flow rate resulting in a residence time of about 15-150 seconds for the Mg—Br exchange thereby synthesizing a compound of formula (2a);

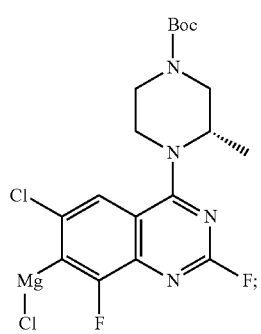

(2a)

(b) transferring the compound of formula (2a) of step (a) to a continuous stirred tank reactor (CSTR) comprising a precooled solution of $ZnCl_2$ or $Zn(OPiv)_2$ and maintaining a constant residence time of about 3-7 minutes at about −20° C. to 20° C. thereby synthesizing a compound of formula (2b);

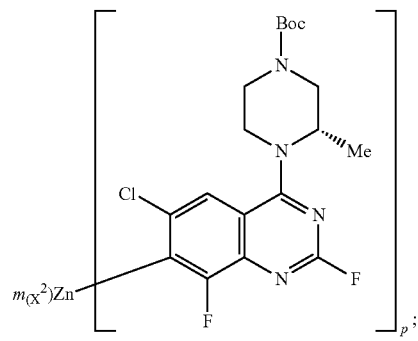

(2b)

(c) contacting the compound of formula (2b) with NaTFA and a compound of formula (3)

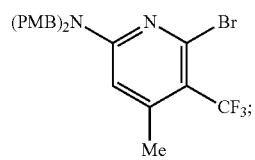

(d) contacting the mixture of step (c) or a salt thereof with a Pd or Ni catalyst precursor and a chiral ligand thereby synthesizing a compound of formula (11);

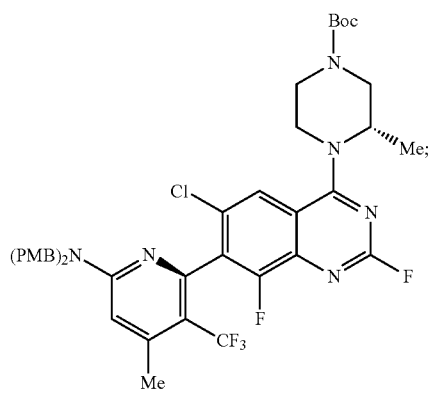

(11)

or a solvate or salt thereof,
(e) contacting the compound of formula (11) or a solvate or salt thereof, with a compound of formula HO—$X^A$, wherein $X^A$ has formula

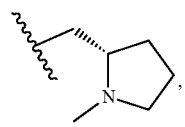 [SMILES: *C[C@@H]1CCCN1C]

and a base thereby synthesizing a compound of formula (1b);

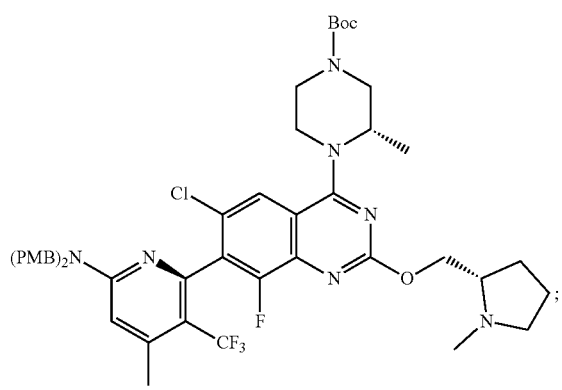

(1b)

or a solvate or pharmaceutically acceptable salt thereof;
(f) contacting the compound of formula (1 b) with MsOH in an acid thereby synthesizing a compound of formula (1a);

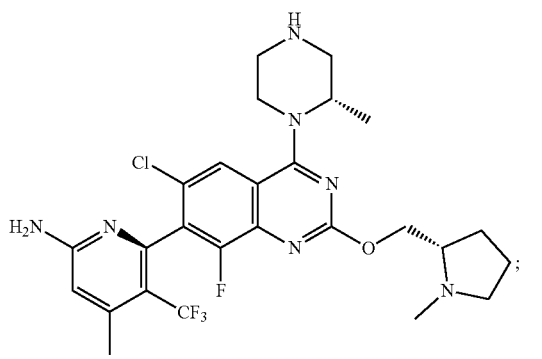

(1a)

or a solvate or pharmaceutically acceptable salt thereof; and
(g) contacting the compound of formula (Ia) or a solvate or pharmaceutically acceptable salt thereof with

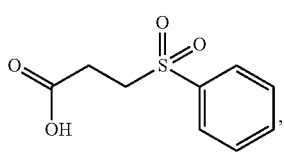 [SMILES: O=C(O)CCS(=O)(=O)c1ccccc1]

in the presence of an activating agent, followed by contacting with a base, thereby making a compound of formula (1) or a pharmaceutically acceptable salt thereof.

In one embodiment, the residence time of step (a) of process (P8) is about: 15-45 seconds, 15-60 seconds, 15-90 seconds, 15-100 seconds, or 15-120 seconds. In one embodiment, the residence time of step (a) of process (P8) is about: 30-45 seconds, 30-60 seconds, 30-90 seconds, 30-120 seconds or 30-150 seconds. In still another embodiment, the residence time of step (a) of process (P8) is about: 15-45 seconds or 60-90 seconds. In one embodiment, the residence time of step (a) of process (P8) is about 15-45 seconds. In one embodiment, the residence time of step (a) of process (P8) is about 60-90 seconds. In one embodiment, the residence time of step (a) of process (P8) is about 60-150 seconds. In one embodiment, the residence time of step (a) of process (P8) is about 90-150 seconds.

In one embodiment of the process of (P8), the precooled solution of $ZnCl_2$ or $Zn(OPiv)_2$ further comprises LiCl. In one such embodiment, the precooled solution comprises $Zn(OPiv)_2 \cdot LiCl$.

In one embodiment of the process of (P8), compound 2b is as described herein. In one such embodiment, p is 1, m is 1, and $X^2$ is halogen (e.g. Cl or Br). In another such embodiment, compound 2b is a mixture where one or more of $X^2$, m, and p are different. In one embodiment, compound 2b comprises at least 2 or 3 different species. In one such embodiment, the number of species is dependent upon the number of equivalents of the zinc compound used. In one such embodiment, a greater number of equivalents of zinc compound compared to compound 2a results in a greater number of species. In such embodiments, the species can interconvert without effect on kinetics of the next reaction. In one embodiment, the species comprises $X^2$ as Br only where m is 1.

In one embodiment, the compound of formula (2) is prepared according to the process (P5) as described herein. In one embodiment, the compound of formula (3) is prepared according to the process (P6).

Further provided herein is a process (P9) for the synthesis of a compound of formula (1):

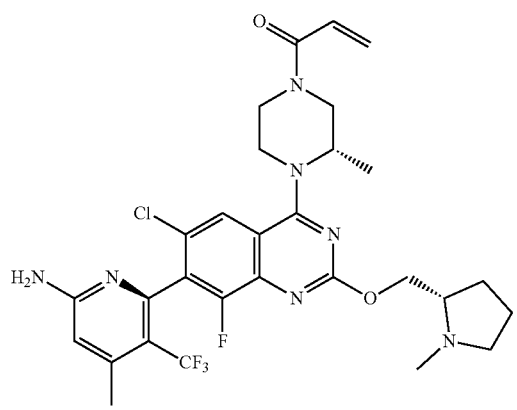

(1)

or a pharmaceutically acceptable salt thereof, the process comprising:
(a) contacting a precooled solution comprising a compound of formula (2)

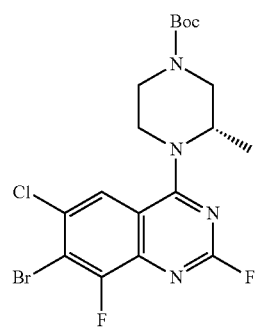 [SMILES: C[C@H]1CN(C(=O)OC(C)(C)C)CCN1c1nc(F)nc2c(F)c(Br)c(Cl)cc12]

or a salt thereof with a pre-cooled solution comprising i-PrMgCl·LiCl using a flow rate resulting in a residence time of about 15-150 seconds for the Mg—Br exchange;
(b) transferring the mixture of step (a) to a continuous stirred tank reactor (CSTR) comprising a precooled solution of ZnCl₂ or Zn(OPiv)₂ and maintaining a constant residence time of about 3-7 minutes at about −20° C. to 20° C.;
(c) contacting the mixture of step (b) with NaTFA and a compound of formula (3)

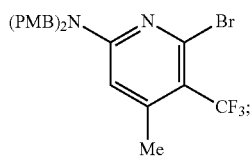

(d) contacting the mixture of step (c) or a salt thereof with a Pd or Ni catalyst precursor and a chiral ligand thereby synthesizing a compound of formula (11);

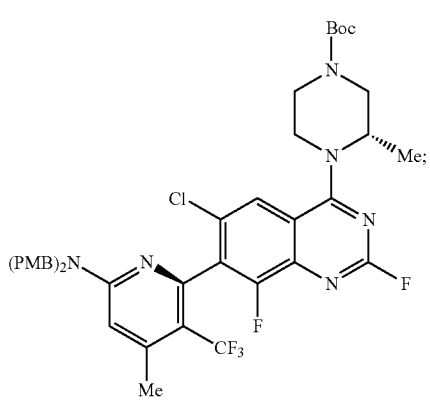

or a solvate or salt thereof,
(e) contacting the compound of formula (11) or a solvate or salt thereof, with a compound of formula HO—X⁴, wherein X⁴ has formula

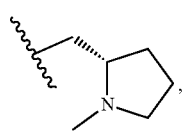 [SMILES: *C[C@@H]1CCCN1C]

and a base thereby synthesizing a compound of formula (1b);

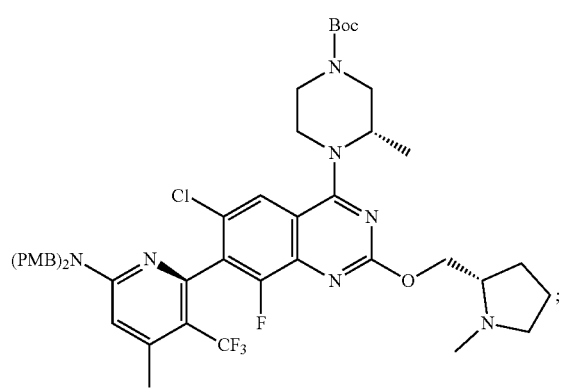

or a solvate or pharmaceutically acceptable salt thereof;

(f) contacting the compound of formula (1b) with MsOH in an acid thereby synthesizing a compound of formula (1a);

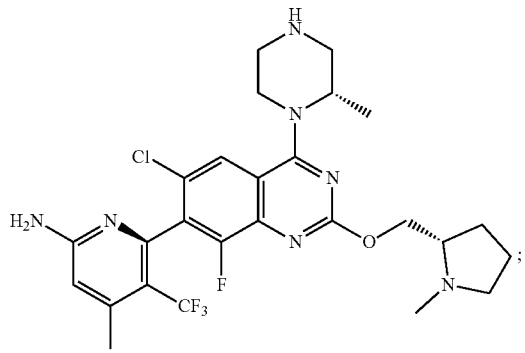

or a solvate or pharmaceutically acceptable salt thereof; and
(g) contacting the compound of formula (Ia) or a solvate or pharmaceutically acceptable salt thereof with

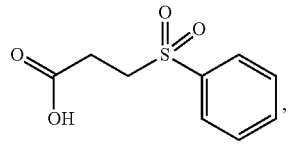 [SMILES: O=C(O)CCS(=O)(=O)c1ccccc1]

in the presence of an activating agent, followed by contacting with a base, thereby making a compound of formula (1) or a pharmaceutically acceptable salt thereof.

In one embodiment, the residence time of step (a) of process (P9) is about: 15-45 seconds, 15-60 seconds, 15-90 seconds, 15-100 seconds, or 15-120 seconds. In one embodiment, the residence time of step (a) of process (P9) is about: 30-45 seconds, 30-60 seconds, 30-90 seconds, 30-120 seconds or 30-150 seconds. In still another embodiment, the residence time of step (a) of process (P9) is about: 15-45 seconds or 60-90 seconds. In one embodiment, the residence time of step (a) of process (P9) is about 15-45 seconds. In one embodiment, the residence time of step (a) of process (P9) is about 60-90 seconds. In one embodiment, the residence time of step (a) of process (P9) is about 60-150 seconds. In one embodiment, the residence time of step (a) of process (P9) is about 90-150 seconds.

In one embodiment of the process of (P9), the precooled solution of ZnCl₂ or Zn(OPiv)₂ further comprises LiCl. In one such embodiment, the precooled solution comprises Zn(OPiv)₂·LiCl. In one such embodiment, the precooled solution comprises Zn(OPiv)₂·LiCl and the residence time of step (a) of process (P9) is about 60-90 seconds or about 60-150 seconds.

In one embodiment, the compound of formula (2) is prepared according to the process (P5) as described herein. In one embodiment, the compound of formula (3) is prepared according to the process (P6).

"Continuous flow" is used herein refers to a chemical reaction that is run in a continuously flowing stream rather than in batch production. In such instances, pumps move fluid into a flow system, wherein the fluids contact one another and a reaction occurs. In some embodiments, microreactors are used. In some embodiments, tubular or plug flow reactors (PFR) are used. In some other embodiments, continuous stirred tank reactors (CSTR) are used. In such embodiments, the reactors can be cooled prior to the transfer of agents or reactions therein. The continuous flow reactions described herein removes the need for low temperatures (e.g. −78° C.) typically used for such reactions. Such removal of the need for low temperatures increases reaction efficiency and allows for more robust scale up to commercial scale amounts of product. Furthermore, the continuous flow reactions described herein improve process robustness and controllability of the conditions of the reaction. The processes described herein result in better purity of the intermediates and compounds synthesized and reduce times needed for reactions and compound (1) production.

Methods of Treating Cancer

Compound 1 or a pharmaceutically acceptable salt thereof can be administered to the patient in an effective amount (e.g. an amount as described herein) for treating cancer mediated by a KRas$^{G12C}$ mutation. In one such embodiment, the cancer is a solid tumor (e.g. lung cancer, CRC, or pancreatic cancer). It is to be understood that the methods described herein also include treatment with a pharmaceutical composition as described herein comprising Compound 1 or a pharmaceutically acceptable salt thereof as described herein.

In one embodiment is a method of treating lung cancer mediated by a KRas$^{G12C}$ mutation in a patient having such a cancer, the method comprising administering an effective amount of Compound 1 or a pharmaceutically acceptable salt thereof to the patient having cancer.

In such embodiments, the lung cancer is non-small cell lung cancer (NSCLC) comprising KRas$^{G12C}$ mutations. In another embodiment, the lung cancer is adenocarcinoma, squamous-cell lung carcinoma or large-cell lung carcinoma. In one such embodiment, the cancer is lung adenocarcinoma. In another such embodiment, the lung cancer is a small cell lung carcinoma. In another embodiment, the lung cancer is small cell lung carcinoma. In still another embodiment, the lung cancer is glandular tumors, carcinoid tumors or undifferentiated carcinomas. The lung cancer can be stage I or II lung cancer. In one embodiment, the lung cancer is stage III or IV lung cancer.

Further provided herein is the use (UL1) of Compound 1 or a pharmaceutically acceptable salt thereof for the treatment of lung cancer as described herein.

Also provided herein is a method of treating colorectal cancer mediated by a KRas$^{G12C}$ mutation in a patient having such a cancer, the method comprising administering an effective amount of Compound 1 or a pharmaceutically acceptable salt thereof to the patient having cancer.

Further provided herein is the use (UC1) of Compound 1 or a pharmaceutically acceptable salt thereof as described herein for the treatment of colorectal cancer as described herein.

Further provided herein is a method of treating pancreatic cancer mediated by a KRas$^{G12C}$ mutation in a patient having such a cancer, the method comprising administering an effective amount of Compound 1 or a pharmaceutically acceptable salt thereof as described herein to the patient having cancer.

Further provided herein is the use (UP1) of Compound 1 or a pharmaceutically acceptable salt thereof as described herein for the treatment of pancreatic cancer as described herein.

Further provided herein are methods of treating tumor agnostic cancer comprising a KRas$^{G12C}$ mutation in a patient having such a cancer. In one such embodiment, the method comprising treating tumor agnostic cancer comprising a KRas$^{G12C}$ mutation in a patient having such a cancer by
  (a) determining the absence or presence of a KRas$^{G12C}$ mutation in a sample taken from a patient with a suspected diagnosed cancer; and
  (b) administering to the patient an effective amount of Compound 1 or a pharmaceutically acceptable salt thereof as described herein.

Further provided herein is the use (UA1) of Compound 1 or a pharmaceutically acceptable salt thereof as described herein for the treatment of tumor agnostic cancer as described herein.

In one embodiment of the methods and uses described herein, Compound 1 or a pharmaceutically acceptable salt thereof is administered as a fixed dose QD administration. In one embodiment, the administration is oral (PO), where Compound 1 or a pharmaceutically acceptable salt thereof is formulated as a tablet or capsule. In one embodiment, Compound 1 or a pharmaceutically acceptable salt thereof is administered at an amount of 5 mg-600 mg, 5 mg-500 mg, 5 mg-400 mg, 5 mg-300 mg, 5 mg-250 mg, 5 mg-200 mg, 5 mg-150 mg, 5 mg-100 mg, 5 mg-50 mg, 5 mg-25 mg, 25 mg-600 mg, 25 mg-500 mg, 25 mg-400 mg, 25 mg-300 mg, 25 mg-250 mg, 25 mg-200 mg, 25 mg-150 mg, 25 mg-100 mg, 25 mg-50 mg, 50 mg-600 mg, 50 mg-500 mg, 50 mg-400 mg, 50 mg-300 mg, 50 mg-250 mg, 50 mg-200 mg, 50 mg-150 mg, or 50 mg-100 mg QD. In another embodiment, Compound 1 or a pharmaceutically acceptable salt thereof is administered at an amount of about 5 mg, 25 mg, 50 mg, 100 mg, 150 mg, 200 mg, 250 mg, 300 mg, 400 mg or 500 mg.

EMBODIMENTS

Provided below are some exemplary embodiments of the invention.

Embodiment 1. A process for the synthesis of a compound of formula (I);

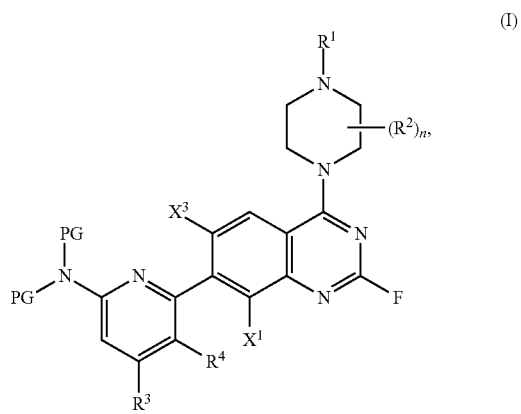

or a solvate, tautomer, stereoisomer, atropisomer, or salt thereof, wherein
  $X^1$ and $X^3$ are each independently hydrogen or halogen;
  $R^1$ is hydrogen or $PG^1$;
  each $R^2$ is independently halogen, cyano, unsubstituted $C_{1-6}$ alkyl, unsubstituted $C_{1-6}$ cyanoalkyl, or unsubstituted $C_{1-6}$ haloalkyl;

$R^3$ is hydrogen, halogen, $R^{3A}$-substituted or unsubstituted $C_{1-3}$ alkyl, $R^{3A}$-substituted or unsubstituted $C_{1-3}$ haloalkyl, or $R^{3A}$-substituted or unsubstituted cyclopropyl;
$R^{3A}$ is halogen, OH, CN, unsubstituted $C_{1-3}$ alkyl or unsubstituted $C_{1-3}$ haloalkyl;
$R^4$ is $R^{4A}$-substituted or unsubstituted $C_{1-3}$ haloalkyl;
$R^{4A}$ is unsubstituted $C_{1-3}$ alkyl;
n is 1 or 2;
each PG is independently an amino protecting group; and
$PG^1$ is an amino protecting group;
wherein the process comprises
(a) contacting a compound of formula (II)

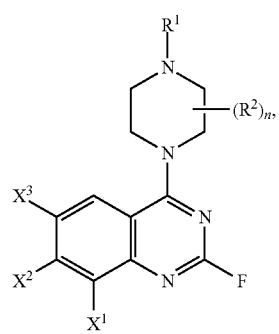
(II)

wherein $X^2$ is halogen;
with an organomagnesium compound thereby forming a compound of formula (IIa):

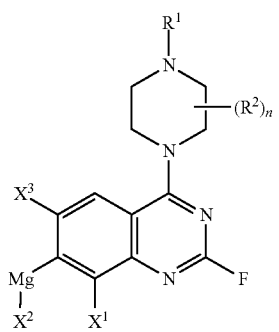
(IIa)

(b) transferring the compound of formula (IIa) of step (a) to a continuous stirred tank reactor (CSTR) comprising a zinc compound thereby synthesizing a compound of formula (IIb); and

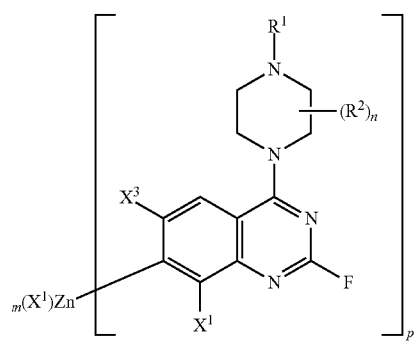
(IIb)

wherein m is 0, 1, or 2;
p is 1, 2, or 3; and
$X^2$ is halogen or OPiv;
(c) contacting the compound (IIb) of step (b) with a compound of formula (III),

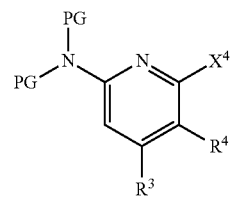
(III)

wherein $X^4$ is halogen,
a transition metal catalyst precursor, and a chiral ligand, thereby synthesizing a compound of formula (I).

Embodiment 2. The process of embodiment 1, wherein $X^2$ is Br, Cl, or OPiv.

Embodiment 3. The process of embodiment 1 or 2, wherein the compound of formula (II) is prepared according to the process (P2):
(a) cyclizing a compound of formula (IV)

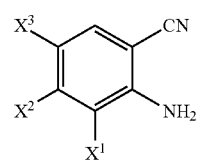

under $CO_2$ in the presence of a base to a compound of formula (V)

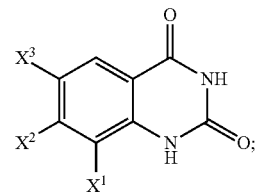

(b) contacting the compound of formula (V) with a chlorinating agent thereby synthesizing a compound of formula (Va)

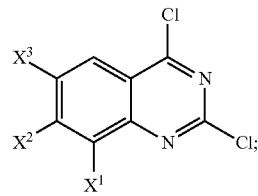

(c) contacting the compound of step (b) with a piperazinyl moiety having formula

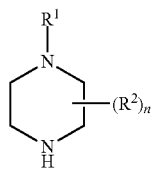

in the presence of a base, thereby synthesizing a compound of formula (Vb)

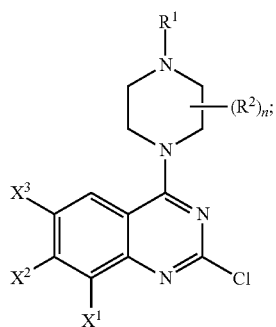

and
(d) contacting the compound of step (c) with a fluorinating agent in the presence of a base thereby synthesizing a compound of formula (II).

Embodiment 4. The process of embodiment 3, wherein the base of step (a) is DBU.

Embodiment 5. The process of embodiment 3, wherein the chlorinating agent of step (b) is $POCl_3$.

Embodiment 6. The process of embodiment 3, wherein the base of step (c) is DIPEA.

Embodiment 7. The process of embodiment 3, wherein the fluorinating agent of step (d) is KF.

Embodiment 8. The process of any one of embodiments 3-7, wherein the compound of formula (IV) is prepared according to the process (P3) comprising:

(a) contacting a compound of formula (IVa)

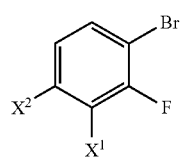

with i-PrMgCl thereby synthesizing a compound of formula (IVb)

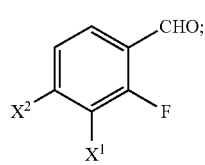

(b) contacting the compound of step (a) with hydroxylamine thereby synthesizing a compound of formula (IVc)

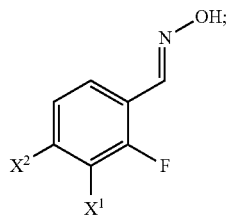

(c) contacting the compound of step (b) with a base and a dehydratization agent in acetonitrile thereby synthesizing a compound of formula (IVd)

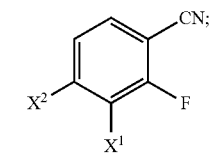

(d) contacting the compound of step (c) with ammonia thereby synthesizing a compound of formula (IVe)

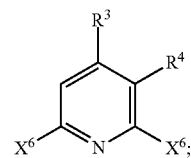

and
(e) contacting the compound of step (d) with a chlorinating agent thereby synthesizing the compound of formula (IV).

Embodiment 9. The process of embodiment 1, wherein the compound of formula (III) is prepared according to the process (P4) comprising:

(a) contacting a compound of formula (VIa)

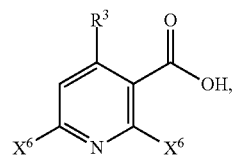

wherein $X^6$ is Cl or I, with a halogenating agent to form a compound of formula (VIb)

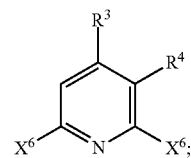

(b) brominating the compound of formula (VIb) to form a compound of formula (VI)

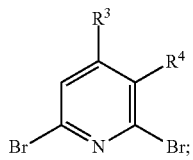

and (c) contacting the compound of formula (VI) with a compound having formula NH(PG)$_2$ thereby making a compound of formula (III).

Embodiment 10. The process of embodiment 9, wherein $X^6$ is Cl.

Embodiment 11. The process of embodiment 9, wherein the halogenating agent is SF$_4$ in HF.

Embodiment 12. The process of embodiment 9, wherein the bromination is performed using HBr in an acid.

Embodiment 13. The process of any one of embodiments 9-12, wherein the compound of formula (III) has formula:

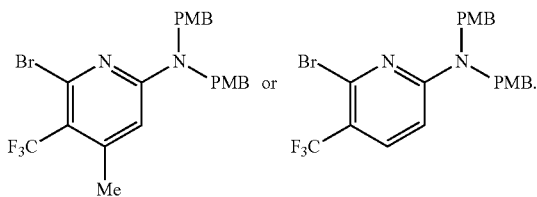

Embodiment 14. The process of any one of embodiments 1-13, wherein $X^1$ is halogen.

Embodiment 15. The process of any one of embodiments 1-13, wherein $X^1$ is F or Cl.

Embodiment 16. The process of any one of embodiments 1-13, wherein $X^3$ is halogen.

Embodiment 17. The process of any one of embodiments 1-13, wherein $X^3$ is F or Cl.

Embodiment 18. The process of any one of embodiments 1-17, wherein $R^1$ is PG$^1$.

Embodiment 19. The process of embodiment 1-18, wherein PG$^1$ is Ac (acetyl), trifluoroacetyl, Bn (benzyl), Tr (triphenylmethyl or trityl), benzylidenyl, p-toluenesulfonyl, PMB (p-methoxybenzyl), Boc (tert-butyloxycarbonyl), Fmoc (9-fluorenylmethyloxycarbonyl) or Cbz (carbobenzyloxy).

Embodiment 20. The process of any one of embodiments 1-19, wherein $R^1$ is Boc (tert-butyloxycarbonyl).

Embodiment 21. The process of any one of embodiments 1-20, wherein $R^2$ is unsubstituted C$_{1-6}$ alkyl or unsubstituted C$_{1-6}$ cyanoalkyl.

Embodiment 22. The process of any one of embodiments 1-21, wherein $R^2$ is methyl.

Embodiment 23. The process of any one of embodiments 1-22, wherein $R^3$ is hydrogen or $R^{3A}$-substituted or unsubstituted C$_{1-3}$ alkyl.

Embodiment 24. The process of any one of embodiments 1-23, wherein $R^3$ is methyl.

Embodiment 25. The process of any one of embodiments 1-24, wherein $R^4$ is CF$_3$, CHF$_2$, or CH$_2$F.

Embodiment 26. The process of any one of embodiments 1-25, wherein $R^3$ is methyl and $R^4$ is CF$_3$.

Embodiment 27. The process of any one of embodiments 1-26, wherein each PG is independently a protecting group selected from the group consisting of Ac (acetyl), trifluoroacetyl, phthalimide, Bn (benzyl), Tr (triphenylmethyl or trityl), benzylidenyl, p-toluenesulfonyl, DMB (dimethoxybenzyl), PMB (p-methoxybenzyl), Boc (tert-butyloxycarbonyl), Fmoc (9-fluorenylmethyloxycarbonyl) or Cbz (carbobenzyloxy).

Embodiment 28. The process of embodiment 27, wherein each PG is p-methoxybenzyl.

Embodiment 29. The process of any one of embodiments 1-28, wherein the organomagnesium compound is selected from the group consisting of isopropylmagnesium chloride, isopropylmagnesium bromide, isopropylmagnesium iodide, isopropylmagnesium chloride lithium chloride complex, sec-butylmagnesium chloride, lithium tri-n-butylmagnesiate, lithium triisopropylmagnesiate, and lithium (isopropyl)(di-n-butyl)magnesiate).

Embodiment 30. The process of embodiment 29, wherein the organomagnesium compound is i-PrMgCl·LiCl.

Embodiment 31. The process of any one of embodiments 1-30, wherein the zinc compound is selected from the group consisting of ZnCl$_2$, ZnBr$_2$, ZnI$_2$, Zn(TFA)$_2$, Zn(OAc)$_2$, and Zn(OPiv)$_2$.

Embodiment 32. The process of embodiment 31, wherein the zinc compound is Zn(OPiv)$_2$·LiCl.

Embodiment 33. The process of any one of embodiments 1-31, wherein the transition metal catalyst precursor is a Pd or Ni catalyst precursor is selected from the group consisting of Pd(OAc)$_2$, PdCl$_2$, PdCl$_2$(MeCN)$_2$, Pd(benzonitrile)$_2$Cl$_2$, Pd(dba)$_2$, Pd$_2$(dba)$_3$, Pd(PPh$_3$)$_4$, Pd(PCy$_3$)$_2$, Pd(PtBu$_3$)$_2$, Pd(TFA)$_2$, [Pd(allyl)Cl]$_2$, [Pd(cinammyl)Cl]$_2$, [PdCl(crotyl)]$_2$, PdCl(η5-cyclopentadienyl), [(η3-allyl)(η5-cyclopentadienyl)palladium(II)], [Ni(η5-cyclopentadienyl)(allyl)], [bis(1,5-cyclooctadiene)nickel(0)], NiCl$_2$, NiBr$_2$, Ni(OAc)$_2$, and Nickel(II) acetylacetonate.

Embodiment 34. The process of any one of embodiments 1-32, wherein the chiral ligand is

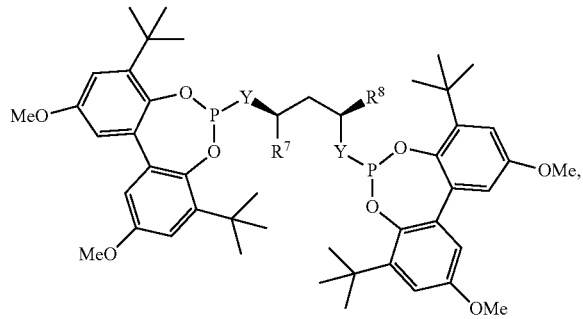

wherein

Y is O or NR$^7$; and

R$^7$ and R$^8$ are independently unsubstituted C$_{1-6}$ alkyl.

Embodiment 35. The process of embodiment 33, wherein R$^7$ and R$^8$ are the same.

Embodiment 36. The process of embodiment 33, wherein R$^7$ and R$^8$ are each independently methyl, ethyl, or phenyl.

Embodiment 37. The process of any one of embodiments 1-33, wherein the chiral ligand is (R,R)-chiraphite ligand.

Embodiment 38. The process of any one of embodiments 1-34, wherein the zinc compound is Zn(OPiv)$_2$·LiCl, the Pd catalyst precursor is [Pd(cinammyl)Cl]$_2$, and the chiral ligand is (R,R)-chiraphite ligand.

Embodiment 39. The process of embodiment 1, wherein the compound of formula (I) has formula:

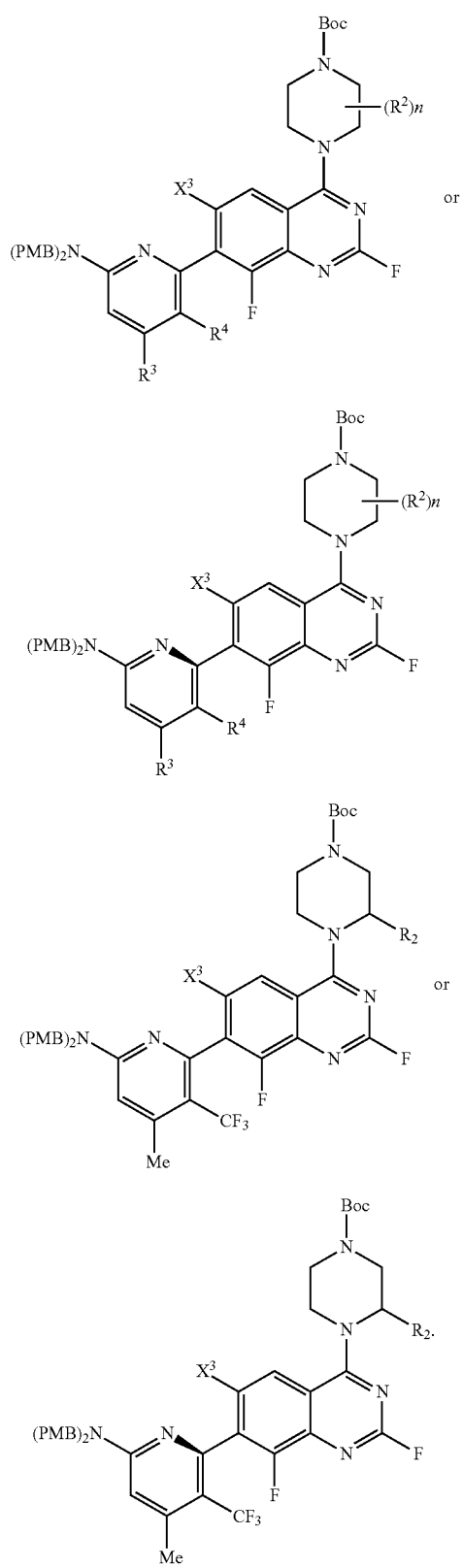

Embodiment 40. The process of embodiment 1, wherein the compound of formula (I) has formula:

wherein $X^3$ is halo.

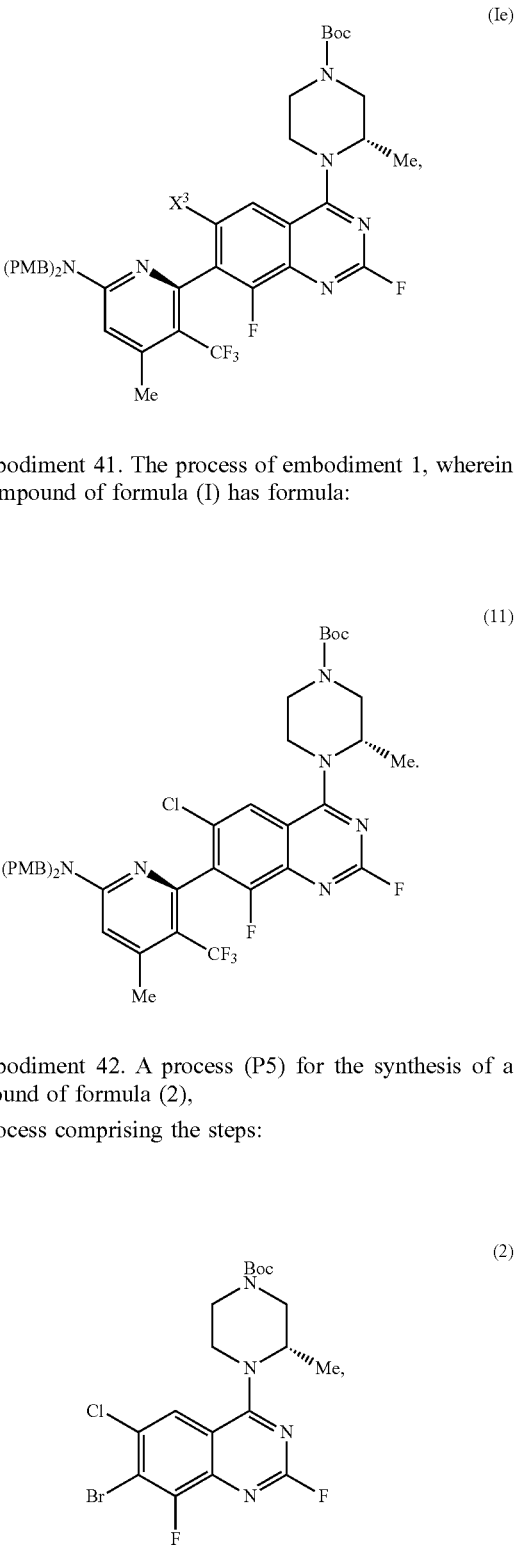

Embodiment 41. The process of embodiment 1, wherein the compound of formula (I) has formula:

Embodiment 42. A process (P5) for the synthesis of a compound of formula (2), the process comprising the steps:

(a) contacting a compound of formula (4a)

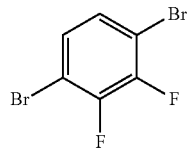

with i-PrMgCl followed by hydroxylamine, thereby synthesizing the compound of formula (4c)

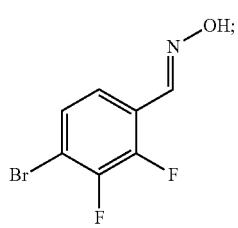 [SMILES: O/N=C/c1ccc(Br)c(F)c1F]

(b) contacting the compound of formula (4c) with TFAA and triethylamine in acetonitrile followed by ammonia, thereby synthesizing the compound of formula (4e)

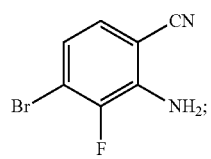 [SMILES: N#Cc1ccc(Br)c(F)c1N]

(c) contacting the compound of (4e) with a chlorinating agent, thereby synthesizing the compound of formula (4)

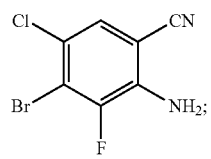 [SMILES: N#Cc1cc(Cl)c(Br)c(F)c1N]

(d) contacting the compound of (4) with $CO_2$ in the presence of DBU, thereby synthesizing the compound of formula (5)

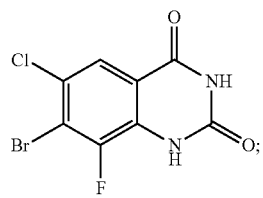 [SMILES: O=c1[nH]c(=O)c2cc(Cl)c(Br)c(F)c2[nH]1]

(e) contacting the compound of formula (5) with $POCl_3$ and DIPEA followed by tert-butyl (S)-3-methylpiperazine-1-carboxylate in DIPEA, thereby synthesizing the compound of formula (5b)

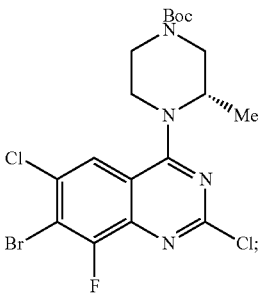 [SMILES: C[C@H]1CN(C(=O)OC(C)(C)C)CCN1c1nc(Cl)nc2c(F)c(Br)c(Cl)cc12]

and (f) contacting the compound of (5b) with KF, DABCO, and MsOH, thereby forming the compound of formula (2).

Embodiment 43. The process of embodiment 1, wherein the compound of formula (III) has formula:

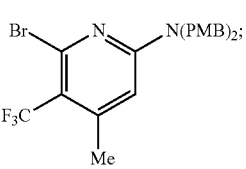

(3)

and wherein the compound of formula (3) is synthesized according a process (P6) comprising:
(a) contacting a compound of formula (6a)

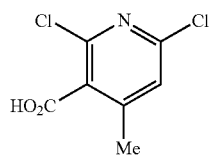 [SMILES: Cc1cc(Cl)nc(Cl)c1C(=O)O]

with $SF_4$ and HF thereby synthesizing a compound of formula (6b)

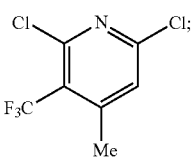 [SMILES: Cc1cc(Cl)nc(Cl)c1C(F)(F)F]

(b) contacting the compound of formula (6b) with HBr in AcOH to form a compound of formula (6)

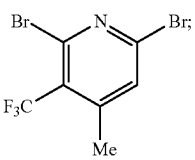 [SMILES: Cc1cc(Br)nc(Br)c1C(F)(F)F]

(c) contacting the compound of formula (6) with (PMB)$_2$NH, triethylamine, and NBP, thereby synthesizing the compound of formula (III).

Embodiment 44. The process of embodiment 1, wherein the process further comprises synthesizing a compound of formula (G) according to the process (P7),
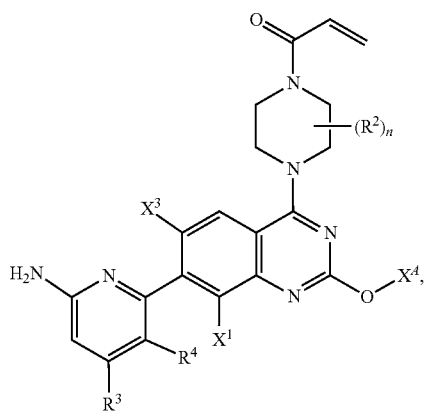
or a tautomer, stereoisomer, atropisomer, or pharmaceutically acceptable salt thereof, wherein;
$X^A$ is selected from the group consisting of
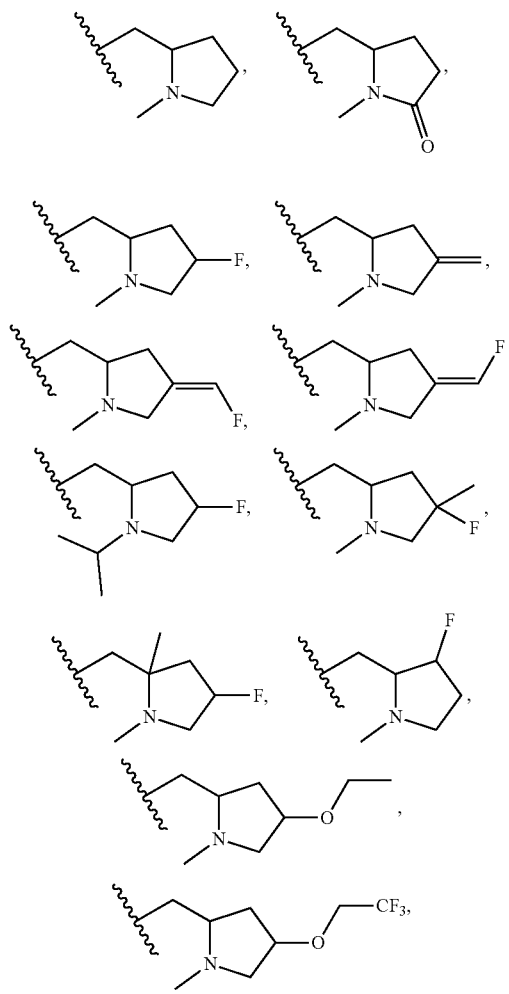
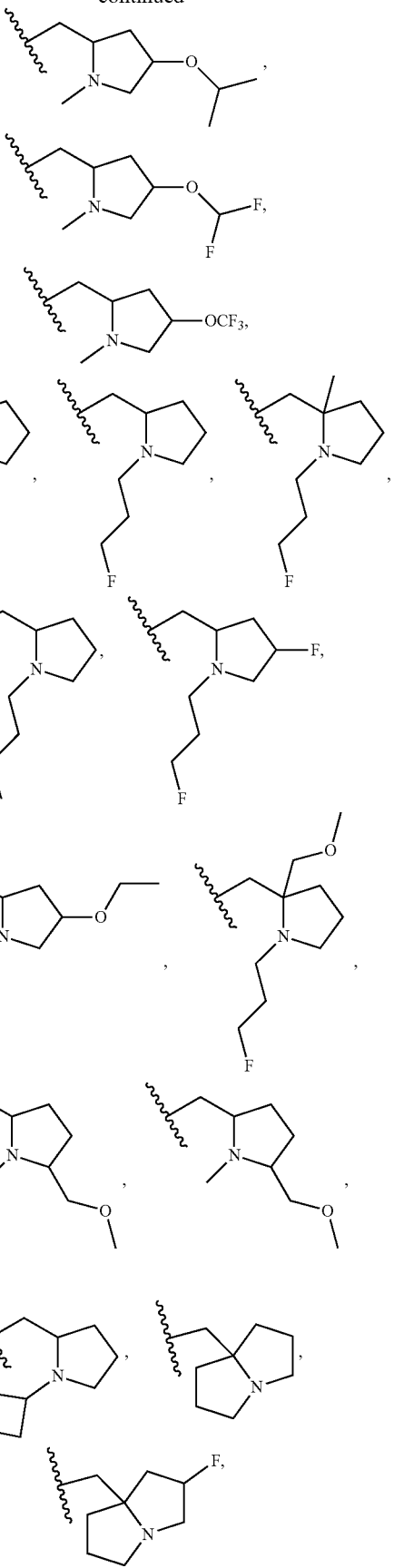

-continued

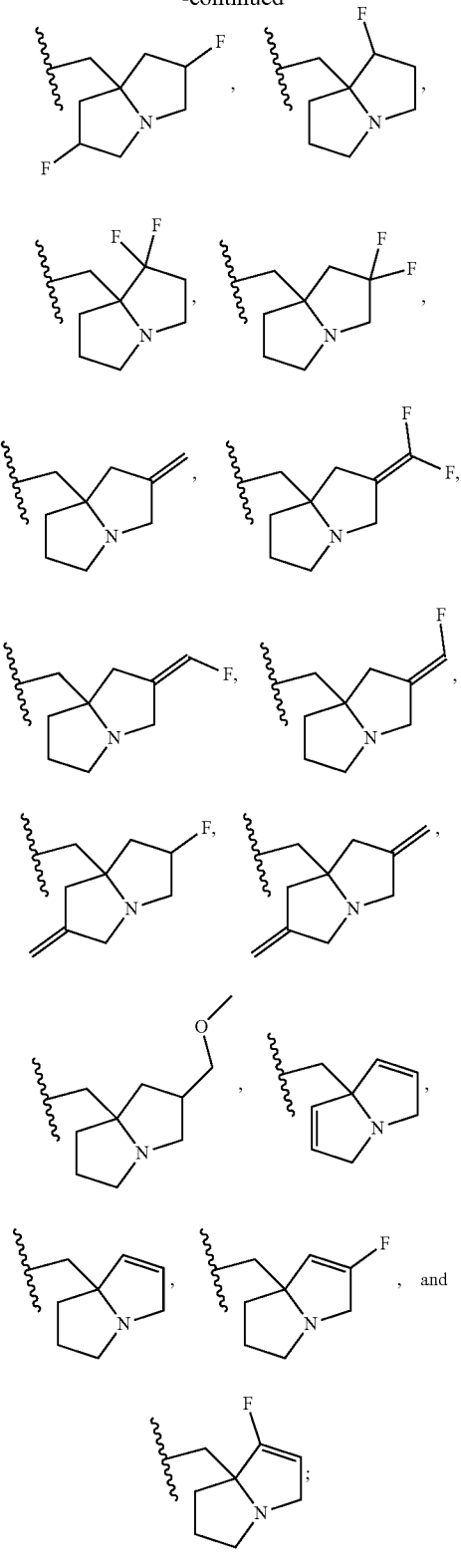

the process comprising:
(a) contacting the compound of formula (I) or a solvate, tautomer, stereoisomer, atropisomer, or salt thereof with a moiety comprising $X^4$ in the presence of base and an activating agent, thereby synthesizing a compound of formula (G1);

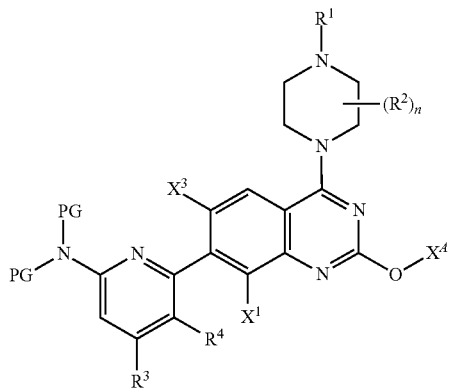

(b) removing the PG groups and optionally $R^1$ from the compound of formula (G1); and
(c) contacting the compound of step (b) with a compound of formula (VII)

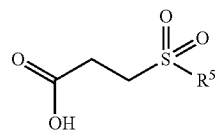

in the presence of an activating agent, followed by contacting with a base, thereby making a compound of formula (G) or a tautomer, stereoisomer, atropisomer, or pharmaceutically acceptable salt thereof.

Embodiment 45. A process (P9) for the synthesis of a compound of formula (1):

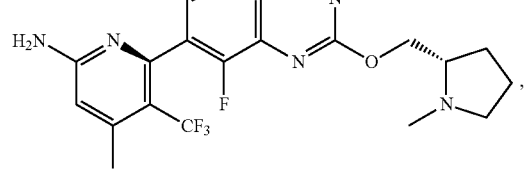

or a pharmaceutically acceptable salt thereof, the process comprising:
(a) contacting a precooled solution comprising a compound of formula (2)

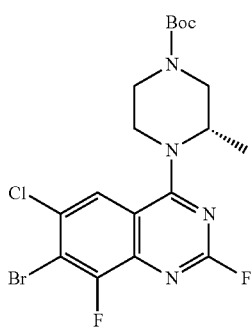

or a salt thereof with a pre-cooled solution comprising i-PrMgCl·LiCl using a flow rate resulting in a residence time of about 15-150 seconds for the Mg—Br exchange;
(b) transferring the mixture of step (a) to a continuous stirred tank reactor (CSTR) comprising a precooled solution of $ZnCl_2$ or $Zn(OPiv)_2$ and maintaining a constant residence time of about 3-7 minutes at about −20° C. to 20° C.;
(c) contacting the mixture of step (b) with NaTFA and a compound of formula (3)

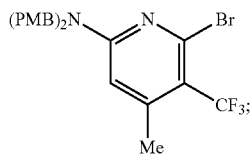

(d) contacting the mixture of step (c) or a salt thereof with a Pd or Ni catalyst precursor and a chiral ligand thereby synthesizing a compound of formula (11);

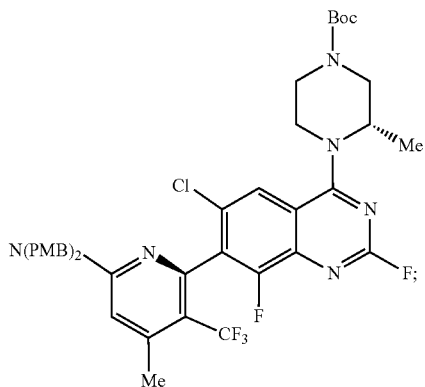

(11)

or a solvate or salt thereof,
(e) contacting the compound of formula (11) or a solvate or salt thereof, with a compound of formula HO—$X^4$, wherein $X^4$ has formula

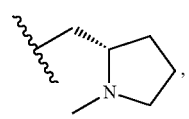 [SMILES: *C[C@@H]1CCCN1C]

and a base thereby synthesizing a compound of formula (1b);

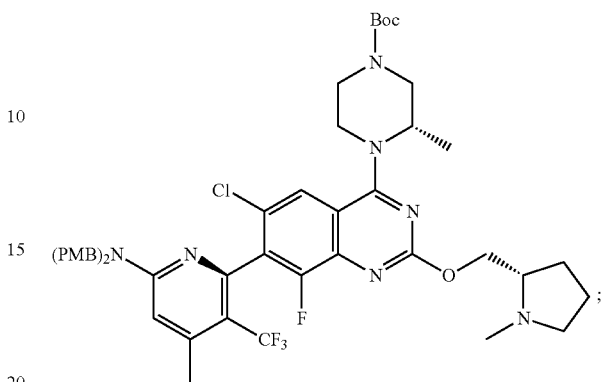

(1b)

or a solvate or pharmaceutically acceptable salt thereof;
(f) contacting the compound of formula (1 b) with MsOH in an acid thereby synthesizing a compound of formula (1a);

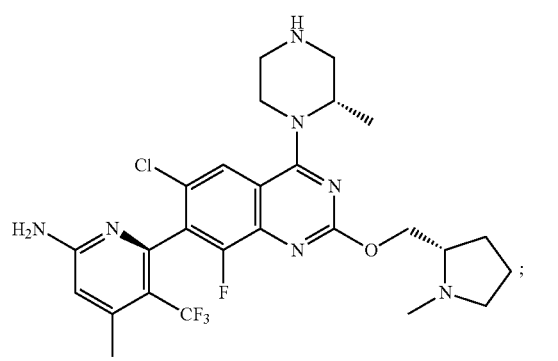

(1a)

or a solvate or pharmaceutically acceptable salt thereof; and
(g) contacting the compound of formula (Ia) or a solvate or pharmaceutically acceptable salt thereof with

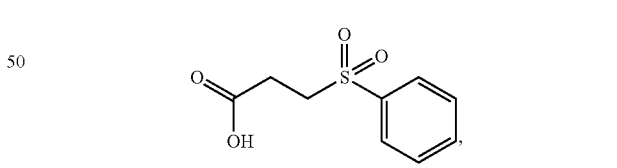

in the presence of an activating agent, followed by contacting with a base, thereby making a compound of formula (1) or a pharmaceutically acceptable salt thereof.

Embodiment 46. The process of embodiment 45, wherein the acid of step (f) is AcOH, trifluoroacetic acid, chlorosulfonic acid, sulfuric acid, HCl, HBr, p-toluenesulfonic acid, or trifluoromethanesulfonic acid.

Embodiment 47. The process of embodiment 45, wherein compound (2) is synthesized according to the process of embodiment 42.

Embodiment 48. The process of embodiment 45, wherein the precooled solution of step (b) comprises $Zn(OPiv)_2$·LiCl.

EXAMPLES

The following Examples are presented by way of illustration, not limitation.

Example 1: Compound 2: tert-butyl (S)-4-(7-bromo-6-chloro-2,8-difluoroquinazolin-4-yl)-3-methylpiperazine-1-carboxylate

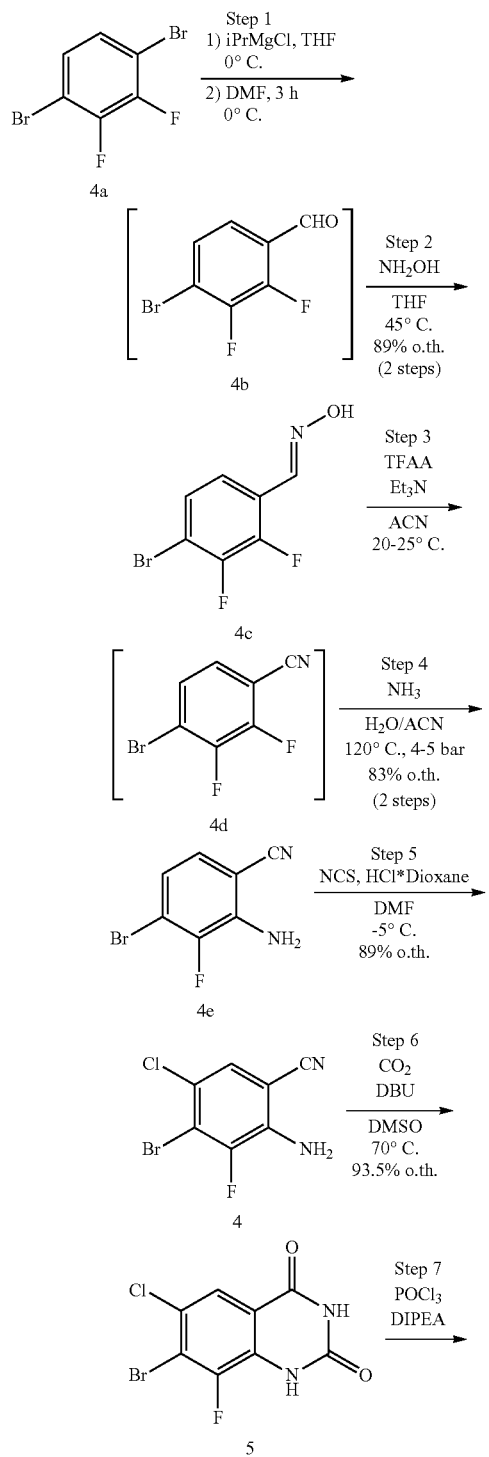

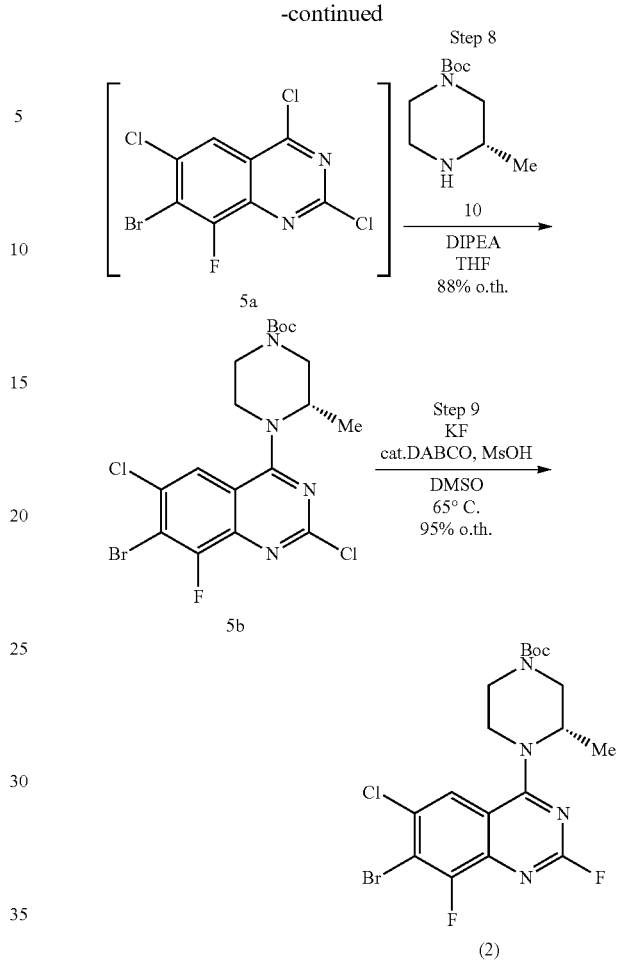

Step 1

To a solution of 1,4-Dibromo-2,3-difluorobenzene (100 g) in THF (200 mL) was added isopropylmagnesium bromide (1.1 eq., 2 M in THF) over at least 2 h at 0° C. After stirring for 30 min, DMF (2.0 eq.) was added over at least 3 h. After aging for 1 h (IPC conversion >97.5%-a/a) the mixture was added to a cooled solution (0° C.) of citric acid (1.2 eq.) in water (1 Veq.) in one portion. The mixture was warmed to 45° C. and the aqueous phase was separated.

Step 2

To the organic phase containing 4b was added hydroxylamine (1.05 eq., 50%-wt in water) at 45° C. over at least 1 h. After stirring for 30 min (IPC conversion >98.8%-a/a) brine (100 mL) was added at the same temperature. The aqueous phase was separated and the organic phase was concentrated by vacuum distillation to a total volume of 200 mL. Afterwards, vacuum distillation was proceeded under constant volume by feeding acetic acid (200 mL). The solution was adjusted to 70° C. before water (100 mL) was added over at least 30 min and seeds were charged. The resulting suspension was cooled to 20° C. followed by addition of water (100 mL). The precipitate was filtered, the filter cake washed with ACN/water (1:2), and the wet product dried in vacuo to obtain 77.6 g of 4c (89% o.th.). $^1$H NMR (400 MHz, DMSO-d6) δ[ppm]=11.89 (s, 1H), 8.19 (s, 1H), 7.56-7.46 (m, 2H).

Step 3 and Step 4

To a suspension of 4c (100 g) in ACN (200 mL) was added triethylamine (2.2 eq.) at 20° C. To the resulting solution was added TFAA (1.1 eq.) over at least 2.5 h. After complete addition the reaction mixture was stirred for 30 min (IPC conversion >99.8%-a/a). The solution, containing 4d was placed in an autoclave, and ammonia (6.8 eq., 25%-wt in water) was added in one portion. The vessel was sealed and heated to 120° C. for at least 6 h (IPC conversion >99.0%-a/a). The mixture was adjusted to 90° C. and then cooled to 50° C. over at least 3 h before water (220 mL) was added over at least 1 h. Afterwards, the suspension was further cooled to 20° C. and aged for 1 h. The precipitate was filtered, and the filter cake washed with ACN/water (1:2). The wet product was dried in vacuo to obtain 75.6 g of 4e (83% o.th.). $^1$H NMR (400 MHz, DMSO-d6) δ[ppm]=7.23 (br d, J=8.4 Hz, 1H), 6.86 (dd, J=8.4, 6.1 Hz, 1H), 6.49 (bs, 2H).

Step 5:

To a solution of 4e (100 g) in DMF (500 mL) was added HCl in dioxane (4.0 M, 0.25 eq.) at 0° C. The solution was cooled to −5° C. and NCS (1.15 eq.) was added in small portions, maintaining the temperature below 2° C. (target −5° C.). After complete addition, the reaction mixture was stirred for 1.5 h at −5° C. (IPC). Then, n-PrOH (100 mL) was added at 0° C. to initiate product precipitation (visual IPC for suspension). After stirring for at least 30 min, water (250 mL) was added at 0-5° C. over at least 1.5 h. The suspension was filtered, and the filter cake was washed twice with ACN/water (1:2) (100 mL). The wet product was dried in a vacuum oven at 60° C. to obtain 102.8 g of 4 (89% o.th.). 1H NMR (400 MHz, DMSO-d6) δ [ppm]=7.67 (d, J=2.1 Hz, 1H), 6.49 (bs, 2H).

Alternative Step 5:

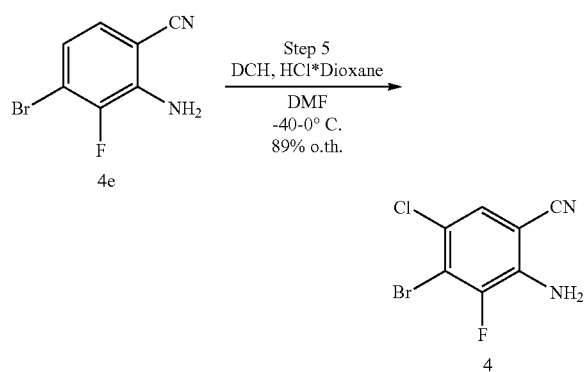

To a solution of 4e (100 g) in DMF (700 mL) was added HCl in dioxane (4.0 M, 0.25 eq.) at −40° C. The solution was cooled to −5° C. and 1,3-Dichloro-5,5-Dimethylhydantoin (DCH) (0.60 eq.) was added in portions. After complete addition, the reaction temperature was adjusted to −10-0° C. and further stirred for 1.5 h. Then, n-PrOH (140 mL) and water (350 mL) were added at −5-5° C. to initiate product precipitation (visual IPC for suspension). After stirring for at least 30 min at −5-5° C., the suspension was filtered, and the filter cake was washed twice with ACN/water (1:2) (2×100 mL). The wet product was dried in a vacuum oven at 60° C. to obtain 97.5 g of 4 (84% o.th.). $^1$H NMR (400 MHz, DMSO-d6) δ[ppm]=7.67 (d, J=2.1 Hz, 1H), 6.49 (bs, 2H).

Step 6:

A suspension of 4 (50 g) in DMSO (150 mL) was stirred under $CO_2$ atmosphere for 15 min at 25° C. before DBU (33.6 g) was added. After stirring for 1 h at 25° C. the reaction was heated to 70° C. and stirred for further 6 h (IPC 4<1.0%-a/a). Then, acetic acid (14.4 g) was added over at least 1 h. The mixture was stirred at 70° C. for at least 1 h before water (50 mL) was added over at least 2 h. The resulting suspension was aged for 3 h at 70° C., then cooled to 25° C. over at least 3 h and further stirred at that temperature for 1 h. The suspension was filtered and washed with DMSO/water (3:1, 50 mL) and IPA/water (1:1, 50 mL). The filter cake was suspended in IPA/water (1:2, 200 mL) and stirred over at least 30 min, filtered, washed with IPA/water (1:1, 20 mL), and dried in the vacuum oven at 60° C. to obtain 55.0 g of 5 (93.5% o.th.). $^1$H NMR (400 MHz, DMSO-d6) δ[ppm]=11.64 (s, 1H), 11.60 (s, 1H), 7.84 (d, J=1.8 Hz, 1H).

Step 7:

To a suspension of 5 (50 g) in toluene (300 ml) was added $POCl_3$ (130.6 g) at 25° C. The mixture was stirred for 30 min before DIPEA (49.5 g) was added over at least 2 h. The reaction mixture was warmed to 35° C. and stirred for 30 min. To the resulting solution was added water (0.77 g) in one portion. The reaction mixture was heated to 70° C. and stirred for at least 2 h before it was cooled to 25° C. (IPC: 5a >97.0%-a/a). The reaction mixture was added to water (400 mL) over at least 1 h at 25° C. After complete addition, the biphasic mixture was stirred for at least 30 min before it was filtered through Harborlite 800 (10.3 g). The filter cake was rinsed with toluene (25 mL) before the phases were separated. The organic phase was washed with brine (20%-w/w in water, 100 mL) and reduced to 160 mL by vacuum distillation.

Step 8:

Subsequently, the solution of step 7 was telescoped and cooled to 25° C. and (S)-1-Boc-3-methylpiperazine (34.1 g) was added in five portions over at least 1 h. After stirring for 30 min DIPEA (24.2 g) was added within 1 h and the resulting suspension was stirred for 30 min (IPC: 5a <0.4%-a/a). The mixture was heated to 40° C. and stirred for 1 h before heptane was added over at least 1 h. After additional stirring for 1 h at 40° C., the suspension was cooled to 25° C. over at least 1 h and aged for at least 2 h. The suspension was filtered and washed with heptane/toluene (2:1, 50 mL). The filter cake was suspended in IPA/water (2:1, 200 mL) and stirred over at least 30 min, filtered, washed twice with IPA/water (2:1, 100 mL), and dried in the vacuum oven at 45° C. to obtain 74.1 g of 5b (88% o.th.). $^1$H NMR (400 MHz, Chloroform-d) 5 [ppm]=7.69 (d, J=2.0 Hz, 1H), 4.74-4.65 (m, 1H), 4.30-3.85 (m, 3H), 3.68-3.56 (m, 1H), 3.33-2.97 (m, 2H), 1.48 (s, 9H), 1.45 (d, J=6.7 Hz, 3H).

Step 9:

To a stirred suspension of 5b (20 g) in DMSO (100 mL) was added potassium fluoride (3.1 g, 1.3 eq.), DABCO (0.18 g, 0.04 eq.), and methanesulfonic acid (0.11 ml, 0.04 eq.) at room temperature. The mixture was heated to 65° C. and stirred for at least 3 h. After full conversion (IPC: 5b <0.1%-a/a) the mixture was cooled to 50° C. and stirred at the same temperature over at least 1 h (product precipitation occurs). Afterwards, the suspension was cooled to 20° C. over at least 3 h before 40 mL of ACN/water (1:2) was added over at least 1 h. After stirring for 30 min, the precipitate was filtered and washed with 20 mL ACN/water (1:1). The filter cake was suspended in 60 mL of ACN/water (1:2) and stirred over at least 30 min, filtered, washed with 20 mL ACN/water (1:2), and dried in the vacuum oven at 60° C. to obtain 17.9 g of 2 (95% o.th.). $^1$H NMR (400 MHz, Chloroform-d) 6 [ppm]=7.76 (d, J=1.9 Hz, 1H), 4.77-4.70 (m, 1H), 4.28-4.22 (m, 1H), 4.18-3.85 (m, 2H), 3.66 (dd, J=13.0, 3.1 Hz, 1H), 3.34-3.00 (m, 2H), 1.51 (s, 9H), 1.49 (d, J=6.9 Hz, 3H).

Example 2: Continuous Flow Process for Compound (2b)

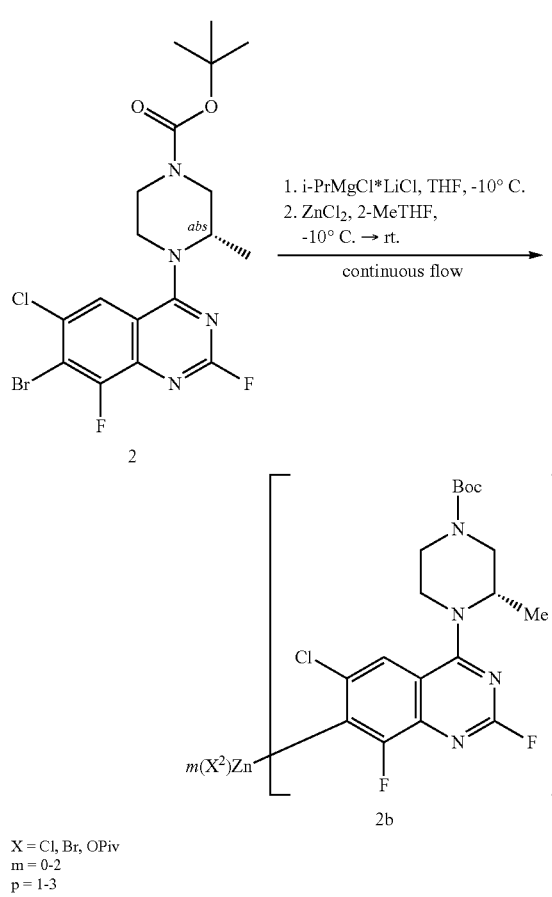

X = Cl, Br, OPiv
m = 0-2
p = 1-3

Feed Preparation:

Feed 1: 273 g of 2 was dissolved in 1166 g THF to give 1500 mL solution (0.38 M) with the density of 0.96. Feed 2: i-PrMgCl·LiCl was used as a 1.20 M solution in THF (assay corrected based on CoA). ZnCl$_2$ was used as a 2.00 M (25.8 wt %) solution in 2-MeTHF (assay corrected based on CoA).

Setup of the system described above is provided in FIG. 1.

All pumps and transfer lines were purged with their corresponding feed solutions. Feed 1 comprising compound 2 (1.00 equiv) and Feed 2 comprising i-PrMgCl·LiCl (1.05 equiv) were precooled and continuously dosed a suitable flow reactor at Jacket Temperature (JT) between −20 to 0° C. The flow rates of the two feeds were adjusted to result in a residence time of approximately 30 s for the Mg—Br exchange.

The exiting reaction mixture (Compound 2a) was directed to a continuous stirred tank reactor (CSTR) where a solution of ZnCl$_2$ was simultaneously added (1.15 equiv), maintaining a constant residence time of approximately 5 min. The temperature was kept constant at an internal temperature (IT) between −10 to 0° C.

Compound 2b was collected in a receiving tank at IT between 0-25° C. Compound 2b was found to be stable at −20 to 25° C. for several weeks.

Example 2a

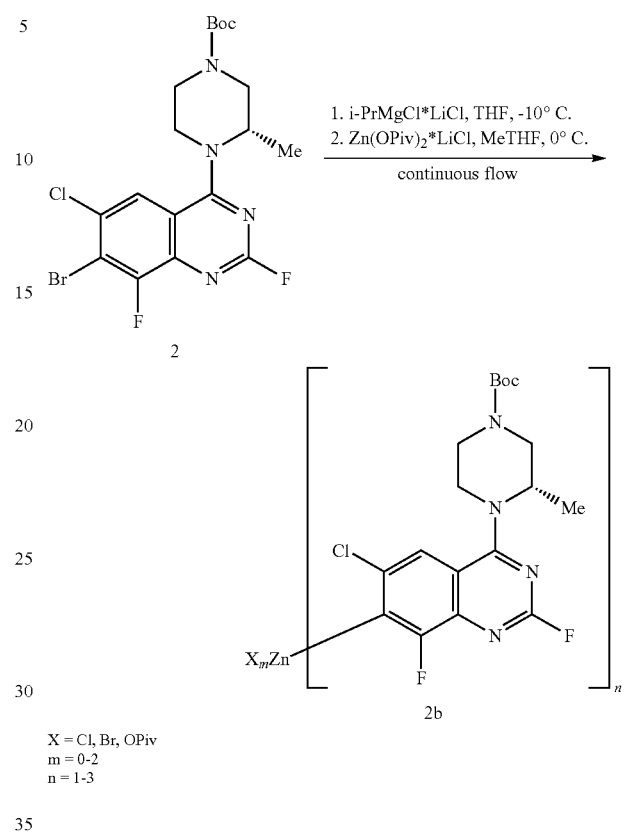

X = Cl, Br, OPiv
m = 0-2
n = 1-3

Feed Preparation:

Feed 1: 117 g of 2 was dissolved in 783 g THF to give 959.5 mL solution (0.25 M) with the density of 0.94. Feed 2: i-PrMgCl·LiCl was used as a 1.20 M solution in THF (assay corrected based on CoA). Zn(OPiv)$_2$·LiCl was used as a 0.67 M (20.0 wt %) solution in 2-MeTHF (assay corrected based on CoA).

Setup of the system described above is provided in FIG. 1.

All pumps and transfer lines were purged with their corresponding feed solutions. Feed 1 comprising compound 2 (1.00 equiv) and Feed 2 comprising i-PrMgCl·LiCl (1.15 equiv) were precooled and continuously dosed a suitable flow reactor at Jacket Temperature (JT) between −20 to 0° C. The flow rates of the two feeds were adjusted to result in a residence time of approximately 45 s for the Mg—Br exchange.

The exiting reaction mixture (Compound 2a) was directed to a continuous stirred tank reactor (CSTR) where a solution of Zn(OPiv)$_2$·LiCl was simultaneously added (0.75 equiv), maintaining a constant residence time of approximately 5 min. The temperature was kept constant at an internal temperature (IT) between −5 to 5° C.

Compound 2b was collected in a receiving tank at IT between 0-30° C. Compound 2b was found to be stable at −20 to 30° C. for several weeks.

Five different experiments were conducted where the equivalents of ZnCl$_2$ and Compound 2a were varied from 0.33, 0.50, 0.75, 1.00 to 1.50. In the corresponding $^{19}$F NMR the presence of three different species/compounds was observed in different levels depending on the equivalents of ZnCl$_2$ used. A 2D NOESY indicated that these species can interconvert without noticeable effect on the kinetics of the resulting Nesighi.

The Des-Bromo-Compound 2a was found as another compound present in the spectra and originates from the proton quenched reaction due to residual moisture in the NMR solvent.

Example 3

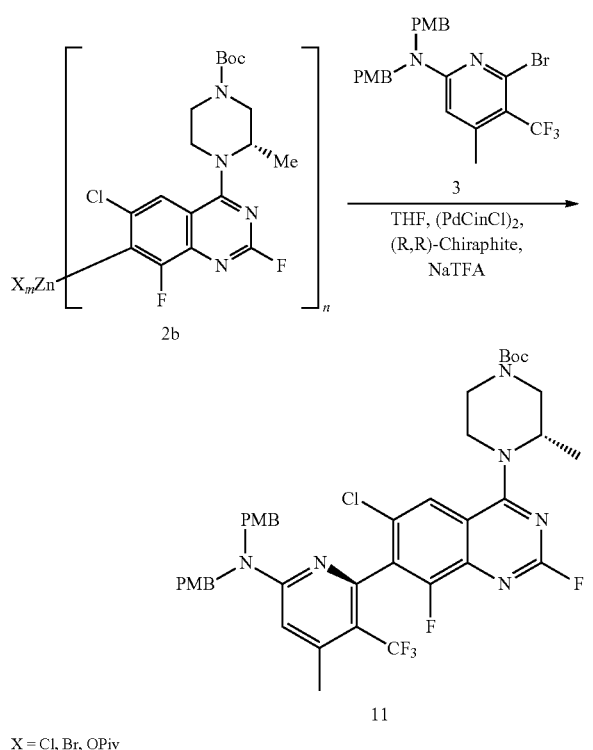

X = Cl, Br, OPiv
m = 0-2
n = 1-3

A first reactor under an argon atmosphere with its jacket temperature (TJ) at 10° C. was charged with Compound 2b in suspension (32 mmol, 1.1 equiv.). NaTFA (11.8 g, 86.8 mmol, 3.00 equiv.) was added in three portions over 30 min. The resulting suspension was heated to an internal temperature (IT) of 50° C. over 40 min (1° C./min). In a second reactor under an argon atmosphere, Compound 3 (14.4 g, 29.0 mmol, 1.00 equiv.) was added and the reactor was purged with argon for 10 min. Degassed THF (26 mL) was added and the resulting solution was obtained after stirring for 10 min. The solution was transferred into the first reactor via a pump over 5 min. Then, a solution of palladium(π-cinnamyl) chloride dimer (75.1 mg, 0.005 eq.) and (R,R)-Chiraphite (279.8 mg, 0.011 eq) in THF (8.0 mL) was transferred into the first reactor via syringe. The resulting solution was stirred at an IT of 50° C. until full conversion was obtained (typically 15 h). The reaction mixture was cooled down to room temperature (rt).

In a third reactor under an argon atmosphere with its TJ at 20° C. was added aqueous sodium citrate tribasic (20% w/w, 110 g) and toluene (72 mL). Then, the reaction mixture in the second reactor was transferred to the third reactor over 10 min. The biphasic mixture was stirred for 15 min and then the lower aqueous layer was drained from the third reactor. Then, aqueous sodium citrate tribasic (20% w/w, 110 g) was added into the third reactor. The biphasic mixture was stirred for 15 min and then the lower aqueous layer was drained from the third reactor. Then, aqueous sodium chloride (10% w/w, 36.5 g) was added into the third reactor. The biphasic mixture was stirred for 15 min and then the lower aqueous layer was drained from the third reactor. The organic layer was concentrated under reduced pressure at TJ 50° C. to a volume of ca. 140 mL. Then, distillation under reduced pressure at constant volume (typically 64 g of toluene is exchanged) of the toluene layer was performed. The resulting solution was pumped over a heated charcoal filter over 45-60 min into a fourth reactor under an argon atmosphere. The third reactor and the filter were rinsed with toluene (50 mL) and added to the fourth reactor. The resulting solution was concentrated under reduced pressure at TJ 50° C. to a volume of ca. 75 mL.

The solution was cooled down to IT 20° C., n-heptane (14 mL) was added over 10 min and seeding was performed. The suspension was aged for 1 h and n-heptane (160 mL) was added over 2 h. The suspension was further stirred overnight. The crystals were filtered off, washed with a solution of toluene/n-heptane (1:1 v/v) and dried under reduced pressure for 1 h to obtain the crude product (24.0 g) as a solid. The crude product (24.0 g) was suspended in toluene (100 mL). The suspension was stirred at TJ 50° C. until a solution was obtained. The solution was concentrated under reduced pressure until a volume of ca. 70 mL was reached. The solution was cooled down to IT 20° C., n-heptane (9 mL) was added over 10 min and seeding was performed. The suspension was aged for 1 h and n-heptane (94 mL) was added over 2 h. The suspension was further stirred overnight. The crystals were filtered off, washed with a solution of toluene/n-heptane (1:1 v/v) and dried under reduced pressure until constant weight was attained. The title compound was isolated in 57% yield (15.2 g) as crystals.

Example 3a

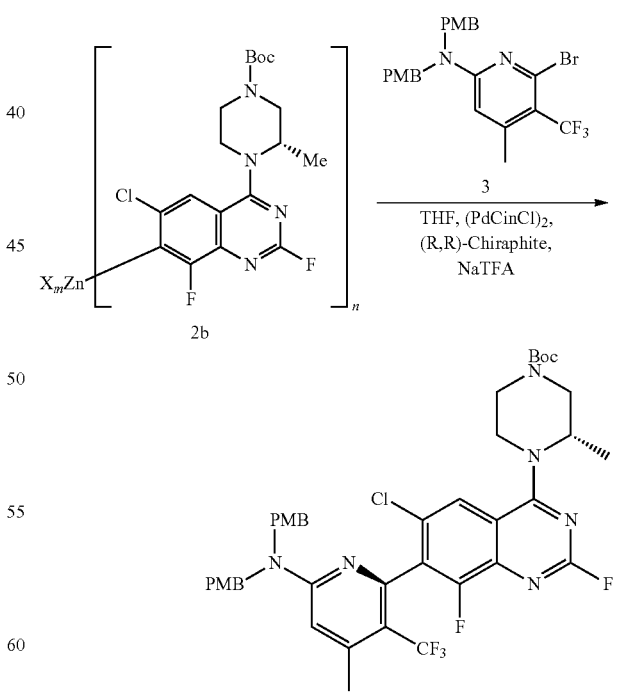

X = Cl, Br, OPiv
m = 0-2
n = 1-3

A first reactor under an argon atmosphere with its jacket temperature (TJ) at 20° C. was charged with NaTFA (15.5 g, 114.3 mmol, 3.00 equiv.). A solution of Compound 2b in THF and 2-Me-THF (41.9 mmol, 1.10 equiv., 230 g) was added. The resulting suspension was heated to an internal temperature (IT) of 50° C. over 40 min (1° C./min). In a second reactor under an argon atmosphere, Compound 3 (18.9 g, 38.1 mmol, 1.00 equiv.) was added and the reactor was purged with argon for 10 min. Degassed THF (30.5 g) was added and the resulting solution was obtained after stirring for 10 min. The solution was transferred into the first reactor via a pump over 5 min. THF (8.9 g) was used to rinse the lines. Then, a solution of palladium(π-cinnamyl) chloride dimer (148 mg, 0.0075 eq.) and (R,R)-Chiraphite (551, 0.0165 eq) in THF (11.6 g) was transferred into the first reactor via syringe. The resulting solution was stirred at an IT of 50° C. until full conversion was obtained (typically 10 h). The reaction mixture was cooled down to room temperature (rt).

In a third reactor under an argon atmosphere with its TJ at 20° C. was added aqueous sodium citrate tribasic (20% w/w, 150 g) and toluene (82.4 g). Then, the reaction mixture in the second reactor was transferred to the third reactor over 10 min. The biphasic mixture was stirred for 15 min and then the lower aqueous layer was drained from the third reactor. Then, aqueous sodium citrate tribasic and sodium carbonate (20% and 5% w/w respectively, 150 g) was added into the third reactor. The biphasic mixture was stirred for 15 min and then the lower aqueous layer was drained from the third reactor. Then, aqueous sodium chloride (10% w/w, 50.1 g) was added into the third reactor. The biphasic mixture was stirred for 15 min and then the lower aqueous layer was drained from the third reactor. The organic layer was concentrated under reduced pressure at TJ 50° C. to a volume of ca. 140 mL. Then, distillation under reduced pressure at constant volume of the toluene layer was performed until the desired solvent composition was obtained (typically 120 g of toluene is exchanged). The resulting solution was pumped over a heated charcoal filter over 45-60 min into a fourth reactor under an argon atmosphere. The third reactor and the filter were rinsed with toluene (32.7 g) and added to the fourth reactor. The resulting solution was concentrated under reduced pressure at TJ 50° C. to a volume of ca. 140 mL.

The solution was cooled down to IT 20° C., n-heptane (12.9 g) was added over 10 min and seeding was performed. The suspension was aged for 2 h and n-heptane (81 g) was added over 2 h. The suspension was cooled down to 0° C. over 2 h and was further stirred overnight. The crystals were filtered off, washed with a solution of toluene/n-heptane (1:1 v/v) and dried under reduced pressure until constant weight was attained. The title compound was isolated in 81.4% yield (28.7 g, 88% assay) as crystals.

Example 4: Compound 3: 2,6-dichloro-4-methyl-5-(trifluoromethyl)pyridine

Step 1:

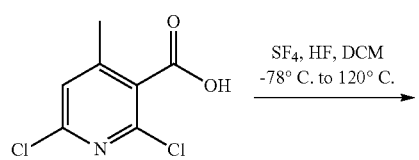

SF₄, HF, DCM
−78° C. to 120° C. →

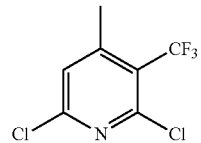

2,6-dichloro-4-methyl-pyridine-3-carboxylic acid (1.0 eq., 22 kg) was charged to an autoclave at ambient temperature. The autoclave was cooled to −20° C. and HF (1.37 rel. weight) was charged then further cooled to −78° C. and SF₄ (2.5 eq.) was charged. The autoclave was sealed and the reaction mixture allowed to warm to ambient temperature then slowly heated to 70-80° C. and stirred at same temperature.

After completion, volatiles were vented off through scrubber by nitrogen sparging then MTBE (5 rel. volume) was added. Reaction mass was slowly added in to ice cold demineralized (DM) water (5 rel. volume) then basified (pH 8-9) by adding 25% aqueous potassium carbonate solution (~8 rel. volume) below 10° C. The reaction mass was filtered through celite pad, washed with MTBE (2.5 rel. volume) and layer separated. The aqueous layer was extracted with MTBE (2.5 rel. volume). The combined organic layer was washed with DM water (2×2.5 rel. volume) and concentrated below 30° C. The organic layer was concentrated under reduced pressure below 30° C. then methanol (1.0 rel. volume) charged and again distilled up to thick slurry.

Methanol (4.0 rel. volume) followed by activated charcoal Norit CG1 (10% w/w) was added to above the slurry at 20-30° C. and stirred at same temperature for 60 min. The reaction mass was filtered through Celite bed and washed with methanol (1.5 rel. volume).

The product was purified as follows. To a MeCOH solution of product was added DM water (1.3 rel. volume) in 60 min (~4.5 ml/min) at 20-30° C. then stirred at same temperature for 20 min. Pure product was seeded in to above solution and stirred at 20-30° C. for 20 min. Slowly cooled to −4 to 2° C. in 4 h. 0.7+0.5+0.5 rel. volume of (i.e., total 1.7 rel. volume) of DM water was added in 30 min (~6 ml/min) at −4 to 2° C. (after addition of every lot of water supernatant liquid sample checked for solid precipitation) and stirred at same temperature for 3 h. The resulting solid was filtered and washed with chilled DM water.

Step 2: 2,6-dibromo-4-methyl-3-(trifluoromethyl)pyridine

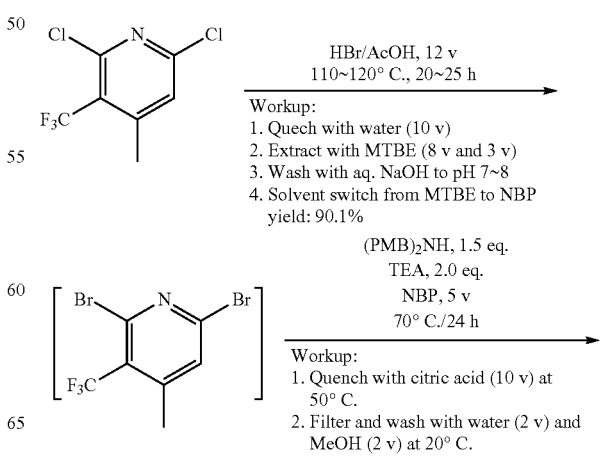

-continued

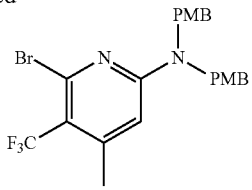

2,6-dichloro-4-methyl-5-(trifluoromethyl)pyridine (5.00 kg, 1.00×, 1.00 equiv) and hydrobromic acid in acetic acid (21.0 kg) were added into a 3000 L-GL reactor. The reactor was adjusted to 110-120° C., hydrobromic acid in acetic acid (56.8 kg) was added into the reactor in portions over 20 h. The mixture was adjusted to 35-45° C. The mixture was stirred and bubbled with nitrogen at 35-45° C. for 1-2 h. The temperature of the reactor was adjusted to 110-120° C., hydrobromic acid in acetic acid (7.0 kg) was added into the reactor. The mixture was adjusted to 35-45° C. Process water (72 kg) and MTBE (43 kg) were added into the reactor at 15-25° C. and stirred for 0.5-1.5 h. The organic layer was collected by separation and aqueous layer was extracted with MTBE (12 kg). All organic layers were combined and adjusted to 0-10° C., then the organic layer was washed with 30% NaOH solution (68 kg) and the pH of mixture was adjusted to 7-8. Water (10 kg) was added. The organic layer was obtained by separation, and washed with 2% $NaHCO_3$ aqueous solution (38 kg) and process water (12 kg). The organic layer was removed water by re-circulate via F909 with molecular sieves (6 kg) for 3-5 h, and the molecular sieves was washed with MTBE (20 kg) after drying. The organic solution was concentrated to 2-3× below 50° C. under reduced pressure, NBP (33 kg) was added. The mixture was concentrated below 50° C. under reduced pressure to remove MTBE (<0.2%, sepc.:<2.0%). 6.16 kg (99.0 A % purity) of product as NBP solution was obtained in 90.1% yield.

Step 3: 6-bromo-N,N-bis(4-methoxybenzyl)-4-methyl-5-(trifluoromethyl)pyridin-2-amine 2,6-dibromo-4-methyl-3-(trifluoromethyl)pyridine NBP solution (6.16 kg, 1.00×, 1.0 equiv.) (Assay corrected) was added into a reactor. $(PMB)_2NH$ (7.7 kg, 1.5 equiv.) and TEA (4.0 kg, 2.0 equiv) were added into the reactor by pump addition. The reactor was adjusted to 70-75° C. and stirred for 24 h, then adjusted to 45-55° C. The reactor was adjusted to 70-75° C. and stirred for 8 h, then adjusted to 45-55° C. The mixture was adjusted to 45-55° C., 20% Citric acid aqueous (68.0 kg) was added into the reactor for 2-3 h. The mixture was adjusted to 15-25° C. for 1-2 h, the wet cake was isolated by centrifuge and rinsed with process water (30 kg) and Methanol (11 kg), 7.15 kg of wet cake was obtained. After drying at 20-30° C. for 20 h under vacuum, 7.15 kg of crude product was obtained.

Step 4

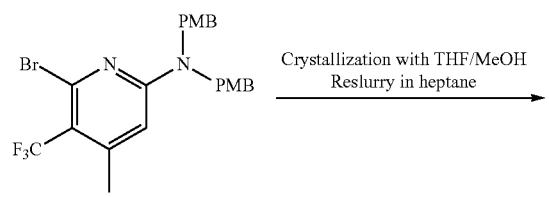
Crystallization with THF/MeOH
Reslurry in heptane

-continued

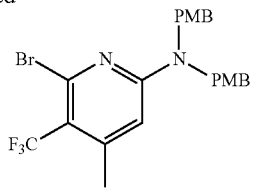

Crude 6-bromo-N,N-bis(4-methoxybenzyl)-4-methyl-5-(trifluoromethyl)pyridin-2-amine from Step 2 (7.15 kg, 1.00×) and THF (31.15 kg) were added into a reactor. The mixture was decolorized by CUNO at 15~25° C. until pale yellow. The mixture was concentrated to ~8.6 L below 40° C. under vacuum. Methanol (6.79 kg) was added into the reactor. The reactor was adjusted to 45-55° C., then methanol (23.70 kg) and crystal seed (71.5 g) were added into the reactor and stirred for 1 h. Methanol (11.30 kg) was added into the reactor over 4 h and stirred for 0.5 h. The reactor was adjusted to 0° C. over 2 h and stirred for 18 h, the wet cake was isolated by filter and rinsed with methanol (11.30 kg) and heptane (4.86 kg) successively. After drying at 45° C. for 18 h under vacuum, 6.75 kg dried crude was obtained.

The above 6.75 kg dried crude and heptane (20.4 kg) was added into the reactor. The suspension solution was adjusted to 50° C., and stirred at 50° C. for 2 h, then cooled to 0° C. over 1 h, and stirred at 0° C. for 16 h. The suspension was filtered and rinsed with heptane (9.18 kg) to obtain wet cake. Drying wet cake in single cone under reduced pressure at 50~55° C. for 26 h to obtain 6.2 kg of pure product.

Example 5

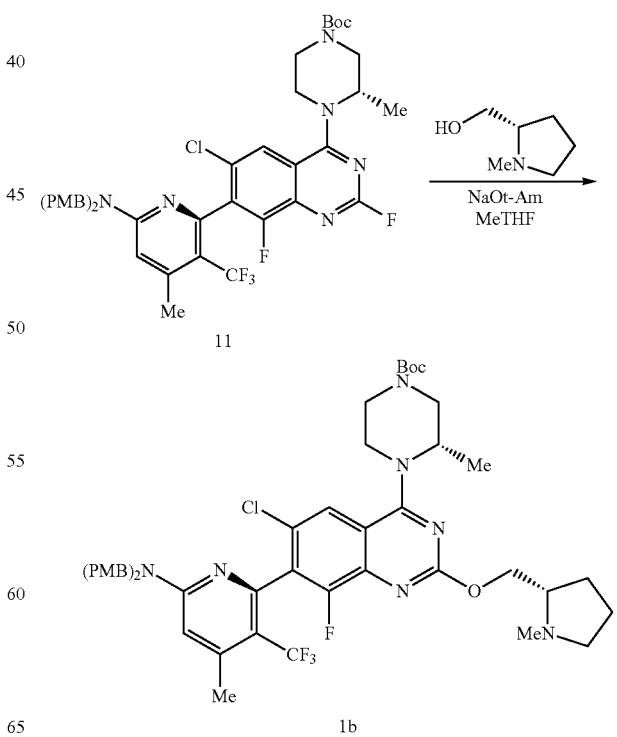

A solution of tert-butyl (3S)-4-[7-[6-[bis[(4-methoxyphenyl)methyl]amino]-4-methyl-3-(trifluoromethyl)-2-pyridyl]-6-chloro-2,8-difluoro-quinazolin-4-yl]-3-methyl-piperazine-1-carboxylate (50.0 g, 53.7 mmol, 1.00 equiv., 87.3% assay) and [(2S)-1-methylpyrrolidin-2-yl]methanol (7.44 g, 64.6 mmol, 1.20 equiv.) in 2-Me-THF (320 g) was concentrated under reduced pressure (235 mbar) to a 250 mL solution. The solution was cooled down to −10° C. Sodium tert-pentoxide (NaOt-Am) as a solution in toluene (24.8 g, 64.6 mmol, 1.30 equiv., 31% w/w) was then dosed over 10 to 60 min. The reaction mixture was stirred at 0° C. until full conversion was achieved (typically 1 h). Then, the reaction mixture was quenched onto a stirred biphasic mixture of potassium carbonate (200 g, 10% w/w solution), N-Acetyl-L-cysteine (24 g, 16% w/w aqueous solution) and 2-Me-THF (107 g), keeping the internal temperature between 15 and 30° C. The biphasic mixture was stirred for 1-2 h at 25° C. and the layers separated. The organic layer was further washed with potassium carbonate (100 g, 10% w/w aqueous solution) and then the organic layer was concentrated under reduced pressure (235 mbar) to a 250 mL solution, cooled down to 20-40° C. and polish filtered. The filtrate was further concentrated under reduced pressure (235 mbar) to a 175 mL solution. 1-PrOH (100 g) was added and a continuous exchange of 2-Me-THF to 1-PrOH was performed under reduced pressure (150 to 60 mbar). Then, water (100 g) was added at 50° C. and the solution was seeded at this temperature. The resulting mixture was further stirred at this temperature for at least 2 h and water (100 g) was added over at least 2 h. The crystal slurry was cooled down to 20° C. over at least 3 h and further stirred at this temperature for at least 5 h. The crystals were filtered off, washed with a solution of 1-PrOH/water and dried under reduced pressure until constant weight was attained. The title compound is isolated in 96% yield (47.5 g) as crystals. $^1$H NMR (600 MHz, DMSO-d6) δ ppm 7.82 (s, 1H), 7.16 (d, J=8.7 Hz, 4H), 6.87 (br d, J=8.3 Hz, 4H), 6.82 (s, 1H), 4.62-4.89 (m, 3H), 4.56 (br d, J=15.6 Hz, 2H), 4.39 (dd, J=10.7, 4.7 Hz, 1H), 4.12-4.25 (m, 1H), 4.05 (br d, J=13.4 Hz, 1H), 3.89-4.00 (m, 1H), 3.76-3.84 (m, 1H), 3.51-3.67 (m, 1H), 2.88-3.18 (m, 2H), 2.55-2.84 (m, 1H), 2.27-2.43 (m, 5H), 2.07-2.31 (m, 1H), 1.85-2.00 (m, 1H), 1.68 (br dd, J=13.3, 7.9 Hz, 3H), 1.42 (s, 9H), 1.28 (br d, J=6.6 Hz, 3H) ppm. HR-MS (ESI): calc. for C47H54ClF4N7O5 907.3811; found: 907.3808.

Example 6

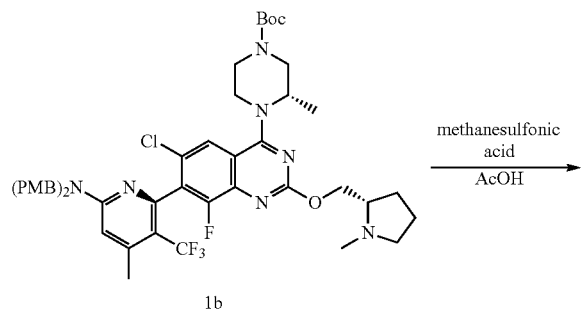

1b methanesulfonic acid
⎯⎯⎯⎯⎯⎯⎯→
AcOH

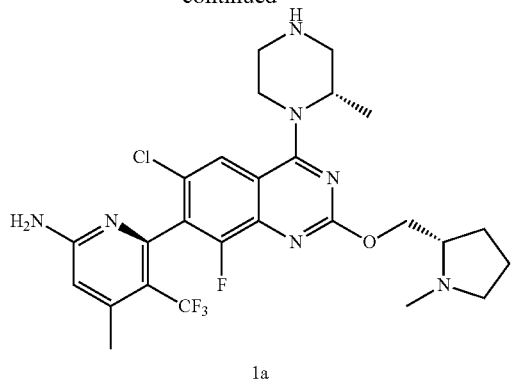

1a

To a mixture of acetic acid (46.2 g), methanesulfonic acid (52.9 g) and toluene (34.7 g) at 40° C. was added a solution of tert-butyl (3S)-4-[7-[6-[bis[(4-methoxyphenyl)methyl]amino]-4-methyl-3-(trifluoromethyl)-2-pyridyl]-6-chloro-8-fluoro-2-[[(2S)-1-methylpyrrolidin-2-yl]methoxy]quinazolin-4-yl]-3-methyl-piperazine-1-carboxylate (20.0 g, 22.0 mmol) in toluene (86.7 g) over at least 15 min. The reaction mixture was then heated to 52° C. until full conversion is achieved (typically 2 h). Then, the reaction mixture was cooled down to 25° C. and the layers separated. The acidic layer slowly quenched (typically over 1 h) over a mixture of aqueous sodium hydroxide (211.5 g, 28% w/w), water (80.0 g) and toluene (121.4 g) at 40-55° C. Upon completion of the quench, acetic acid (10.0 g) added to rinse the line. The biphasic mixture was warmed up to 50° C. and the layers separated. The organic layer was washed two times with aqueous sodium hydroxide (2×90.0 g, 0.1N solution). Then, distillation under reduced pressure at constant volume (90 mbar; typically 69 g of toluene is exchanged) of the toluene layer was performed. After polish filtration, the resulting toluene solution was concentrated under reduced pressure (90 mbar) to a 94 mL solution, which was then warmed up to 60° C. Then, n-heptane (34.6 g) was added over at least 30 min and the solution was seeded at this temperature. The resulting mixture was further stirred at this temperature for at least 1 h and the crystal slurry was cooled down to 0° C. over at least 4 h and further stirred at this temperature for at least 1 h. The crystals were filtered off, washed with a solution of toluene/n-heptane (1:1 v/v) and dried under reduced pressure until constant weight was attained. The title compound was isolated in 89% yield (11.7 g) as crystals. $^1$H NMR (600 MHz, DMSO-d6) δ ppm 7.74 (d, J=0.9 Hz, 1H), 6.84 (s, 2H), 6.49 (s, 1H), 4.54-4.65 (m, 1H), 4.38 (dd, J=10.8, 4.6 Hz, 1H), 4.14 (dd, J=10.7, 6.5 Hz, 1H), 3.96 (br d, J=13.1 Hz, 1H), 3.47-3.57 (m, 1H), 2.89-3.00 (m, 3H), 2.73-2.82 (m, 2H), 2.55-2.60 (m, 1H), 2.32-2.40 (m, 7H), 2.12-2.20 (m, 1H), 1.94 (dd, J=11.9, 7.6 Hz, 1H), 1.67 (br d, J=8.3 Hz, 3H), 1.40 (d, J=6.9 Hz, 3H) ppm. HR-MS (ESI): calc. for C26H30ClF4N7O 567.2136; found: 567.2141.

Example 7

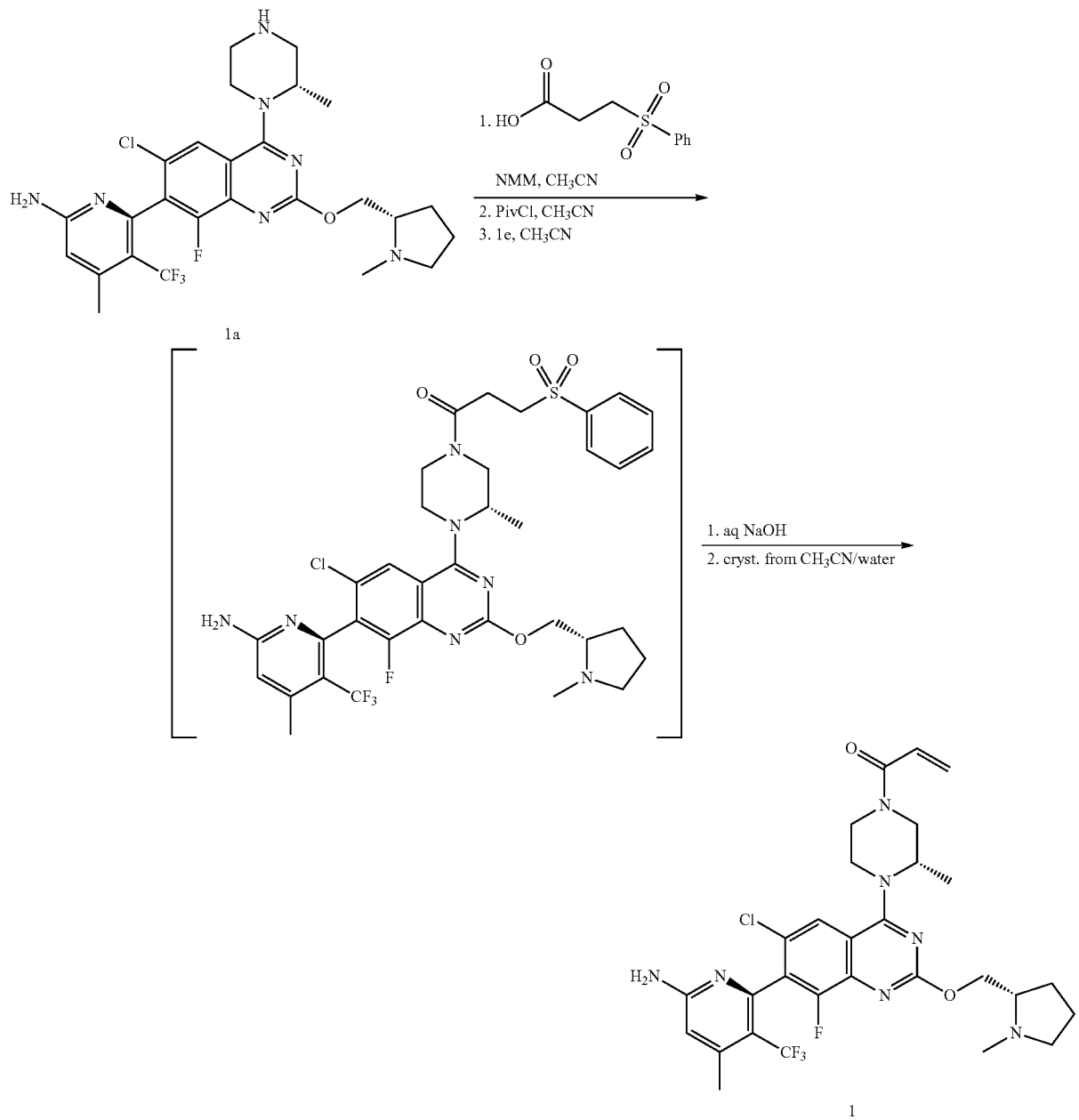

A solution of 3-(phenylsulfonyl)propionic acid (22.9 g, 106 mmol, 1.33 equiv), N-methylmorpholine (13.4 g, 133 mmol, 1.65 equiv) in acetonitrile (180.7 g) was cooled down to −10° C. Pivaloyl chloride (11.8 g, 97.9 mmol, 1.22 equiv) was dosed over 30 min. The reaction mixture was further stirred for 1 h at this temperature. Then, a solution of Compound 1e (50.0 g, 80.4 mmol, 1.00 equiv) in acetonitrile (176.9 g) was added onto the cold reaction mixture over 1 h and further stirred at −10° C. until full conversion to the sulfone intermediate was achieved (typically 1 h). The reaction mixture was warmed up to 15° C. and quenched by the addition of water (50.4 g) and aqueous sodium hydroxide (68.9 g, 483 mmol, 6.0 equiv, 28% w/w solution) was added. Stirring was continued until full conversion was obtained (typically 15 h) and the mixture was seeded followed by the addition of water (900 g) over at least 2 h. The crystal slurry was further stirred at this temperature for at least 42 h and the crystals were filtered off, washed with a solution of acetonitrile/water (3:7 v/v), washed with water and then dried under reduced pressure until constant weight was attained. The title compound was isolated in 91% yield (45.6 g) as crystals. 1H NMR (600 MHz, DMSO-d6) δ 7.82 (s, 1H), 6.73-6.98 (m, 3H), 6.50 (s, 1H), 6.10-6.28 (m, 1H), 5.68-5.81 (m, 1H), 4.66-4.85 (m, 1H), 4.32-4.46 (m, 1H), 4.25 (br d, J=13.5 Hz, 1H), 4.06-4.21 (m, 2H), 3.98 (br d, J=13.4 Hz, 1H), 3.38-3.76 (m, 2H), 2.91-3.27 (m, 2H), 2.53-2.68 (m, 1H), 2.37 (br d, J=1.4 Hz, 6H), 2.11-2.26 (m, 1H), 1.87-2.00 (m, 1H), 1.56-1.79 (m, 3H), 1.27 (br dd, J=11.7, 6.7 Hz, 3H) ppm. HR-MS (ESI): calc. for C29H32ClF4N7O2 621.2242; found: 621.2257.

Example 7a
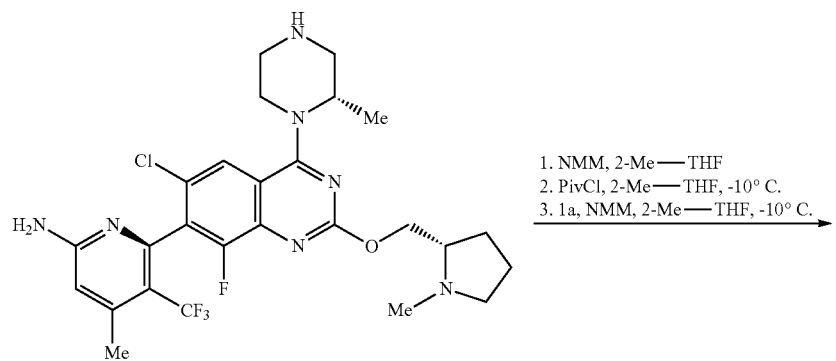
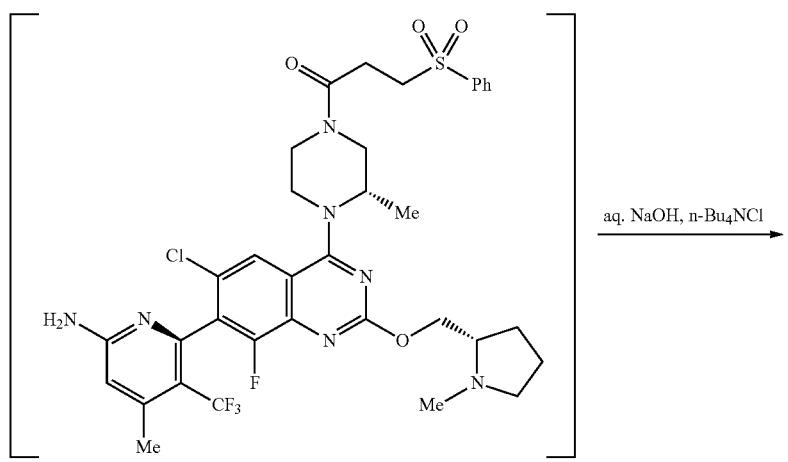
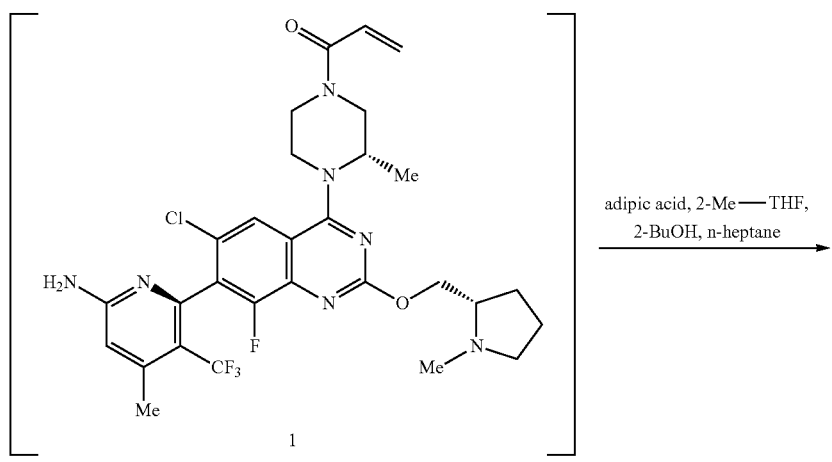

-continued

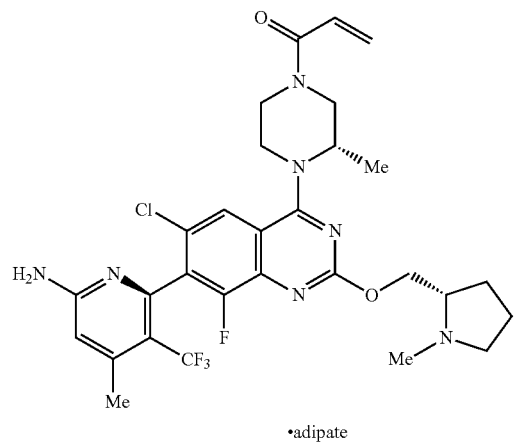
•adipate

N-methylmorpholine (10.67 g, 1.65 equiv) was added to a solution of 3-(phenylsulfonyl)propionic acid (18.91 g, 1.38 equiv.) in 2-Me-THF (136.6 g) at 20° C. Pivaloyl chloride (9.56 g, 1.24 equiv) was dosed over 30 min keeping the internal temperature at −20-0° C. The reaction mixture was further stirred for 1 h at this temperature. Then, a solution of Compound 1a (40.0 g, 1.00 equiv, 90.8% assay) and N-methylmorpholine (6.47 g, 1.00 equiv) in 2-Me-THF (136.6 g) was added onto the cold reaction mixture over 1 h and further stirred at −10° C. until full conversion to the sulfone intermediate was achieved (typically 1 h). The reaction mixture was filtered and quenched by the addition of aqueous sodium hydroxide (31.2 g, 3.40 equiv., 28% w/w solution), tetrabutylammonium chloride hydrate (3.55 g, 0.19 equiv.) and water (17.2 g) was added at 0-25° C. The reaction mixture was stirred at 20-30° C. until full conversion to Compound 1 was achieved (typically 2.5 h) and aqueous sodium chloride was added (46.0 g, 20% w/w solution). The layers were separated. The organic layer was successively washed with aqueous sodium bicarbonate (82.4 g, 5% w/w) and sodium chloride (82.4, 5% w/w). The organic layer was then concentrated under reduced pressure to a volume of 200 mL and 2-Me-THF was exchanged until the desired water content was achieved and then cooled down to 20° C. After polish filtration, the resulting 2-Me-THF solution was concentrated under reduced pressure to a 100 mL solution. 2-BuOH (307.9 g) was added at 35-45° C. and adipic acid (10.28 g, 1.10 equiv.) was added at this temperature and a solution was obtained. The solution was seeded at 30-40° C. and further aged at this temperature for 1.5 h. n-Heptane (161.4 g) was added to the crystal slurry at 30-40° C. over 30 min. The crystallization mixture was further aged at this temperature for at least 2 h, and cooled down to 0° C. over at least 6 h. After aging for at least at 0° C. for at least 6 h, the crystals were filtered off, washed with a solution of 2-BuOH/n-Heptane (1:1 v/v) and dried under reduced pressure until constant weight was attained. The title compound was isolated in 93% yield (45.2 g) as crystals. $^1$H NMR (600 MHz, DMSO-$d_6$) δ 7.77 (s, 1H), 6.81 (s, 2H), 6.76 (dd, J=16.8, 10.6 Hz, 1H), 6.45 (s, 1H), 6.18-6.10 (m, 1H), 5.70 (dd, J=10.4, 2.3 Hz, 1H), 4.75-4.66 (m, 1H), 4.38-4.30 (m, 2H), 4.25-3.89 (m, 4H), 3.61 (dq, J=21.3, 12.4, 10.9 Hz, 2H), 3.20 (dd, J=13.4, 3.8 Hz, 1H), 3.00 (td, J=12.6, 3.7 Hz, 1H), 2.91 (ddd, J=9.0, 6.0, 2.8 Hz, 1H), 2.59-2.51 (m, 1H), 2.32 (d, J=6.2 Hz, 6H), 2.15 (td, J=8.6, 7.7, 4.7 Hz, 5H), 1.94-1.85 (m, 1H), 1.61 (dddd, J=20.8, 12.3, 8.0, 4.1 Hz, 3H), 1.45 (h, J=3.4 Hz, 4H), 1.22 (dd, J=12.4, 6.6 Hz, 3H); $^{13}$C{$^1$H, $^{19}$F} NMR (151 MHz, DMSO-$d_6$) δ 174.9, 165.5, 164.8, 162.2, 161.4, 153.2, 148.8, 147.7, 143.0, 131.1, 128.5, 128.4, 128.3, 128.2, 125.6, 125.3, 121.0, 114.7, 112.2, 110.5, 69.8, 63.9, 57.4, 52.5, 52.4, 49.4, 45.9, 45.2, 44.9, 44.3, 42.0, 41.7, 40.6, 34.0, 29.1, 24.6, 23.1, 20.3, 15.9, 15.3; $^{19}$F NMR (565 MHz, DMSO-$d_6$) δ −53.5, −125.9.

Example 7b

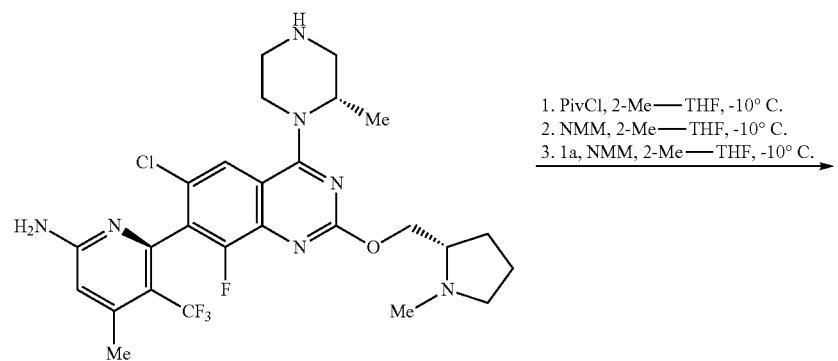

1. PivCl, 2-Me—THF, -10° C.
2. NMM, 2-Me—THF, -10° C.
3. 1a, NMM, 2-Me—THF, -10° C.

-continued

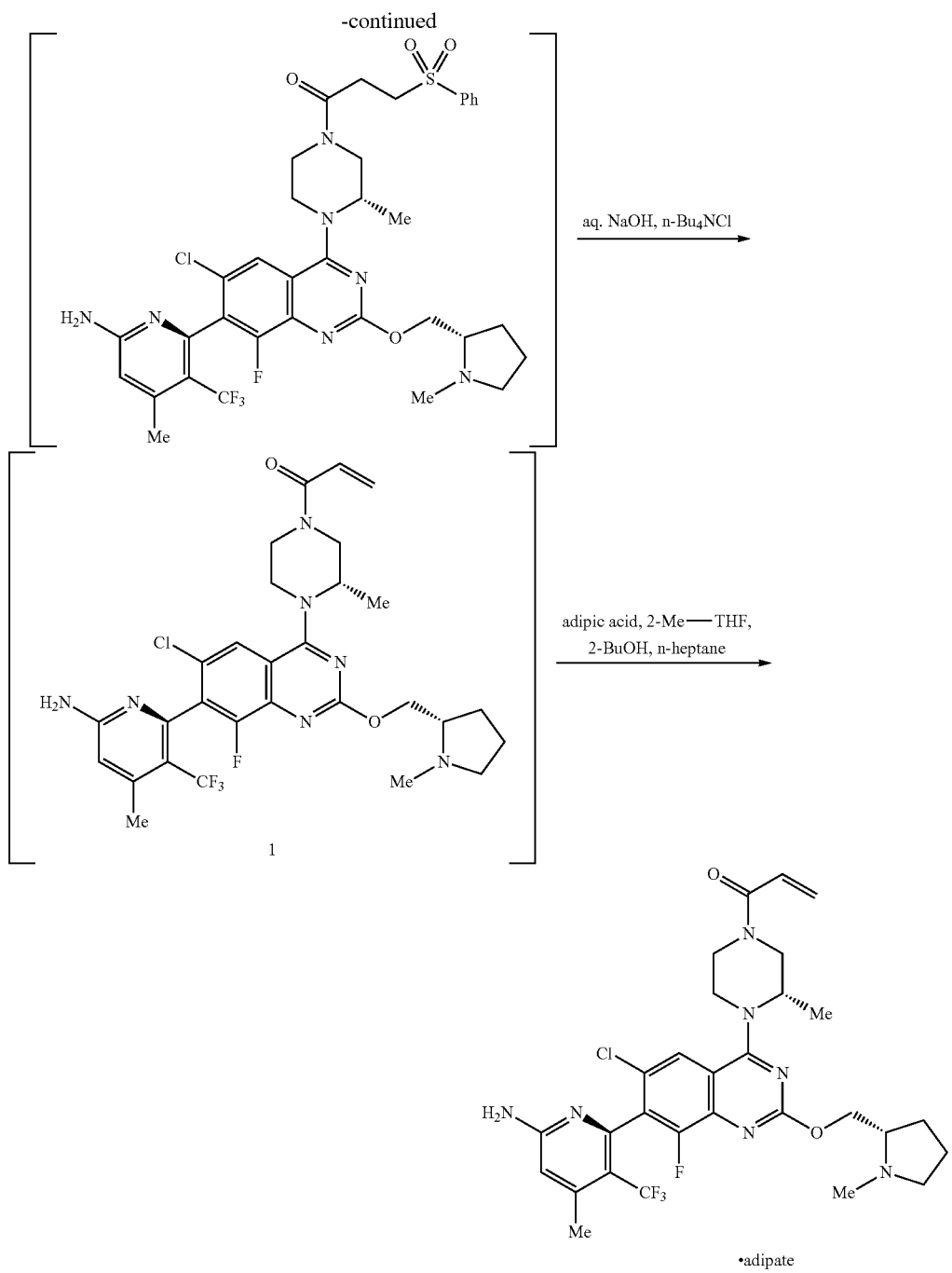

Pivaloyl chloride (9.56 g, 1.24 equiv) was added to a solution of 3-(phenylsulfonyl)propionic acid (18.91 g, 1.38 equiv.) in 2-Me-THF (136.6 g) at −20-0° C. N-methylmorpholine (10.67 g, 1.65 equiv) was slowly added, keeping the internal temperature at −20-0° C. The reaction mixture was further stirred for 1 h at this temperature. Then, a solution of Compound 1a (40.0 g, 1.00 equiv, 90.8% assay) and N-methylmorpholine (6.47 g, 1.00 equiv) in 2-Me-THF (136.6 g) was added onto the cold reaction mixture over 1 h and further stirred at −10° C. until full conversion to the sulfone intermediate was achieved (typically 1 h). The reaction mixture was filtered and quenched by the addition of aqueous sodium hydroxide (31.2 g, 3.40 equiv., 28% w/w solution), tetrabutylammonium chloride hydrate (18.2 g, 0.94 equiv.) and water (17.2 g) was added at 0-25° C. The reaction mixture was stirred at 20-30° C. until full conversion to Compound 1 was achieved (typically 1 h) and aqueous sodium chloride was added (46.0 g, 20% w/w solution). The layers were separated. The organic layer was successively washed with aqueous sodium bicarbonate (82.4 g, 5% w/w) and sodium chloride (82.4, 5% w/w). The organic layer was then concentrated under reduced pressure to a volume of 200 mL and 2-Me-THF was exchanged until the desired water content was achieved and then cooled down to 20° C. After polish filtration, the resulting 2-Me-THF solution was concentrated under reduced pressure to a 100 mL solution. 2-BuOH (307.9 g) was added at 35-45° C. and adipic acid (10.28 g, 1.10 equiv.) was added at this temperature and a solution was obtained. The solution was seeded at 30-40° C. and further aged at this temperature for 1.5 h. n-Heptane (161.4 g) was added to the crystal slurry at 30-40° C. over 30 min. The crystallization mixture was further aged at this temperature for at least 2 h, and cooled down to 0° C. over at least 6 h. After aging for at least at 0° C. for at least 6 h, the crystals were filtered off, washed with a solution of 2-BuOH/n-Heptane (1:1 v/v) and dried under reduced pressure until constant weight was attained. The title compound was isolated in 85% yield (42.7 g) as crystals. $^1$H NMR (600 MHz, DMSO-$d_6$) δ 7.77 (s, 1H), 6.81 (s, 2H), 6.76 (dd, J=16.8, 10.6 Hz, 1H), 6.45 (s, 1H), 6.18-6.10 (m, 1H), 5.70 (dd, J=10.4, 2.3 Hz, 1H), 4.75-4.66 (m, 1H), 4.38-4.30 (m, 2H), 4.25-3.89 (m, 4H), 3.61 (dq, J=21.3, 12.4, 10.9 Hz, 2H), 3.20 (dd, J=13.4, 3.8 Hz, 1H), 3.00 (td, J=12.6, 3.7 Hz, 1H), 2.91 (ddd, J=9.0, 6.0, 2.8 Hz, 1H), 2.59-2.51 (m, 1H), 2.32 (d, J=6.2 Hz, 6H), 2.15 (td, J=8.6, 7.7, 4.7 Hz, 5H), 1.94-1.85 (m, 1H), 1.61 (dddd, J=20.8, 12.3, 8.0, 4.1 Hz, 3H), 1.45 (h, J=3.4 Hz, 4H), 1.22 (dd, J=12.4, 6.6 Hz, 3H); $^{13}$C{$^1$H, $^{19}$F} NMR (151 MHz, DMSO-$d_6$) δ 174.9, 165.5, 164.8, 162.2, 161.4, 153.2, 148.8, 147.7, 143.0, 131.1, 128.5, 128.4, 128.3, 128.2, 125.6, 125.3, 121.0, 114.7, 112.2, 110.5, 69.8, 63.9, 57.4, 52.5, 52.4, 49.4, 45.9, 45.2, 44.9, 44.3, 42.0, 41.7, 40.6, 34.0, 29.1, 24.6, 23.1, 20.3, 15.9, 15.3; $^{19}$F NMR (565 MHz, DMSO-$d_6$) δ −53.5, −125.9.

Example 8

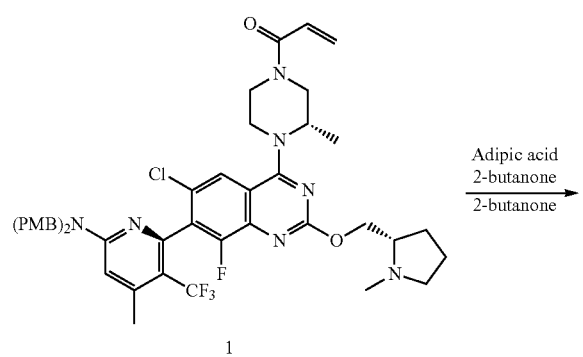

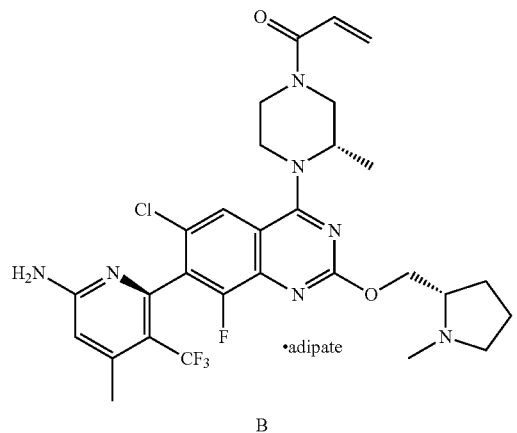

To a 25 L reactor equipped with an active nitrogen line, overhead agitation, and temperature probe was combined Compound 1 (2.32 kg, 3.53 mol) and polish-filtered 2-butanone (17.42 L, 7.5 L/kg). In a separate 5 L glass bottle was charged adipic acid (0.46 kg, 3.17 mol, 0.9 equiv) and polish-filtered 2-butanone (1.16 L, 0.5 L/kg). The reactor was then heated to 50° C.±10° C. and upon reaching the desired internal temperature target of >45° C., the adipic acid slurry in 2-butanone was charged to the reactor by vacuum pull. Compound B seeds (0.02 kg, 1 wt %) were charged to the 5 L glass bottle followed by polish-filtered butanone (2.32 L, 1.0 L/kg). Again, the slurry was charged to the reactor by vacuum pull. Finally, the 5 L glass bottle was rinsed with polish-filtered 2-butanone (1.16 L, 0.5 L/kg) then charged to the reactor via vacuum pull. The reactor contents were aged for a minimum of 1 h, cooled to 0° C. over a minimum of 2 h, then aged at 0° C. overnight (15 h). The contents were transferred to the pre-cooled filter dryer at 0° C. In parallel, polish-filtered 2-butanone (9.29 L, 4.0 L/kg) was charged to the reactor at 0° C. then stirred for 30 min. The material in the filter dryer was then filtered and the resulting cake washed with the chilled 2-butanone. After drying for a minimum of 8 h with vacuum pull and nitrogen sweep, the filter dryer contents were discharged to afford Compound 1 adipate (2.137 kg, 77%) as a solid. $^1$H NMR (600 MHz, DMSO-$d_6$) δ 7.77 (s, 1H), 6.81 (s, 2H), 6.76 (dd, J=16.8, 10.6 Hz, 1H), 6.45 (s, 1H), 6.18-6.10 (m, 1H), 5.70 (dd, J=10.4, 2.3 Hz, 1H), 4.75-4.66 (m, 1H), 4.38-4.30 (m, 2H), 4.25-3.89 (m, 4H), 3.61 (dq, J=21.3, 12.4, 10.9 Hz, 2H), 3.20 (dd, J=13.4, 3.8 Hz, 1H), 3.00 (td, J=12.6, 3.7 Hz, 1H), 2.91 (ddd, J=9.0, 6.0, 2.8 Hz, 1H), 2.59-2.51 (m, 1H), 2.32 (d, J=6.2 Hz, 6H), 2.15 (td, J=8.6, 7.7, 4.7 Hz, 5H), 1.94-1.85 (m, 1H), 1.61 (dddd, J=20.8, 12.3, 8.0, 4.1 Hz, 3H), 1.45 (h, J=3.4 Hz, 4H), 1.22 (dd, J=12.4, 6.6 Hz, 3H); $^{13}$C{$^1$H, $^{19}$F} NMR (151 MHz, DMSO-$d_6$) δ 174.9, 165.5, 164.8, 162.2, 161.4, 153.2, 148.8, 147.7, 143.0, 131.1, 128.5, 128.4, 128.3, 128.2, 125.6, 125.3, 121.0, 114.7, 112.2, 110.5, 69.8, 63.9, 57.4, 52.5, 52.4, 49.4, 45.9, 45.2, 44.9, 44.3, 42.0, 41.7, 40.6, 34.0, 29.1, 24.6, 23.1, 20.3, 15.9, 15.3; $^{19}$F NMR (565 MHz, DMSO-$d_6$) 5-53.5, −125.9.

Example 9

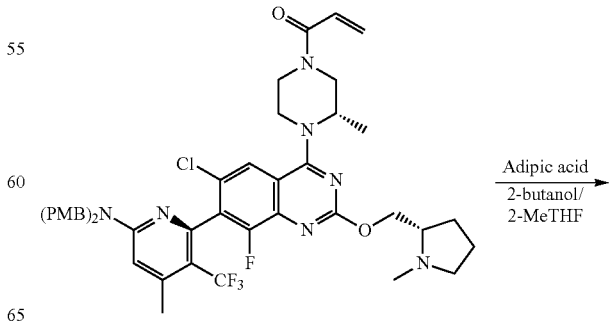

-continued

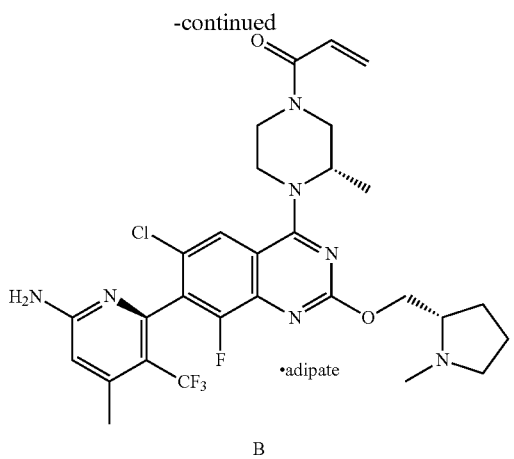

B

Compound 1 (1 mol-equiv) and adipic acid (1 mol-equiv) were suspended in 2-butanol and 2-methyltetrahydrofuran and dissolved upon heating to about 70° C. The polish-filtered solution was cooled to approx. 25° C. For seeding jet-milled Compound B material was used. Seeding material Compound 1 adipate suspended in 2-butanol/n-heptane. This suspension was used for seeding the solution at approx. 25° C. The seeding equipment was rinsed with n-heptane which then was added to the seeded suspension. N-Heptane was added at approx. 25° C. within 15-30 min. The suspension was stirred at approx. 25° C. for approx. 3 hours. The suspension was cooled to approx. 0° C. and stirred for at least 5 hours. The solid was isolated by solid/liquid separation and rinsed with a mixture of 2-butanol/n-heptane followed by n-heptane. The solid was dried at approx. 40° C. under reduced pressure to yield a powder in a yield of 88-95%.

In another procedure, Compound 1 (1 mol-equiv) and adipic acid (1 mol-equiv or an excess) were suspended in 2-butanol and 2-methyltetrahydrofuran and dissolved upon heating, to about 70° C. The polish-filtered solution was cooled to the seeding temperature (about 25° C.). For seeding Compound 1 adipate was used either without pre-treatment, or after impact-milling, jet-milling, or wet-milling. Seeding material Compound 1 adipate was suspended in a solvent (n-heptane, or 2-butanol/n-heptane mixtures, or 2-butanol). This suspension was used for seeding at the seeding temperature. The seeding equipment was rinsed with solvent (n-heptane, or 2-butanol/n-heptane mixtures, or 2-butanol, respectively) which then was added to the seeded suspension. N-Heptane was added at the seeding temperature or at a lower temperature (typically, at approx. 25° C.) for about 15-30 min. The suspension was stirred at the temperature of n-heptane addition for at least 3 hours. The suspension was cooled to approx. 0° C. and stirred for at least 5 hours. The solid was isolated by solid/liquid separation and rinsed with a mixture of 2-butanol/n-heptane followed by n-heptane. The solid was dried at approx. 40° C. under reduced pressure to yield a powder in a yield of 88-95%.

Example 10

Compound 1 adipate was dissolved in 2-butanol and 2-methyltetrahydrofuran upon heating, to about 67° C. The polish-filtered solution was cooled to the seeding temperature (about 45° C.). For seeding, wet-milled Compound 1 adipate was used. Compound 1 adipate was wet-milled in a solvent (n-heptane, or 2-butanol/n-heptane mixtures). This suspension was used for seeding at the seeding temperature. The seeding equipment was rinsed with solvent (n-heptane, or 2-butanol/n-heptane mixtures, respectively) which then was added to the seeded suspension. Pre-cooled n-Heptane (approx. 0° C.) was added for about 15-30 min. The thus cooled suspension was stirred at the temperature of approx. 25° C. for at least 3 hours. The suspension was cooled to approx. 0° C. and stirred for at least 2 hours. The solid was isolated by solid/liquid separation and rinsed with n-heptane or a mixture of 2-butanol/n-heptane followed by n-heptane. The solid was dried at approx. 40° C. under reduced pressure in a yield of 85-95%.

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Where a range of values is provided, it is understood that each intervening value, to the tenth of the unit of the lower limit, unless the context clearly dictates otherwise, between the upper and lower limit of the range and any other stated or intervening value in that stated range, is encompassed herein. The upper and lower limits of these small ranges which can independently be included in the smaller rangers is also encompassed herein, subject to any specifically excluded limit in the stated range. Where the stated range includes one or both of the limits, ranges excluding either or both of those included limits are also included herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A process for the synthesis of a compound of formula (I);

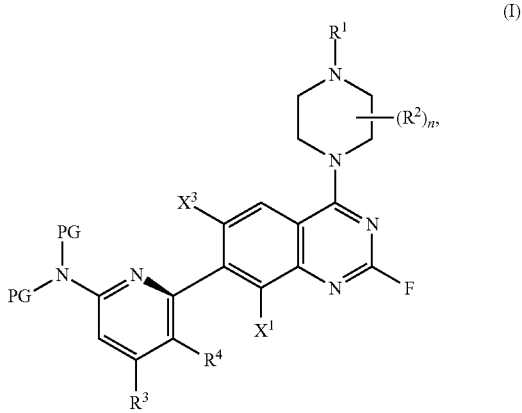

or a solvate, tautomer, stereoisomer, atropisomer, or salt thereof, wherein $X^1$ and $X^3$ are each independently hydrogen or halogen;

$R^1$ is hydrogen or $PG^1$;

each $R^2$ is independently halogen, cyano, unsubstituted $C_{1-6}$ alkyl, unsubstituted $C_{1-6}$ cyanoalkyl, or unsubstituted $C_{1-6}$ haloalkyl;

$R^3$ is hydrogen, halogen, $R^{3A}$-substituted or unsubstituted $C_{1-3}$ alkyl, $R^{3A}$-substituted or unsubstituted $C_{1-3}$ haloalkyl, or $R^{3A}$-substituted or unsubstituted cyclopropyl;

$R^{3A}$ is halogen, OH, CN, unsubstituted $C_{1-3}$ alkyl or unsubstituted $C_{1-3}$ haloalkyl;

$R^4$ is $R^{4A}$-substituted or unsubstituted $C_{1-3}$ haloalkyl;

$R^{4A}$ is unsubstituted $C_{1-3}$ alkyl;

n is 1 or 2;

each PG is independently an amino protecting group; and $PG^1$ is an amino protecting group;

wherein the process comprises (a) contacting a compound of formula (II)

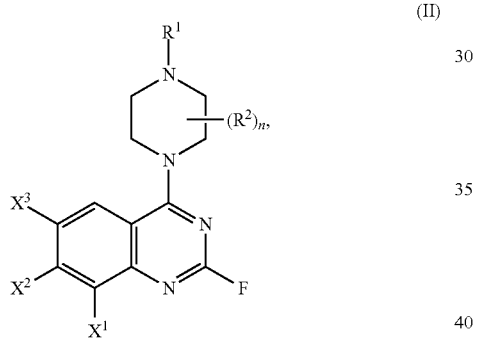

(II)

wherein $X^2$ is halogen;

with an organomagnesium compound thereby forming a compound of formula (IIa):

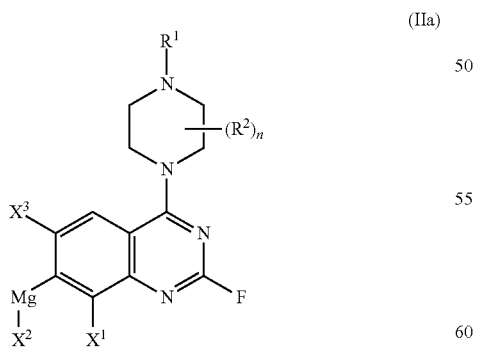

(IIa)

(b) transferring the compound of formula (IIa) of step (a) to a continuous stirred tank reactor (CSTR) comprising a zinc compound at a temperature of about −20° C. to 20° C. thereby synthesizing a compound of formula (IIb); and

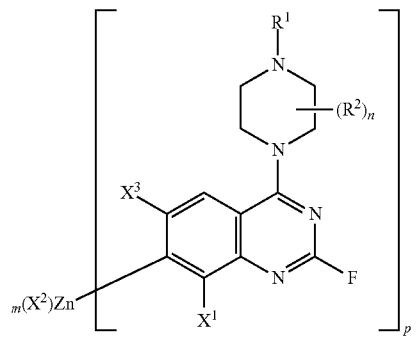

(IIb)

wherein m is 0, 1, or 2;

p is 1, 2, or 3; and $X^2$ is halogen or OPiv;

(c) contacting the compound (IIb) of step (b) with a compound of formula (III),

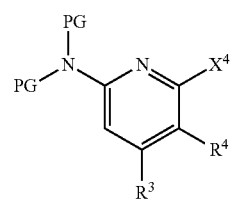

(III)

wherein $X^4$ is halogen, a transition metal catalyst precursor, and a chiral ligand, thereby synthesizing a compound of formula (I).

2. The process of claim 1, wherein $X^2$ is Br, Cl, or OPiv.

3. The process of claim 1, wherein the compound of formula (II) is prepared according to the process (P2):

(a) cyclizing a compound of formula (IV)

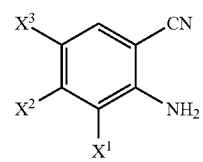

under $CO_2$ in the presence of a base to a compound of formula (V)

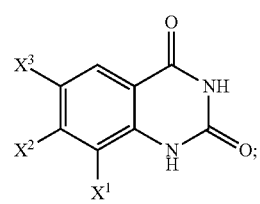

(b) contacting the compound of formula (V) with a chlorinating agent thereby synthesizing a compound of formula (Va)

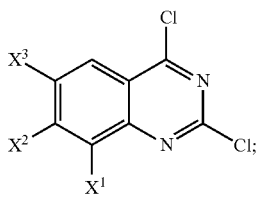

(c) contacting the compound of step (b) with a piperazinyl moiety having formula

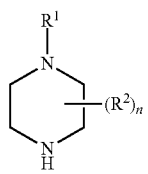

in the presence of a base, thereby synthesizing a compound of formula (Vb)

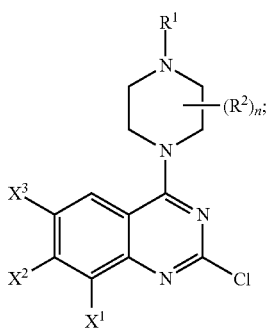

and (d) contacting the compound of step (c) with a fluorinating agent in the presence of a base thereby synthesizing a compound of formula (II).

4. The process of claim 3, wherein the base of step (a) is DBU.

5. The process of claim 3, wherein the chlorinating agent of step (b) is $POCl_3$.

6. The process of claim 3, wherein the base of step (c) is DIPEA.

7. The process of claim 3, wherein the fluorinating agent of step (d) is KF.

8. The process of claim 3, wherein the compound of formula (IV) is prepared according to the process (P3) comprising:

(a) contacting a compound of formula (IVa)

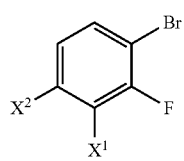

with i-PrMgCl thereby synthesizing a compound of formula (IVb)

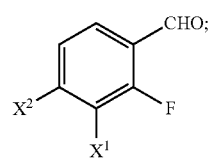

(b) contacting the compound of step (a) with hydroxylamine thereby synthesizing a compound of formula (IVc)

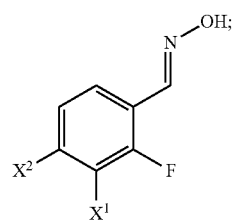

(c) contacting the compound of step (b) with a base and a dehydratization agent in acetonitrile thereby synthesizing a compound of formula (IVd)

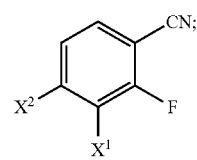

(d) contacting the compound of step (c) with ammonia thereby synthesizing a compound of formula (IVe)

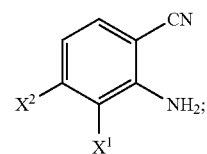

and (e) contacting the compound of step (d) with a chlorinating agent thereby synthesizing the compound of formula (IV).

9. The process of claim 1, wherein the compound of formula (III) is prepared according to the process (P4) comprising:

(a) contacting a compound of formula (VIa)

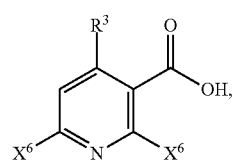

wherein $X^6$ is Cl or I, with a halogenating agent to form a compound of formula (VIb)

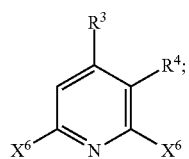

(b) brominating the compound of formula (VIb) to form a compound of formula

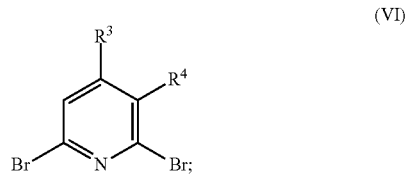
(VI)

and (c) contacting the compound of formula (VI) with a compound having formula NH(PG)$_2$ thereby making a compound of formula (III).

10. The process of claim 9, wherein $X^6$ is Cl.

11. The process of claim 9, wherein the halogenating agent is SF$_4$ in HF.

12. The process of claim 9, wherein the bromination is performed using HBr in an acid.

13. The process of claim 9, wherein the compound of formula (III) has formula:

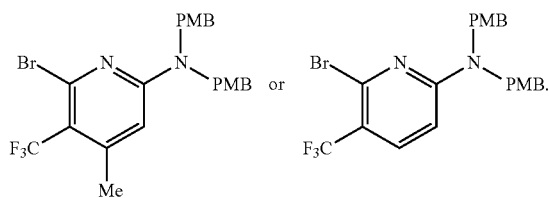

14. The process of claim 1, wherein $X^1$ is halogen.
15. The process of claim 1, wherein $X^1$ is F or Cl.
16. The process of claim 1, wherein $X^3$ is halogen.
17. The process of claim 1, wherein $X^3$ is F or Cl.
18. The process of claim 1, wherein $R^3$ is PG$^1$.
19. The process of claim 1, wherein PG$^1$ is Ac (acetyl), trifluoroacetyl, Bn (benzyl), Tr (triphenylmethyl or trityl), benzylidenyl, p-toluenesulfonyl, PMB (p-methoxybenzyl), Boc (tert-butyloxycarbonyl), Fmoc (9-fluorenylmethyloxycarbonyl) or Cbz (carbobenzyloxy).
20. The process of claim 1, wherein $R^1$ is Boc (tert-butyloxycarbonyl).
21. The process of claim 1, wherein $R^2$ is unsubstituted C$_{1-6}$ alkyl or unsubstituted C$_{1-6}$ cyanoalkyl.
22. The process of claim 21, wherein $R^2$ is methyl.
23. The process of claim 1, wherein $R^3$ is hydrogen or $R^{3A}$-substituted or unsubstituted C$_{1-3}$ alkyl.
24. The process of claim 23, wherein $R^3$ is methyl.
25. The process of claim 1, wherein $R^4$ is CF$_3$, CHF$_2$, or CH$_2$F.
26. The process of claim 1, wherein $R^3$ is methyl and $R^4$ is CF$_3$.
27. The process of claim 1, wherein each PG is independently a protecting group selected from the group consisting of Ac (acetyl), trifluoroacetyl, phthalimide, Bn (benzyl), Tr (triphenylmethyl or trityl), benzylidenyl, p-toluenesulfonyl, DMB (dimethoxybenzyl), PMB (p-methoxybenzyl), Boc (tert-butyloxycarbonyl), Fmoc (9-fluorenylmethyloxycarbonyl) or Cbz (carbobenzyloxy).

28. The process of claim 27, wherein each PG is p-methoxybenzyl.

29. The process of claim 1, wherein the organomagnesium compound is selected from the group consisting of isopropylmagnesium chloride, isopropylmagnesium bromide, isopropylmagnesium iodide, isopropylmagnesium chloride lithium chloride complex, sec-butylmagnesium chloride, lithium tri-n-butylmagnesiate, lithium triisopropylmagnesiate, and lithium (isopropyl)(di-n-butyl)magnesiate).

30. The process of claim 29, wherein the organomagnesium compound is i-PrMgCl·LiCl.

31. The process of claim 1, wherein the zinc compound is selected from the group consisting of ZnCl$_2$, ZnBr$_2$, ZnI$_2$, Zn(TFA)$_2$, Zn(OAc)$_2$, and Zn(OPiv)$_2$.

32. The process of claim 31, wherein the zinc compound is Zn(OPiv)$_2$·LiCl.

33. The process of claim 1, wherein the transition metal catalyst precursor is a Pd or Ni catalyst precursor is selected from the group consisting of Pd(OAc)$_2$, PdCl$_2$, PdCl$_2$(MeCN)$_2$, Pd(benzonitrile)$_2$Cl$_2$, Pd(dba)$_2$, Pd$_2$(dba)$_3$, Pd(PPh$_3$)$_4$, Pd(PCy$_3$)$_2$, Pd(PtBu$_3$)$_2$, Pd(TFA)$_2$, [Pd(allyl)Cl]$_2$, [Pd(cinammyl)Cl]$_2$, [PdCl(crotyl)]$_2$, PdCl(η5-cyclopentadienyl), [(η3-allyl)(η5-cyclopentadienyl)palladium(II)], [Ni(η5-cyclopentadienyl)(allyl)], [bis(1,5-cyclooctadiene)nickel(0)], NiCl$_2$, NiBr$_2$, Ni(OAc)$_2$, and Nickel(II) acetylacetonate.

34. The process of claim 1, wherein the chiral ligand is

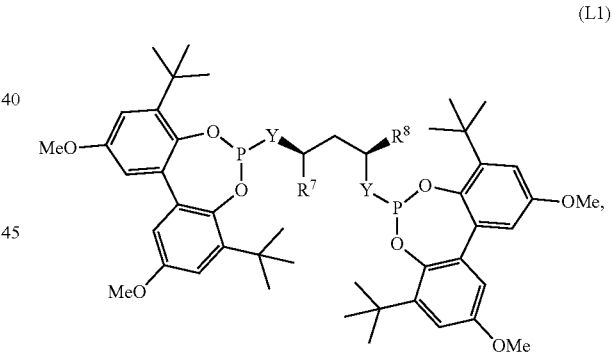
(L1)

wherein

Y is O or NR$^7$; and

R$^7$ and R$^8$ are independently unsubstituted C$_{1-6}$ alkyl.

35. The process of claim 34, wherein R$^7$ and R$^8$ are the same.

36. The process of claim 34, wherein R$^7$ and R$^8$ are each independently methyl, ethyl, or phenyl.

37. The process of claim 34, wherein the chiral ligand is (R,R)-chiraphite ligand.

38. The process of claim 1, wherein the zinc compound is Zn(OPiv)$_2$·LiCl, the Pd catalyst precursor is [Pd(cinammyl)Cl]$_2$, and the chiral ligand is (R,R)-chiraphite ligand.

39. The process of claim 1, wherein the compound of formula (I) has formula:

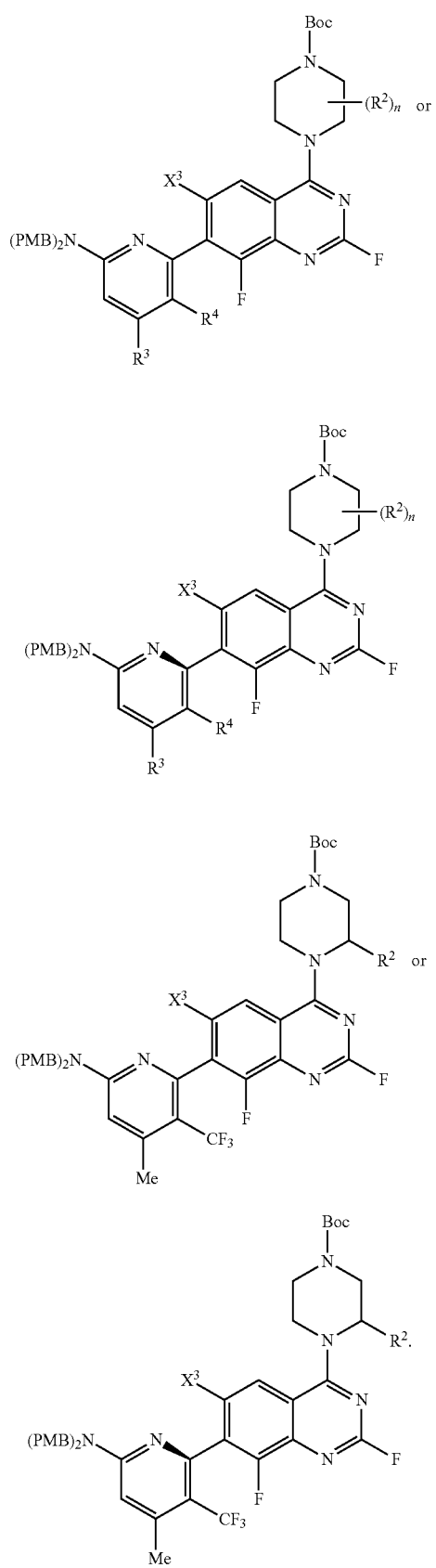
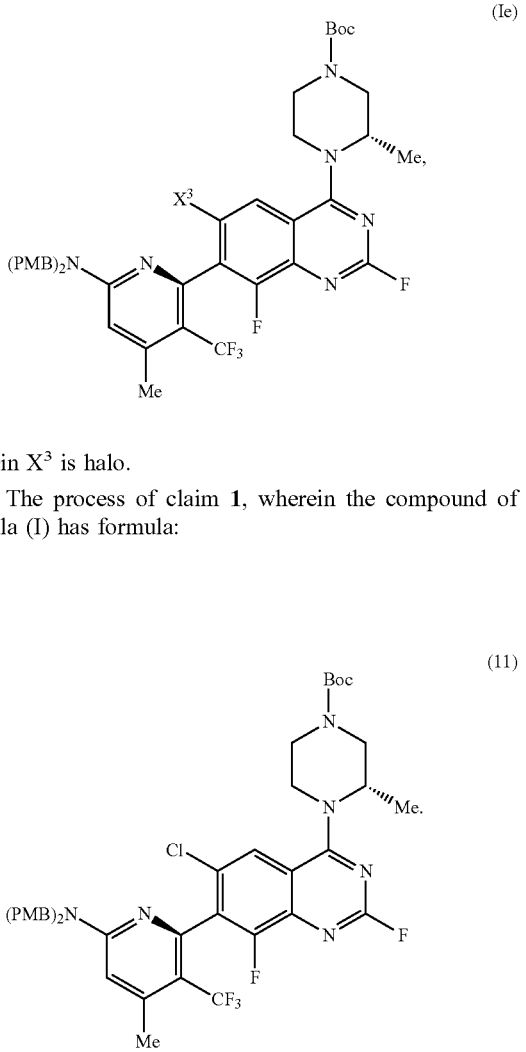
40. The process of claim 1, wherein the compound of formula (I) has formula:
wherein X³ is halo.
41. The process of claim 1, wherein the compound of formula (I) has formula:
42. A process (P5) for the synthesis of a compound of formula (2),
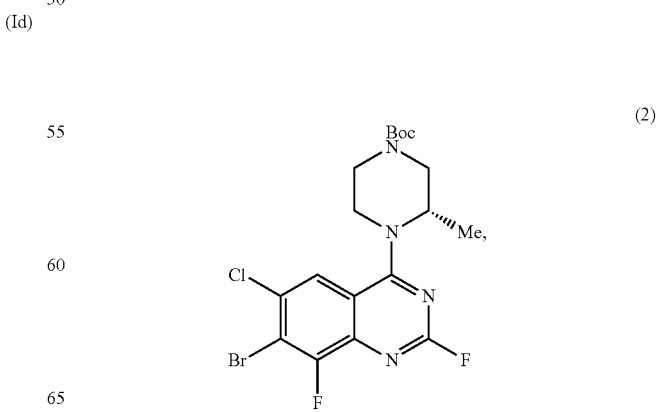

the process comprising the steps:
(a) contacting a compound of formula (4a)

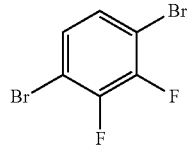

with i-PrMgCl followed by hydroxylamine, thereby synthesizing the compound of formula (4c)

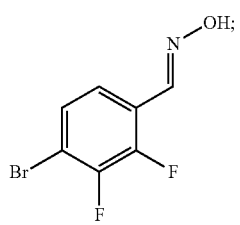 [SMILES: O/N=C/c1ccc(Br)c(F)c1F]

(b) contacting the compound of formula (4c) with TFAA and triethylamine in acetonitrile followed by ammonia, thereby synthesizing the compound of formula (4e)

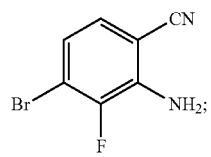 [SMILES: N#Cc1ccc(Br)c(F)c1N]

(c) contacting the compound of (4e) with a chlorinating agent, thereby synthesizing the compound of formula (4)

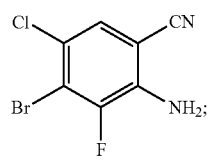 [SMILES: N#Cc1cc(Cl)c(Br)c(F)c1N]

(d) contacting the compound of (4) with $CO_2$ in the presence of DBU, thereby synthesizing the compound of formula (5)

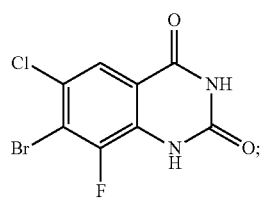 [SMILES: O=c1[nH]c(=O)c2cc(Cl)c(Br)c(F)c2[nH]1]

(e) contacting the compound of formula (5) with $POCl_3$ and DIPEA followed by tert-butyl (S)-3-methylpiperazine-1-carboxylate in DIPEA, thereby synthesizing the compound of formula (5b)

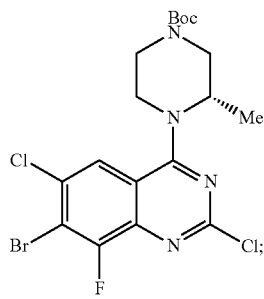 [SMILES: C[C@H]1CN(C(=O)OC(C)(C)C)CCN1c1nc(Cl)nc2c(F)c(Br)c(Cl)cc12]

and
(f) contacting the compound of (5b) with KF, DABCO, and MsOH, thereby forming the compound of formula (2).

43. The process of claim 1, wherein the compound of formula (III) has formula:

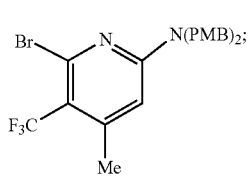

(3)

and wherein the compound of formula (3) is synthesized according a process (P6) comprising:
(a) contacting a compound of formula (6a)

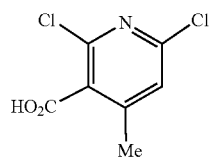 [SMILES: Cc1cc(Cl)nc(Cl)c1C(=O)O]

with $SF_4$ and HF thereby synthesizing a compound of formula (6b)

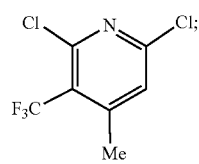

(b) contacting the compound of formula (6b) with HBr in AcOH to form a compound of formula (6)

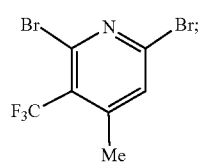 [SMILES: Cc1cc(Br)nc(Br)c1C(F)(F)F]

(c) contacting the compound of formula (6) with $(PMB)_2NH$, triethylamine, and NBP, thereby synthesizing the compound of formula (III).

44. The process of claim 1, wherein the process further comprises synthesizing a compound of formula (G) according to the process (P7),
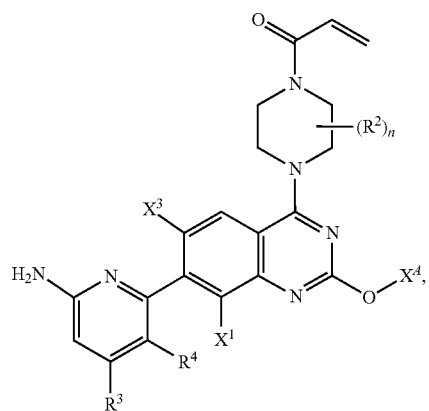
(G)
or a tautomer, stereoisomer, atropisomer, or pharmaceutically acceptable salt thereof, wherein;
$X^A$ is selected from the group consisting of
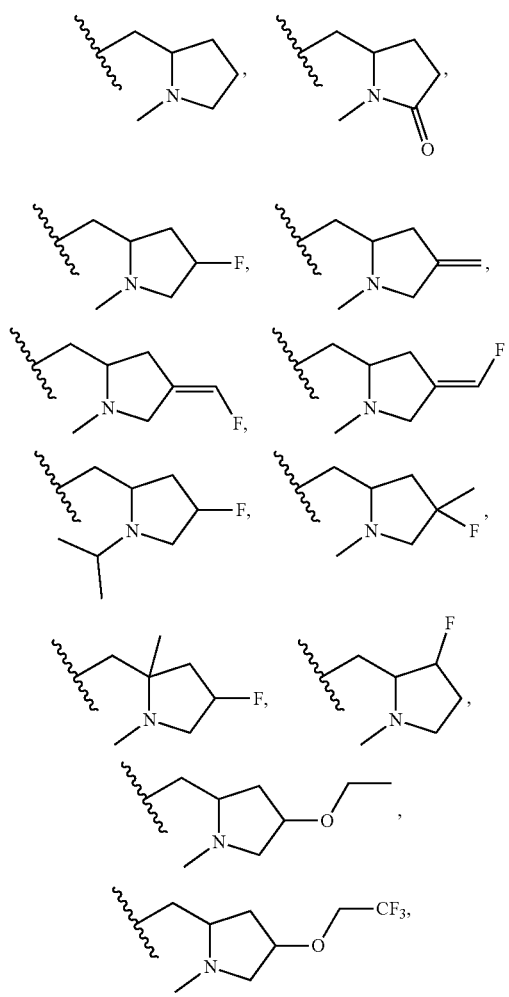
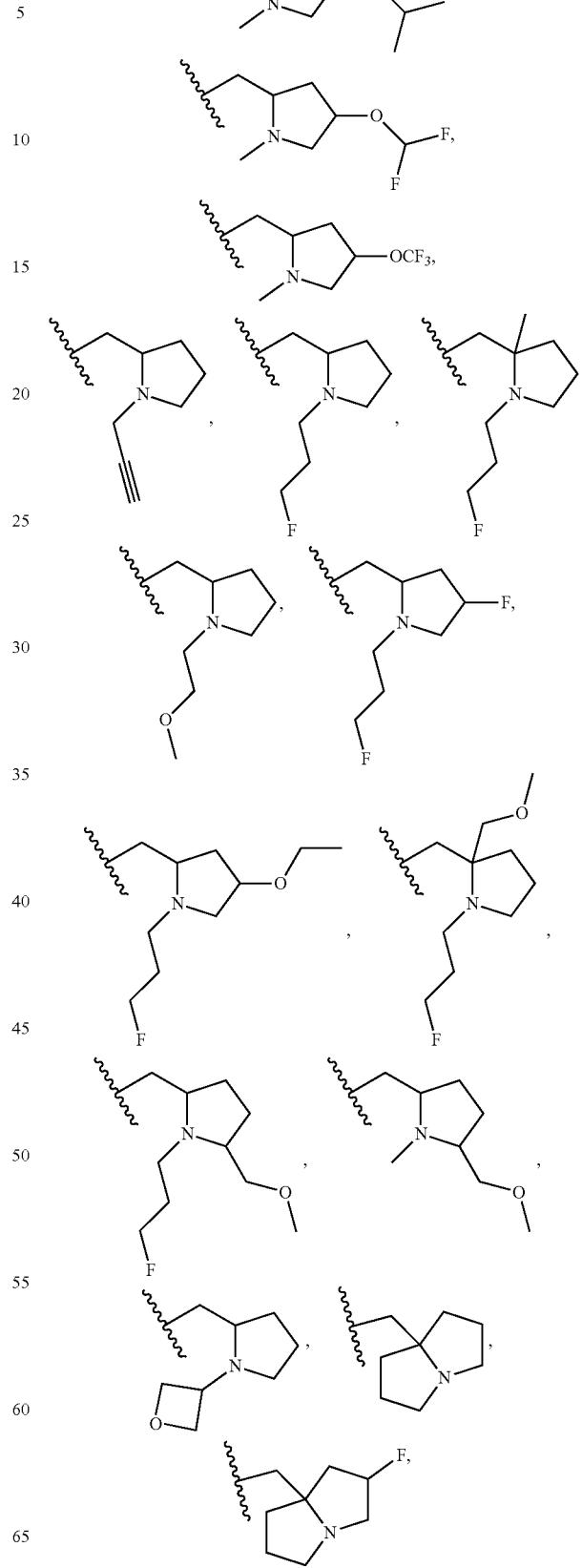

-continued

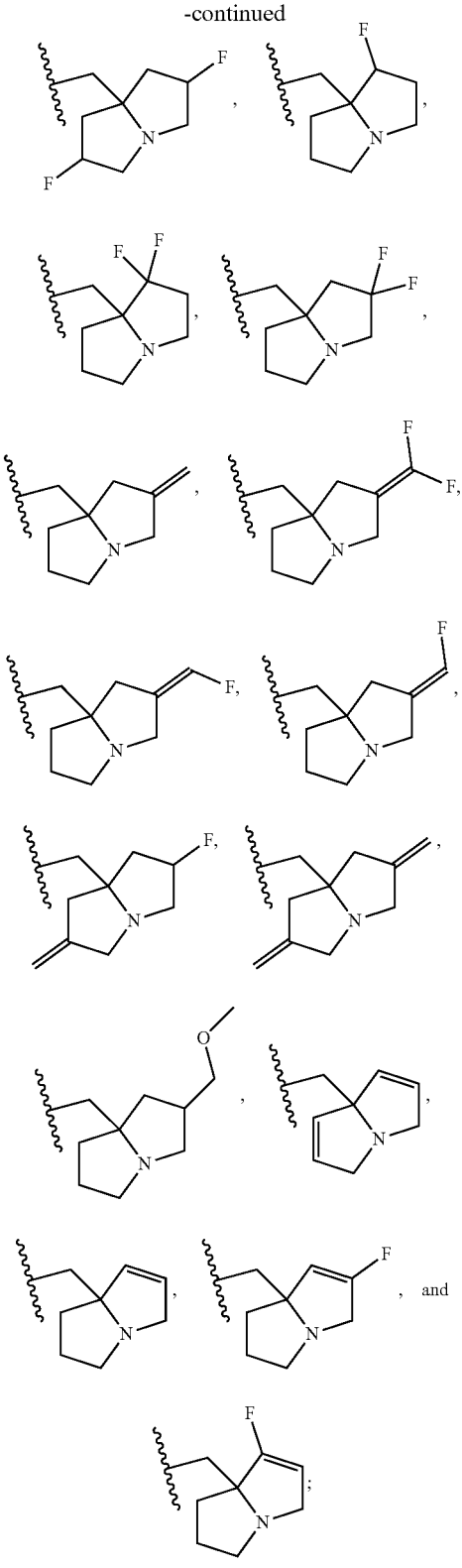

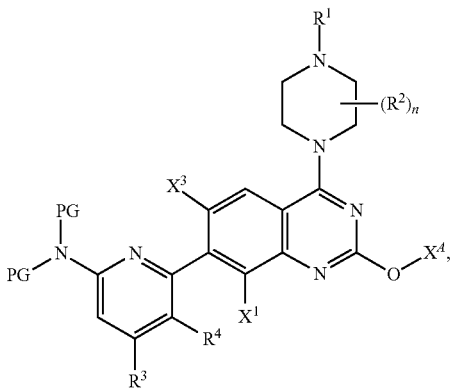

(b) removing the PG groups and optionally $R^1$ from the compound of formula (G1); and (c) contacting the compound of step (b) with a compound of formula (VII)

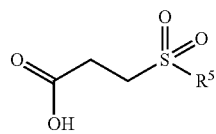

in the presence of an activating agent, followed by contacting with a base, thereby making a compound of formula (G) or a tautomer, stereoisomer, atropisomer, or pharmaceutically acceptable salt thereof.

45. A process (P9) for the synthesis of a compound of formula (1):

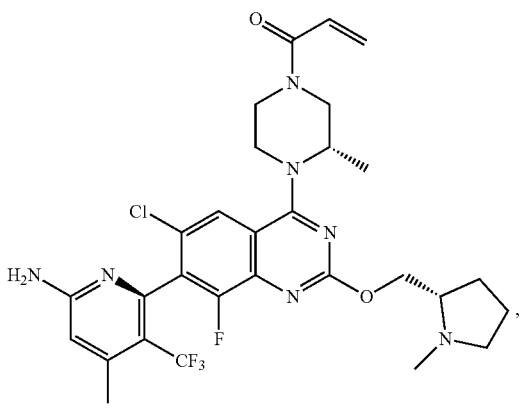

or a pharmaceutically acceptable salt thereof, the process comprising:

the process comprising:
(a) contacting the compound of formula (I) or a solvate, tautomer, stereoisomer, atropisomer, or salt thereof with a moiety comprising $X^A$ in the presence of base and an activating agent, thereby synthesizing a compound of formula (G1);

(a) contacting a precooled solution comprising a compound of formula (2)

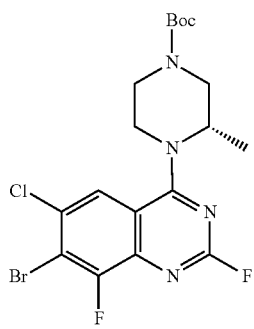

or a salt thereof with a pre-cooled solution comprising i-PrMgCl·LiCl using a flow rate resulting in a residence time of about 15-150 seconds for the Mg—Br exchange;

(b) transferring the mixture of step (a) to a continuous stirred tank reactor (CSTR) comprising a precooled solution of ZnCl$_2$ or Zn(OPiv)$_2$ and maintaining a constant residence time of about 3-7 minutes at about −20° C. to 20° C.;

(c) contacting the mixture of step (b) with NaTFA and a compound of formula (3)

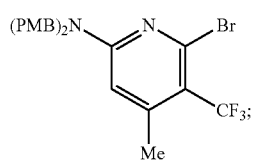

(d) contacting the mixture of step (c) or a salt thereof with a Pd or Ni catalyst precursor and a chiral ligand thereby synthesizing a compound of formula (11);

(11)

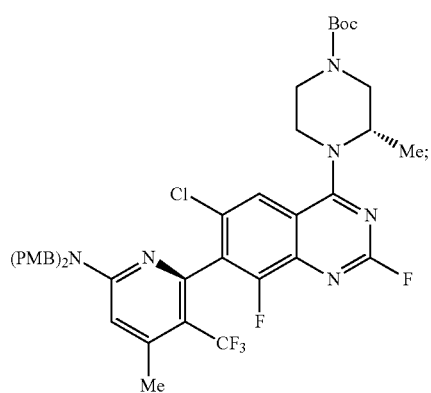

or a solvate or salt thereof, (e) contacting the compound of formula (11) or a solvate or salt thereof, with a compound of formula HO—X$^4$, wherein X$^4$ has formula

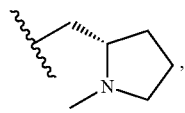

and a base thereby synthesizing a compound of formula (1b);

(1b)

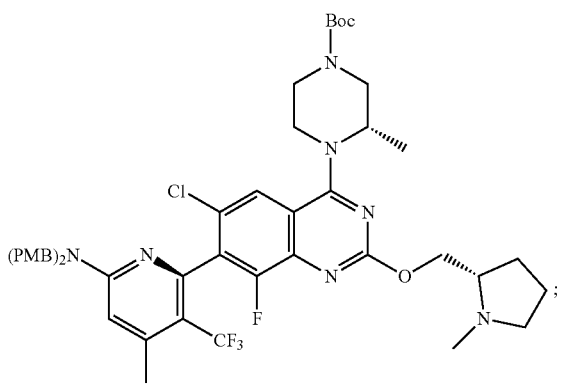

or a solvate or pharmaceutically acceptable salt thereof;

(f) contacting the compound of formula (1b) with MsOH in an acid thereby synthesizing a compound of formula (1a);

(1a)

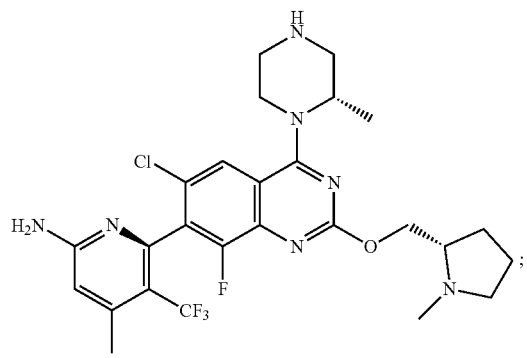

or a solvate or pharmaceutically acceptable salt thereof; and (g) contacting the compound of formula (1a) or a solvate or pharmaceutically acceptable salt thereof with

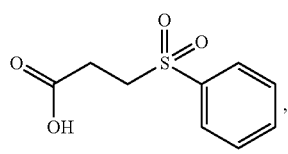 [SMILES: O=C(O)CCS(=O)(=O)c1ccccc1]

in the presence of an activating agent, followed by contacting with a base, thereby making a compound of formula (1) or a pharmaceutically acceptable salt thereof.

46. The process of claim 45, wherein the acid of step (f) is AcOH, trifluoroacetic acid, chlorosulfonic acid, sulfuric acid, HCl, HBr, p-toluenesulfonic acid, or trifluoromethanesulfonic acid.

47. The process of claim 45, wherein compound (2) is synthesized according to the process comprising the steps:

(a) contacting a compound of formula (4a)

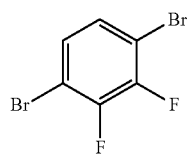

with i-PrMgCl followed by hydroxylamine, thereby synthesizing the compound of formula (4c)

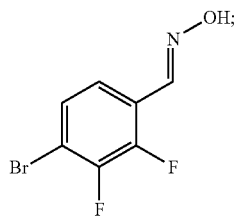 [SMILES: O/N=C/c1ccc(Br)c(F)c1F]

(b) contacting the compound of formula (4c) with TFAA and triethylamine in acetonitrile followed by ammonia, thereby synthesizing the compound of formula (4e)

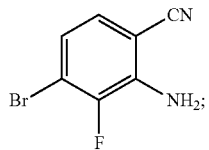 [SMILES: N#Cc1ccc(Br)c(F)c1N]

(c) contacting the compound of (4e) with a chlorinating agent, thereby synthesizing the compound of formula (4)

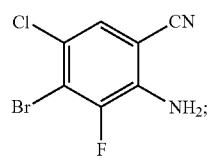

(d) contacting the compound of (4) with $CO_2$ in the presence of DBU, thereby synthesizing the compound of formula (5)

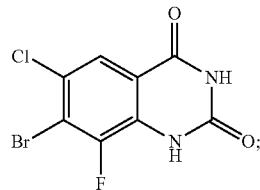 [SMILES: O=c1[nH]c(=O)c2cc(Cl)c(Br)c(F)c2[nH]1]

(e) contacting the compound of formula (5) with $POCl_3$ and DIPEA followed by tert-butyl (S)-3-methylpiperazine-1-carboxylate in DIPEA, thereby synthesizing the compound of formula (5b)

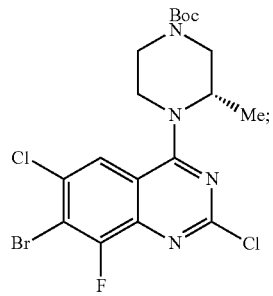 [SMILES: C[C@H]1CN(C(=O)OC(C)(C)C)CCN1c1nc(Cl)nc2c(F)c(Br)c(Cl)cc12]

and
contacting the compound of (5b) with KF, DABCO, and MsOH, thereby forming the compound of formula (2).

48. The process of claim 45, wherein the precooled solution of step (b) comprises $Zn(OPiv)_2 \cdot LiCl$.

* * * * *